United States Patent [19]
Bartfeld et al.

[11] Patent Number: 6,127,144
[45] Date of Patent: Oct. 3, 2000

[54] METHOD FOR EXPRESSION OF PROTEINS IN BACTERIAL HOST CELLS

[75] Inventors: Daniel Bartfeld, Vancouver, Canada; Michael J. Butler, Cambridge, United Kingdom; Dany Hadary, Vancouver, Canada; David L. Jenish, Mississauga, Canada; Timothy J. Krieger, Richmond, Canada; Lawrence T. Malek, Brampton, Canada; Gisela Soostmeyer, Kleinburg, Canada; Eva Walczyk, Mississuaga, Canada; Phyllis Krygsman, Brampton, Canada; Sheila Garven, Oakville, Canada

[73] Assignee: Cangene Corporation, Mississauga, Canada

[21] Appl. No.: 08/951,742

[22] Filed: Oct. 16, 1997

Related U.S. Application Data

[63] Continuation-in-part of application No. 08/265,310, Jun. 24, 1994, Pat. No. 5,856,166, which is a continuation-in-part of application No. 08/173,508, Dec. 23, 1993, Pat. No. 5,616,485.

[51] Int. Cl.$^7$ .............................. C12P 21/06; C12N 9/48; C12N 1/12; A61K 38/06
[52] U.S. Cl. ..................... 435/69.1; 435/252.1; 435/212; 530/331
[58] Field of Search .............................. 435/69.1, 252.1, 435/212; 530/331

[56] References Cited

U.S. PATENT DOCUMENTS

| | | | |
|---|---|---|---|
| 5,011,772 | 4/1991 | Recsei | 435/69.1 |
| 5,143,839 | 9/1992 | Blumberg et al. | 435/220 |
| 5,200,327 | 4/1993 | Garvin et al. | |
| 5,294,542 | 3/1994 | Sloma et al. | 435/69.1 |

FOREIGN PATENT DOCUMENTS

| | | |
|---|---|---|
| 1295563 | 4/1992 | Canada . |
| 1295566 | 4/1992 | Canada . |
| 1295567 | 4/1992 | Canada . |
| 0219237A1 | 4/1987 | European Pat. Off. . |
| 0 440 303 | 8/1991 | European Pat. Off. . |
| PCT/US92/05532 | 6/1992 | WIPO . |
| WO 92/16642 | 10/1992 | WIPO . |
| WO 93/00925 | 1/1993 | WIPO . |

OTHER PUBLICATIONS

Lin, F.–K. et al., Proc. Natl. Acad. Sci. USA, vol. 82, pp. 7580–7584, Nov. 1985.

Kettner, C. et al., Meth. Enzymol., vol. 80, pp. 826–842, 1981.

Gough et al. "Molecular cloning of cDNA encoding a murine haematopoietic growth regulator, granulocyte—macrophage colony stimulating factor," *Nature*, vol. 309, No. 28, pp. 763–767, Jun. 1984.

Lusis et al. "Translation of mRNA for human granulocyte–macrophage colony stimulating factor," *Nature*, vol. 298, pp. 75–76, Jul. 1, 1982.

Nowakowski et al. "Cloning of peptide genes from *Lactobacillus helveticus* CNRZ 32," *Applied Microbiology Biotechnology* (1993) 39:204–210.

Roig et al. "High–Alkaline Protease from Bacillus PB92 Entrapped in Calcium Alginate Gel: Physico–chemical and Microscopic Studies," *Applied Biochemistry and Biotechnology*, vol. 55, 1995.

Strauch et al. "Overproduction of *Salmonella typhimurium* Peptidase T," *Journal of Bacteriology*, vol. 156, No. 2, Nov. 1983, pp. 743–751.

Balaban et al. *Biokhimiya* 59(9):1033 (1994).

Pavlova et al. *Mikrobiologiya* 57:328 (1988).

Sharipova et al. *Biotechnol. 94—Ferment Physiol.* pp. 31–33 (1994).

Atlan, D., et al., "Isolation and Characterization of Aminopeptidase–Deficient *Lactobacillus bulgaricus* Mutants" *Applied and Environmental Microbiology*, 55(7): 1717–1723 (Jul. 1989).

Alvarez, N. G., et al., "Purification and characterization of a thermosensitive X–prolyl dipeptidyl aminopeptidase (dipeptidyl aminopeptidase yscV) . . . ", *Biochimica et Biophysica Acta* 832: 119–125 (1985).

Aretz, W., et al., "Proteolytic enzymes from recombinant *Streptomyces lividans* TK24", *FEMS Microbiology Letters* 65: 31–36 (1989).

Bålöw, R., et al., "Purification, Substrate Specificity, and Classification of Tripeptidyl Peptidase II", *The Journal of Biological Chemistry*, 261(5): 2409–2417 (1986).

Bender, E., et al., "Secretory synthesis of human interleukin–2 by *Streptomyces lividans*", *Gene*, 86: 227–232 (1990).

Bibb, M., et al., "Nucleotide sequences encoding and promoting expression of three antibiotic resistance genes indigenous to Streptomyces", *Mol Gen Genet* 199: 26–36 (1985).

Brawner, M., et al., "Expression of the Soluble CD–4 Receptor in Streptomyces", *J. Cell Biochem.*, CC036 (Abstract) 14A pp. 103 (1990).

Butler, M. J., et al., "Cloning of genetic loci involved in endoprotease activity in *Streptomyces lividans* 66: a novel neutral protease gene with an adjacent divergent putative . . . ", *Can. J. Microbiol.*, 38: 912–920 (1992).

Fukasawa, et al., "Purification and Properties of Dipeptidyl Peptidase IV from *Streptococcus mitis* ATCC 9811", *Archives of Biochemistry and Biophysics*, 210(1): 230–237 (1981).

Hanson, H., et al., "Crystalline Leucine Aminopeptidase from Lens (α–Aminoacyl–Peptide Hydrolase; EC 3.4.11.1", *Methods Enzymol.*, 45: 504–521 (1976).

(List continued on next page.)

Primary Examiner—Ponnathapu Achutamurthy
Assistant Examiner—Peter P. Tung
Attorney, Agent, or Firm—Foley & Lardner

[57] ABSTRACT

An aminopeptidase inhibitor is used when expressing heterologous protein in a bacterial host, such as Streptomyces. Use of such an inhibitor inhibits degradation of the heterologous protein by aminopeptidases. Inhibitors are designed based upon the mechanism and substrate specificity of the target protease and expressed protein.

14 Claims, 44 Drawing Sheets

OTHER PUBLICATIONS

Henderson, G., et al., "Characterization and Structure of Genes for Proteases A and B from *Streptomyces griseus*", *Journal of Bacteriology*, 169(8): 3778–3784 (1987).

Hopwood, D.A., et al., *Genetic Manipulation of Streptomyces: A Laboratory Manual*, Table of Contents (1985).

Ingram, C., et al., "xylE Functions as an Efficient Reporter Gene in Streptomyces spp.: Use for the Study of galP1, a Catabolite–Controlled Promoter", *Journal of Bacteriology*, 171(12): 6617–6624 (1989).

Kreil, G., "Processing of precursors by dipeptidylaminopeptidases: a case of molecular ticketing", *TIBS 15*, 23–26 (1990).

Lloyd, R.J., et al., "Characterization of X–propyl dipeptidyl aminopeptidase from *Lactococcus lactis* subsp. *lactis*", *Journal of General Microbiology* 137: 49–55 (1991).

Malek, L., et al., "Secretion of Granulocyte Macrophage–Colony Stimulating Factor (GM–CSF) in *Streptomyces Lividans*", *J. Cell Biochem.*, CC412 (Abstract) 14A pp. 127 (1990).

McDonald, J.K., et al., "Partial Purification and Characterization of an Ovarian Tripeptidyl Peptidase: A Lysosomal Exopeptidase . . . ", *Biochemical and Biophysical Research Communications*, 126(1): 63–71 (1985).

Menn, F., et al., "Location and sequence of the todF gene encoding 2–hydroxy–6–oxohepta–2,4–dienoate hydrolase in *Pseudomonas putida* F1", *Gene*, 104: 91–94 (1991).

Taguchi, S., et al., "Efficient Extracellular Expression of a Foreign Protein in Streptomyces Using Secretory Protease Inhibitor (SSI) Gene Fusions", *Bio/Technology*, 7: 1063–1066 (1989).

Tomkinson, B., et al., "Characterization of cDNA for Human Tripeptidyl Peptidase II: The N–Terminal Part of the Enzyme is Similar to Subtilisin", *Biochemistry* 30: 168–174 (1991).

Yoshimoto, T., et al., "Cloning and Expression of Aminopeptidase P Gene from *Escherichia coli* HB101 and Characterization of Expressed Enzyme", *J. Biochem* 104(1): 93–97 (1988).

Yoshimoto, T., et al., "Sequencing and High Expression of Aminopeptidase P Gene from *Escherichia coli* HB101", *J. Biochem* 105: 412–416 (1989).

Bender et al. "Synthesis and Secretion of Hirudin by *Streptomyces lividans*" *Appl. Microbiol. Biotechnol.* 34: 203–207 (1990).

Bibb et al. "The relationship between base composition and codon usage in bacterial genes and its use for the simple and reliable identification of protein–coding sequences." *Gene* 30: 157–166 (1984).

Fornwald et al. "Soluble forms of the human T cell receptor CD4 are efficiently expressed by *Streptomyces lividans*" *Bio/Technology* 11: 1031–1036 (1993).

Illingworth et al. "Secretion of the sweet–tasting plant protein thaumatin by *Streptomyces lividans*" *J. of Industrial Microbiology* 4: 37–42 (1989).

Koller et al. "Recombinant *Streptomyces lividans* secretes a fusion protein of tendamistat and proinsulin" *Biotechnology* 7: 1055–1059 (1989).

Lichenstein et al. "Secretion of interleukin–1β and *Escherichia coli* galactokinase by *Streptomyces lividans*" *J. Bacteriology* 170: 3924–3929 (1988).

Schoellmann et al. "Direct evidence for the presence of histidine in the active center of chymotrypsin" *Biochemistry* 2: 252 (1963).

Shaw et al. "Evidence for an active center histidine in trypsin through the use of a specific reagent, TLCK, the chloromethyl ketone derived from N–tosyl–lysine" *Biochemistry* 4: 2219 (1965).

Ueda et al. "Synthesis and expression of a DNA encoding the Fv domain of an anti–lysozyme monoclonal antibody, HyHEL10, in *Streptomyces lividans*" *Gene* 129: 129–134 (1993).

Aphale et al., J. General Microbiology 139: 417–424 (1993).

Krieger et al., FEBS Letters 352: 385–388 (1994).

Lichenstein et al., Gene 111: 125–130 (1992).

Chemical Abstracts, vol. 119, No. 3, Abstract No. 23336 (Jul. 19, 1993).

1 2 3 4

1 2 st kD

- 43.0
- 30.0
- 20.1
- 14.4

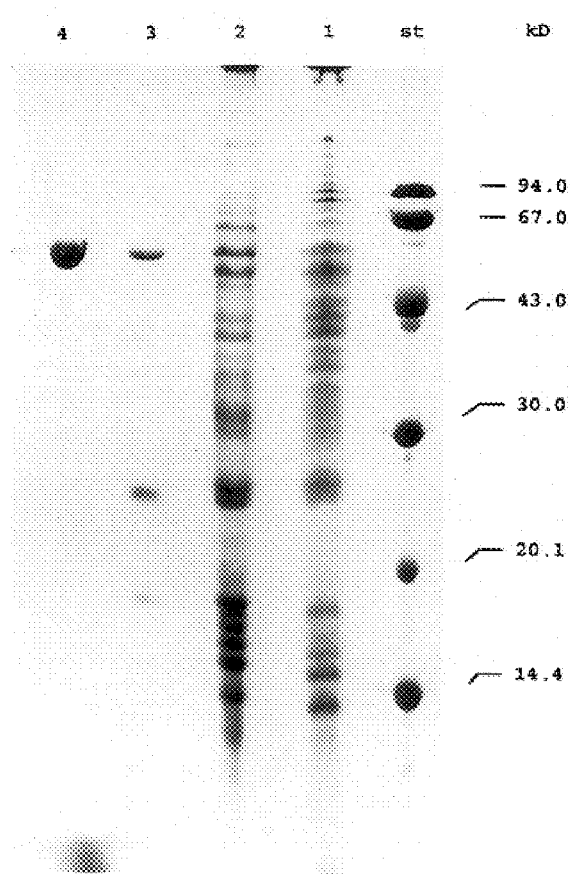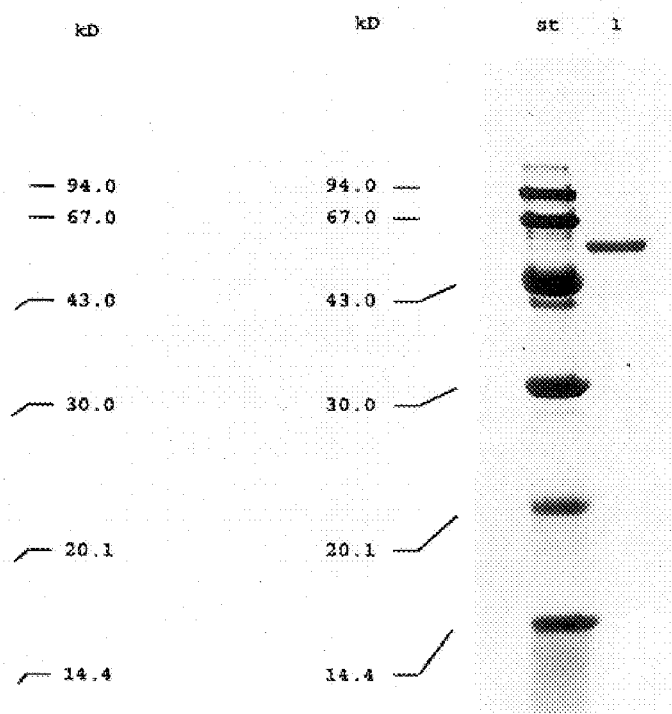

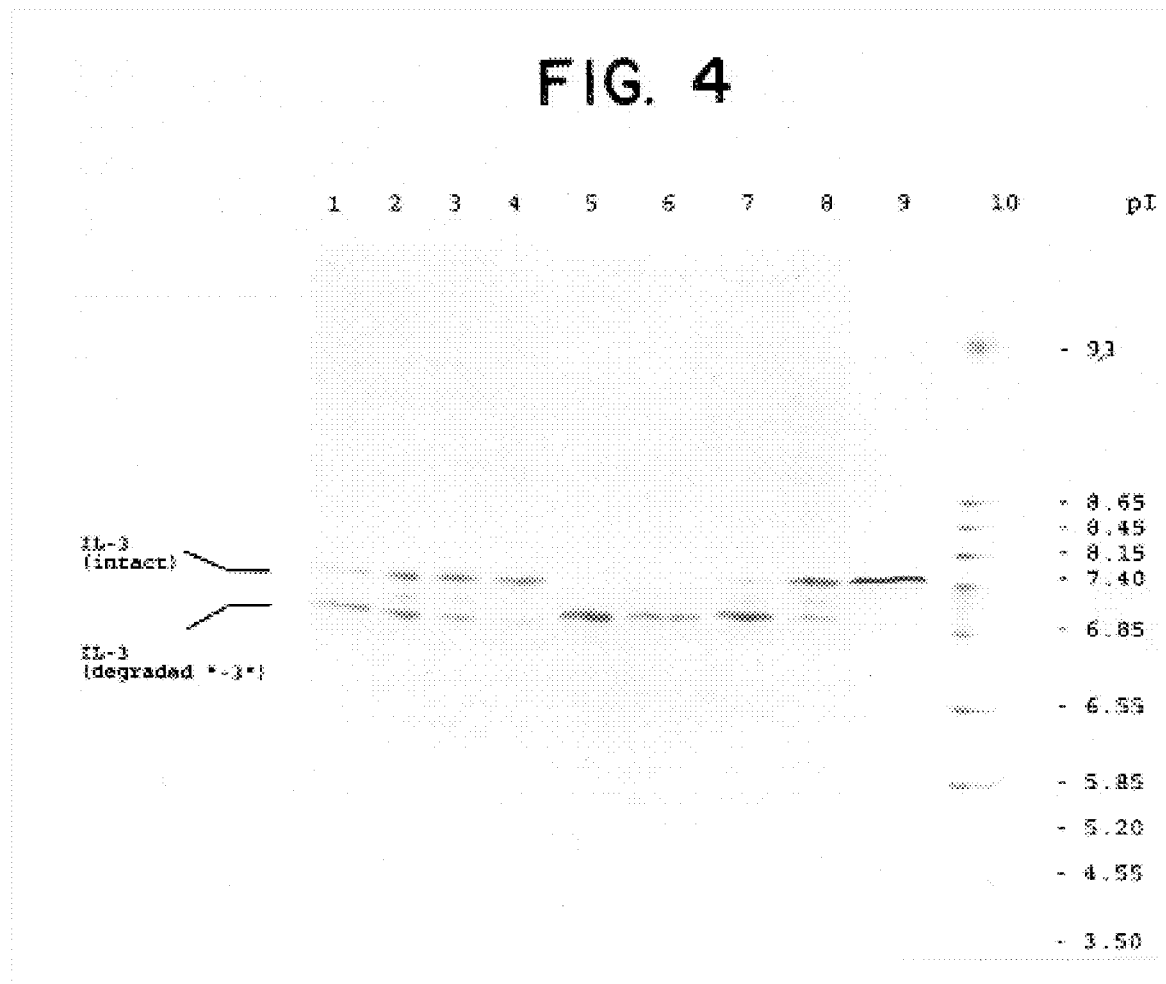

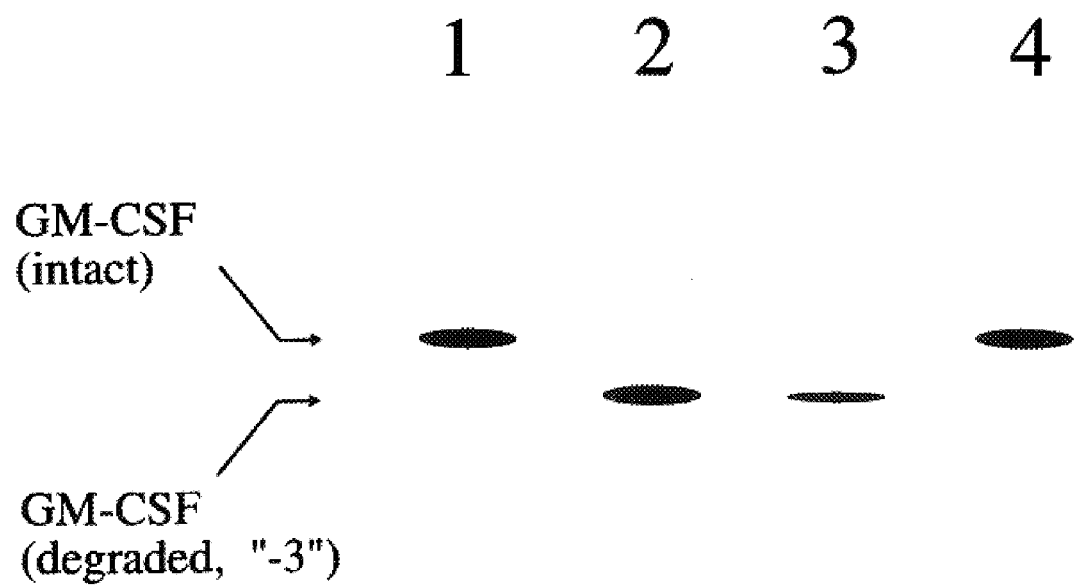

FIG. 12A

```
GGCGGGGACC GGCCGACGGC CCCGCCGAAC GAACGCCCTT CTCCGTTTAT CGGATTGGCA     60
AAGAAGTAGC ACTGGCCCTG TTCTCAGGAA ACCCACAGCG GCGAGGATCC CCGTACTTGT    120
CGCGAACACG TACGGGGAGG CCAC TTG AGG AAG AGC AGC ATA CGG CGG AGG      172
                           fMet Arg Lys Ser Ser Ile Arg Arg Arg
                                          -35

GCG ACC GCC TTC GGC ACG GCC GGA GCA CTG GTC ACC GCC ACG CTG ATC     220
Ala Thr Ala Phe Gly Thr Ala Gly Ala Leu Val Thr Ala Thr Leu Ile
-30             -25                 -20                 -15

GCC GGC GCC GTC TCG GCA CCC GCC GCG AGC GCC GCC CCG GCC GAC GGC     268
Ala Gly Ala Val Ser Ala Pro Ala Ala Ser Ala Ala Pro Ala Asp Gly
                -10                 -5                  1

CAC GGG CAC GGG CGG AGC TGG GAC CGG GAG GCG CGC GGT GCC GCC ATC     316
His Gly His Gly Arg Ser Trp Asp Arg Glu Ala Arg Gly Ala Ala Ile
        5                   10                  15

GCC GCC GCC CGC GCC GCC CGG GCG GGC ATC GAC TGG GAG GAC TGC GCA     364
Ala Ala Ala Arg Ala Ala Arg Ala Gly Ile Asp Trp Glu Asp Cys Ala
20                  25                  30

GCC GAC TGG AAC CTG CCC AAG CCC ATC CAG TGC GGC TAC GTC ACG GTG     412
Ala Asp Trp Asn Leu Pro Lys Pro Ile Gln Cys Gly Tyr Val Thr Val
35              40                  45                  50

CCG ATG GAC TAC GCC AAG CCG TAC GGC AAG CAG ATC AGG CTC GCC GTC     460
Pro Met Asp Tyr Ala Lys Pro Tyr Gly Lys Gln Ile Arg Leu Ala Val
            55                  60                  65

GAC CGC ATC GGC AAC ACC GGA ACC AGG AGC GAG CGC CAG GGC GCC CTG     508
Asp Arg Ile Gly Asn Thr Gly Thr Arg Ser Glu Arg Gln Gly Ala Leu
                70                  75                  80

ATC TAC AAC CCC GGC GGT CCC GGC GGC TCC GGC CTG CGT TTC CCG GCC     556
Ile Tyr Asn Pro Gly Gly Pro Gly Gly Ser Gly Leu Arg Phe Pro Ala
            85                  90                  95

CGC GTC ACG AAC AAG AGC GCG GTC TGG GCC AAC ACG GCC AAG GCC TAC     604
Arg Val Thr Asn Lys Ser Ala Val Trp Ala Asn Thr Ala Lys Ala Tyr
        100                 105                 110

GAC TTC GTC GGC TTC GAC CCG CGC GGC GTC GGC CAC TCC GCG CCC ATC     652
Asp Phe Val Gly Phe Asp Pro Arg Gly Val Gly His Ser Ala Pro Ile
115                 120                 125                 130

TCC TGC GTC GAC CCG CAG GAG TTC GTC AAG GCA CCC AAG GCC GAC CCC     700
Ser Cys Val Asp Pro Gln Glu Phe Val Lys Ala Pro Lys Ala Asp Pro
                135                 140                 145

GTG CCC GGC TCC GAG GCC GAC AAG CGC GCC CAG CGC AAG CTC GCC CGC     748
Val Pro Gly Ser Glu Ala Asp Lys Arg Ala Gln Arg Lys Leu Ala Arg
            150                 155                 160

GAG TAC GCC GAG GGC TGC TTC GAG CGC AGC GGC GAG ATG CTC CCG CAC     796
Glu Tyr Ala Glu Gly Cys Phe Glu Arg Ser Gly Glu Met Leu Pro His
        165                 170                 175
```

FIG. 12B

```
ATG ACC ACG CCG AAC ACC GCG CGC GAC CTC GAC GTC ATC CGC GCC GCC    844
Met Thr Thr Pro Asn Thr Ala Arg Asp Leu Asp Val Ile Arg Ala Ala
180             185                 190

CTC GGC GAG AAG AAG CTC AAC TAC CTC GGC GTC TCC TAC GGC ACC TAC    892
Leu Gly Glu Lys Lys Leu Asn Tyr Leu Gly Val Ser Tyr Gly Thr Tyr
195             200                 205                 210

CTC GGC GCC GTC TAC GGC ACC CTC TTC CCG GAC CAC GTC CGC CGC ATG    940
Leu Gly Ala Val Tyr Gly Thr Leu Phe Pro Asp His Val Arg Arg Met
            215                 220                 225

GTC GTC GAC AGC GTC GTC AAC CCG TCC CGC GAC AAG ATC TGG TAC CAG    988
Val Val Asp Ser Val Val Asn Pro Ser Arg Asp Lys Ile Trp Tyr Gln
                230                 235                 240

GCC AAC CTG GAC CAG GAC GTC GCC TTC GAG GGC CGC TGG AAG GAC TGG   1036
Ala Asn Leu Asp Gln Asp Val Ala Phe Glu Gly Arg Trp Lys Asp Trp
            245                 250                 255

CAG GAC TGG GTC GCC GCG AAC GAC GCC GCC TAC CAC CTC GGC GAC ACC   1084
Gln Asp Trp Val Ala Ala Asn Asp Ala Ala Tyr His Leu Gly Asp Thr
260                 265                 270

CGC GCC GAG GTC CAG GAC CAG TGG CTG AAG CTG CGC GCC GCC GCC GCG   1132
Arg Ala Glu Val Gln Asp Gln Trp Leu Lys Leu Arg Ala Ala Ala Ala
275                 280                 285                 290

AAG AAG CCG CTG GGC GGC GTC GTC GGA CCG GCC GAG CTG ATC TCC TTC   1180
Lys Lys Pro Leu Gly Gly Val Val Gly Pro Ala Glu Leu Ile Ser Phe
            295                 300                 305

TTC CAG AGC GCC CCG TAC TAC GAC TCC GCC TGG GCG CCG ACC GCG GAG   1228
Phe Gln Ser Ala Pro Tyr Tyr Asp Ser Ala Trp Ala Pro Thr Ala Glu
            310                 315                 320

ATC TTC AGC AAG TAC GTC GCC GGC GAC ACC CAG GCG CTC GTC GAC GCC   1276
Ile Phe Ser Lys Tyr Val Ala Gly Asp Thr Gln Ala Leu Val Asp Ala
            325                 330                 335

GCC GCA CCC GAC CTG TCC GAC ACC GCG GGC AAC GCC TCC GCG GAG AAC   1324
Ala Ala Pro Asp Leu Ser Asp Thr Ala Gly Asn Ala Ser Ala Glu Asn
            340                 345                 350

GGC AAC GCC GTC TAC ACG GCC GTC GAG TGC ACC GAC GCC AAG TGG CCC   1372
Gly Asn Ala Val Tyr Thr Ala Val Glu Cys Thr Asp Ala Lys Trp Pro
355                 360                 365                 370

GCC AAC TGG CGC ACC TGG GAC CGG GAC AAC ACC CGG CTC CAC CGC GAC   1420
Ala Asn Trp Arg Thr Trp Asp Arg Asp Asn Thr Arg Leu His Arg Asp
            375                 380                 385

CAC CCG TTC ATG ACC TGG GCC AAC GCC TGG ATG AAC CTG CCC TGT GCC   1468
His Pro Phe Met Thr Trp Ala Asn Ala Trp Met Asn Leu Pro Cys Ala
            390                 395                 400

ACC TGG CCG GTC AAG CAG CAG ACC CCG CTG AAC GTG AAG ACC GGC AAG   1516
Thr Trp Pro Val Lys Gln Gln Thr Pro Leu Asn Val Lys Thr Gly Lys
            405                 410                 415
```

FIG. 12C

```
GGA CTT CCG CCG GTG CTG ATC GTC CAG TCC GAG CGT GAC GCC GCC ACC      1564
Gly Leu Pro Pro Val Leu Ile Val Gln Ser Glu Arg Asp Ala Ala Thr
420                     425                     430

CCG TAC GAG GGC GCC GTC GAA CTG CAC CAG CGG TTC CGG GGA TCC CGC      1612
Pro Tyr Glu Gly Ala Val Glu Leu His Gln Arg Phe Arg Gly Ser Arg
435                     440                     445             450

CTG ATC ACC GAG CGG CGG GAC GCC GGC TCC CAC GGC GTC ACC GGC CTG GTC  1660
Leu Ile Thr Glu Arg Arg Asp Ala Gly Ser His Gly Val Thr Gly Leu Val
            455                     460                     465

AAC CCG TGC ATC AAC GAC CGG GTC GAC ACC TAC CTG CTC ACC GGC AGG      1708
Asn Pro Cys Ile Asn Asp Arg Val Asp Thr Tyr Leu Leu Thr Gly Arg
470                     475                     480

ACG GAC GCC CGC GAC GTG ACC TGC GCG CCG CAC GCC ACG CCC AGG CCG      1756
Thr Asp Ala Arg Asp Val Thr Cys Ala Pro His Ala Thr Pro Arg Pro
485                     490                     495             500

TAA CCCGGGCTCA GGCCAAGCGG GGGGAGGGGG CGACCGGTCC GACCGGCCGC           1809
End

CCCCTCCCCC CACCTGTCGC TACCGTCCCT CGGCCCAGGC GTCCTCCGCC GCGTAGTCGA    1869
AGAGGTCGCC GTACGCCTTG AACATCTTCG GGTAGGCCT                          1908
```

FIG. 13

```
Tap (199) K L N Y L G V S Y G T Y L G A V Y G T L F P D H V R R M V V(228)
                          *
HOHH (98) R V D L V G N S F G G A L S L A F A I R F P H R V R R L V L(127)
```

FIG. 20A

```
GGTACCAGGC GACGAAGGCG ACGGTCAGCG GGAACGCGAA GGAACGGAAG GAGCGGCGCA    60
GTTCGGCGAA CTCGGCGCTC TGCTGCACTT CGGAGAACTC CTCGGCGGAG GGGAGGCGGT   120
GCTCCTCTTG CGAGGGGGGC TCCTCTTTGG AGGGGGGCGG TGCGTCGGGT GGCCACGGAG   180
TCTCCTCGTA CGACGGACAT GACGGCTTGG ACCTCGGTGT TCTCGCAGGG GGCTGATCGT   240
GCTCGGGCTC CCTGTCCAAC GACACGGCGC CCCGCGGGGC CCGGTTCAAC ACCCGTGGCA   300
CTTTCCGAAG TCGTCCTCGG CGGGTCATTG CTGGCCAGGG ACTTCGGGGG ATAGCTTCAC   360
CCTGCACCAC TACGTCATGT ACCTGCCCGG CCCGTTTCAC CCGTGCCCGG GCAGGTGCTG   420
TTTGCCGGAT GATGTGGAGA CCCCATGGAT CATCTGCGCT TCCCGCGCGA CCCGCGCTCC   480
AGACGCGGGC TCGTTTCCCG AGCTTTCCCG ACGGACTGGA GACATCACGC ATG ACC      536
                                                        fMet Thr
```

| | | | | | | | | | | | | | | | | |
|---|---|---|---|---|---|---|---|---|---|---|---|---|---|---|---|---|
| GCT | CCC | CTC | TCG | CGT | CAC | CGC | CGT | GCC | CTC | GCG | ATT | CCG | GCG | GGC | CTG | 584 |
| Ala | Pro | Leu | Ser | Arg | His | Arg | Arg | Ala | Leu | Ala | Ile | Pro | Ala | Gly | Leu | |
| | | -120 | | | | -115 | | | | -110 | | | | | | |

| | | | | | | | | | | | | | | | | |
|---|---|---|---|---|---|---|---|---|---|---|---|---|---|---|---|---|
| GCC | GTG | GCC | GCG | TCG | CTC | GCG | TTC | CTG | CCG | GGC | ACC | CCG | GCC | GCC | GCG | 632 |
| Ala | Val | Ala | Ala | Ser | Leu | Ala | Phe | Leu | Pro | Gly | Thr | Pro | Ala | Ala | Ala | |
| | -105 | | | | -100 | | | | | -95 | | | | | | |

| | | | | | | | | | | | | | | | | |
|---|---|---|---|---|---|---|---|---|---|---|---|---|---|---|---|---|
| ACC | CCC | GCG | GCC | GAG | GCC | GCG | CCC | TCG | ACG | GCG | GCG | GAC | GCG | ACC | TCG | 680 |
| Thr | Pro | Ala | Ala | Glu | Ala | Ala | Pro | Ser | Thr | Ala | Ala | Asp | Ala | Thr | Ser | |
| -90 | | | | -85 | | | | | -80 | | | | | -75 | | |

| | | | | | | | | | | | | | | | | |
|---|---|---|---|---|---|---|---|---|---|---|---|---|---|---|---|---|
| CTC | AGC | TAC | GTC | GTC | AAC | GTC | GCC | TCC | GGG | CAC | CGT | CCT | TCG | GCC | ACC | 728 |
| Leu | Ser | Tyr | Val | Val | Asn | Val | Ala | Ser | Gly | His | Arg | Pro | Ser | Ala | Thr | |
| | | | | -70 | | | | | -65 | | | | | | -60 | |

| | | | | | | | | | | | | | | | | |
|---|---|---|---|---|---|---|---|---|---|---|---|---|---|---|---|---|
| GTG | CGG | CGG | GCG | ATA | GCC | AAG | GCG | GGC | GGC | ACG | ATC | GTC | ACG | TCG | TAC | 776 |
| Val | Arg | Arg | Ala | Ile | Ala | Lys | Ala | Gly | Gly | Thr | Ile | Val | Thr | Ser | Tyr | |
| | | | -55 | | | | | -50 | | | | | | -45 | | |

| | | | | | | | | | | | | | | | | |
|---|---|---|---|---|---|---|---|---|---|---|---|---|---|---|---|---|
| GAC | CGG | ATC | GGC | GTG | ATC | GTC | GTC | CAC | TCC | GCC | AAC | CCC | GAC | TTC | GCC | 824 |
| Asp | Arg | Ile | Gly | Val | Ile | Val | Val | His | Ser | Ala | Asn | Pro | Asp | Phe | Ala | |
| | | -40 | | | | | -35 | | | | | -30 | | | | |

| | | | | | | | | | | | | | | | | |
|---|---|---|---|---|---|---|---|---|---|---|---|---|---|---|---|---|
| AAG | ACC | GTG | CGC | AAG | GTG | CGC | GGC | GTG | CAG | TCG | GCC | GGT | GCC | ACC | CGC | 872 |
| Lys | Thr | Val | Arg | Lys | Val | Arg | Gly | Val | Gln | Ser | Ala | Gly | Ala | Thr | Arg | |
| | -25 | | | | | -20 | | | | | -15 | | | | | |

| | | | | | | | | | | | | | | | | |
|---|---|---|---|---|---|---|---|---|---|---|---|---|---|---|---|---|
| ACC | GCG | CCA | CTG | CCC | TCG | GCC | GCC | ACC | ACC | GAC | ACG | GGC | GCG | CCG | CAG | 920 |
| Thr | Ala | Pro | Leu | Pro | Ser | Ala | Ala | Thr | Thr | Asp | Thr | Gly | Ala | Pro | Gln | |
| -10 | | | | | -5 | | | | | 1 | | | | | 5 | |

| | | | | | | | | | | | | | | | | |
|---|---|---|---|---|---|---|---|---|---|---|---|---|---|---|---|---|
| GTG | CTC | GGC | GGC | GAG | GAC | CTG | GCC | GCC | GCC | AAG | GCC | GCC | TCC | GCG | AAG | 968 |
| Val | Leu | Gly | Gly | Glu | Asp | Leu | Ala | Ala | Ala | Lys | Ala | Ala | Ser | Ala | Lys | |
| | | | | 10 | | | | | 15 | | | | | 20 | | |

| | | | | | | | | | | | | | | | | |
|---|---|---|---|---|---|---|---|---|---|---|---|---|---|---|---|---|
| GCC | GAG | GGC | CAG | GAC | CCG | CTG | GAG | TCG | CTC | CAG | TGG | GAC | CTG | CCC | GCC | 1016 |
| Ala | Glu | Gly | Gln | Asp | Pro | Leu | Glu | Ser | Leu | Gln | Trp | Asp | Leu | Pro | Ala | |
| | | 25 | | | | 30 | | | | | 35 | | | | | |

FIG. 20B

```
ATC AAG GCG GAC AAG GCG CAC GAG AAG TCG CTG GGC AGC AGG AAG GTG    1064
Ile Lys Ala Asp Lys Ala His Glu Lys Ser Leu Gly Ser Arg Lys Val
        40                  45                  50

ACC GTC GCC GTC ATC GAC ACC GGC GTC GAC GAC ACC CAC CCG GAC ATC    1112
Thr Val Ala Val Ile Asp Thr Gly Val Asp Asp Thr His Pro Asp Ile
55                  60                  65                      70

GCC CCG AAC TTC GAC CGG CAG GCG TCC GTC AAC TGT GTG GCG GGC AAG    1160
Ala Pro Asn Phe Asp Arg Gln Ala Ser Val Asn Cys Val Ala Gly Lys
                    75                  80                  85

CCG GAC ACC GCC GAC GGG GCC TGG CGG CCG AGC GCG GCG GAG AGC CCG    1208
Pro Asp Thr Ala Asp Gly Ala Trp Arg Pro Ser Ala Ala Glu Ser Pro
                90                  95                  100

CAC GGC ACC CAC GTG GCC GGG GAG ATA GCC GCC GCC AAG AAC GGC GTC    1256
His Gly Thr His Val Ala Gly Glu Ile Ala Ala Ala Lys Asn Gly Val
            105                 110                 115

GGC ATG ACC GGC GTG GCA CCC GGG GTG AAG GTG GCC GGC ATC AAG GTC    1304
Gly Met Thr Gly Val Ala Pro Gly Val Lys Val Ala Gly Ile Lys Val
120                 125                 130

TCC AAC CCC GAC GGC TTC TTC TAC ACC GAG GCC GTG GTC TGC GGC TTC    1352
Ser Asn Pro Asp Gly Phe Phe Tyr Thr Glu Ala Val Val Cys Gly Phe
135                 140                 145                 150

ATG TGG GCG GCC GAG CAC GGC GTC GAC GTG ACC AAC AAC AGC TAT TAC    1400
Met Trp Ala Ala Glu His Gly Val Asp Val Thr Asn Asn Ser Tyr Tyr
                155                 160                 165

ACC GAC CCG TGG TAC TTC AAC TGC AAG GAC GAG CCC GAC CAG AAG GCG    1448
Thr Asp Pro Trp Tyr Phe Asn Cys Lys Asp Asp Pro Asp Gln Lys Ala
                170                 175                 180

CTC GTC GAG GCC GTC TCG CGG GCC TCC CGG TAC GCG GAG AAG AAG GGC    1496
Leu Val Glu Ala Val Ser Arg Ala Ser Arg Tyr Ala Glu Lys Lys Gly
            185                 190                 195

GCG GTC AAC GTC GCC GCG GCC GGC AAC GAG AAC TAC GAC CTC ACC TCC    1544
Ala Val Asn Val Ala Ala Ala Gly Asn Glu Asn Tyr Asp Leu Thr Ser
200                 205                 210

GAC GAG ATC ACC GAC CCG TCC TCG CCC AAC GAC ACC ACG CCC GGC GAC    1592
Asp Glu Ile Thr Asp Pro Ser Ser Pro Asn Asp Thr Thr Pro Gly Asp
215                 220                 225                 230
```

FIG. 20C

```
CGG ACC GTC GAC CCG TCG AAG TGC CTG GAC ATC CCG ACC CAG CTG CCG   1640
Arg Thr Val Asp Pro Ser Lys Cys Leu Asp Ile Pro Thr Gln Leu Pro
            235                 240                 245

GGT GTC GTG ACG GTC GCG GCG ACC GGT GCG AAG GGC CTC AAG TCG TCC   1688
Gly Val Val Thr Val Ala Ala Thr Gly Ala Lys Gly Leu Lys Ser Ser
            250                 255                 260

TTC TCC AAC CAC GGG CTG GGC GTC ATC GAC ATC GCC GCG CCC GGC GGC   1736
Phe Ser Asn His Gly Leu Gly Val Ile Asp Ile Ala Ala Pro Gly Gly
            265                 270                 275

GAC TCG ACG GCC TAC CAG ACC CCG GAG CCG CCC GCC ACG AGC GGC CTG   1784
Asp Ser Thr Ala Tyr Gln Thr Pro Glu Pro Pro Ala Thr Ser Gly Leu
            280                 285                 290

ATC CTG GGC ACG CTG CCC GGC GGC AAG TGG GGC TAC ATG GCC GGT ACG   1832
Ile Leu Gly Thr Leu Pro Gly Gly Lys Trp Gly Tyr Met Ala Gly Thr
295             300                 305                 310

TCC ATG GCC TCC CCG CAC GTC GCG GGC GTC GCC GCC CTC ATC AAG TCG   1880
Ser Met Ala Ser Pro His Val Ala Gly Val Ala Ala Leu Ile Lys Ser
                315                 320                 325

ACG CAC CCG CAC GCC TCC CCC GCC ATG GTG AAG GCG CTG CTG TAC GCC   1928
Thr His Pro His Ala Ser Pro Ala Met Val Lys Ala Leu Leu Tyr Ala
            330                 335                 340

GAG GCC GAC GCC ACG GCG TGC ACC AAG CCG TAC GAC ATC GAC GGC GAC   1976
Glu Ala Asp Ala Thr Ala Cys Thr Lys Pro Tyr Asp Ile Asp Gly Asp
            345                 350                 355

GGC AAG GTC GAC GCG GTG TGC GAG GGC CCG AAG AAC CGC AAC GGC TTC   2024
Gly Lys Val Asp Ala Val Cys Glu Gly Pro Lys Asn Arg Asn Gly Phe
            360                 365                 370

TAC GGC TGG GGC ATG GCC GAC GCG CTG GAC GCG GTG ACC TGG TAG CCGGT
Tyr Gly Trp Gly Met Ala Asp Ala Leu Asp Ala Val Thr Trp ter
375             380                 385

ACGCGTACCC GGTGCGTGAG GCGGGGGCGG CGGTCCGGTT CCCGTCCGGT CCGCCGCCCC   2074
CGTCGTCGTC GTCGTACGAC AGTATCTTCG CCATGGACAC TTACGAGGAT CC           2185
```

FIG. 21

```
          10v       20v       30v       40v       50v       60v
1  MTAPLSRHRRALAIPAGLAVAASLAFLPGTPAAATPAAEAAPSTAADATSLSYVVNVASGH
                                :...:       : A :
2                                           MRGKKVWISLLFALAL
                                                        10^

70v       80v       90v      100v      110v      120v
1  RPSATVRRAIAKAGGTIVTSYDRIGVIVVHSANPDFAKTVRKVRGVQSAGATRTAPLPSAA
    :  :  .: :  .::.   .: .:    V    ::  :.   A . :.V : :::  . :       .AA
2  IFTMAFGSTSSAQAAGKSNGEKKYIVGFKQTMSTMSAAKKKDVISEKGGKVQKQFKYVDAA
          20^       30^       40^       50^       60^       70^

130v      140v      150v      160v      170v      180v
1  TTDTGAPQVLGGEDLAAAKAASAKAEGQDPLESLQWDLPAIKADKAHEKSLGSRKVTVAVI
   ::.  ..  .V  . ..  ::.    ....   ::.   :S:...:::.IKA    H.::  ..:.:V.VAVI
2  SATLNEKAVKELKKDPSVAYVEEDHVAHAYAQSVPYGVSQIKAPALESQGYTGSNVKVAVI
          80^       90^      100^      110^      120^      130^

190v      200v      210v      220v      230v      240v
1  DTGVDDTHPDIAPNFDRQASVNCVAGKPDTADGAWRPSAAESPHGTHVAGEIAAAKNGVGM
   D:G:D.:HPD:                VAG :. .  :...P ..:::HGTHVAG.:AA :N::G:
2  DSGIDSSHPDL-----------KVAGGASMVPSETNPFQDNNSHGTHVAGTVAALNNSIGV
          140^                150^      160^      170^      180^

250v      260v      270v      280v      290v      300v
1  TGRWHPGVKVAGIKVSNPDGFFYTEAVVCGFMWAAEHGVDVTNNSYYTDPWYFNCKDDPDQ
      G      P:...:  ::KV  .:DG     . ::  G:  WA  .:.:DV.N  S   . :
2  LGV-APSASLYAVKVLGADGSGQYSWIINGIEWAIANNMDVTNMSLGGPSGS---------
          190^      200^      210^      220^      230^

310v      320v      330v      340v      350v      360v
1  KALVEAVSRASRYAEKKGAVNVAAAGNENYDLTSDEITDPSSPNDTTPGDRTVD-----PS
      AL   AV   A         G  V VAAAGNE          T  SS    PG
2  AALKAAVDKA---V-ASGVVVVAAAGNEG--------TSGSSSTVGYPG-KYPSVIAVGAV
          240^      250^      260^               270^      280^

370v      380v      390v      400v      410v      420v
1  KCLDIPTQLPGVVTVAATGAKGLKSSFSNHGLGVIDIAAPGGDSTAYQTPEPPATSGL-IL
                              F   G    D                            G: I
2  DSSN-------------------RASFSSVG-PELD----------------VMAPGVSIQ
          290^                         300^                    310^

430v      440v      450v      460v      470v      480v
1  GTLPGGKWGYMAGTSMASPHVAGVAALIKSTHPHASPAMVKALLYAEADATACTKPYDIDG
   :TLPG.K.G   .GTSMASPHVAG.AALI  S.HP: : :  V::  L ..:.   :      Y:` :
2  STLPGNKYGAYNGTSMASPHVAGAAALILSKHPNWTNTQVRSSLENTTTKLGDSFYYGKGL
          320^      330^      340^      350^      360^      370^

490v      500v      510v
1  DGKVDAVCEGPKNRNGFYGWGMADALDAVTW
    . .A.
2  INVQAAAQ
          380^
```

FIG. 25A

```
CCCGGGCCCG CGTCGGAGTC ATGACCGGTT GACGCCGTAA CACGTACGGG GCACGCGCAC  60
CACGCACCGC AACTGCTTCG TCGCGGAGAG TTACGCTCGC TGA ATG GAC ACA AGG   115
                                              Met Asp Thr Arg
                                                  -45
```

| | | | | | | | | | | | | | | | |
|---|---|---|---|---|---|---|---|---|---|---|---|---|---|---|---|
| CGC | ACT | CAC | CGC | AGG | ACC | CGC | ACC | GGC | GGC | ACC | CGT | TTC | CGG | GCC | ACG | 163 |
| Arg | Thr | His | Arg | Arg | Thr | Arg | Thr | Gly | Gly | Thr | Arg | Phe | Arg | Ala | Thr | |
| | | -40 | | | | -35 | | | | | | -30 | | | | |

| CTG | CTC | ACC | GCC | GCG | CTG | CTC | GCC | ACC | GCC | TGC | TCG | GCC | GGG | GGC | GCG | 211 |
| Leu | Leu | Thr | Ala | Ala | Leu | Leu | Ala | Thr | Ala | Cys | Ser | Ala | Gly | Gly | Ala | |
| | | -25 | | | | | -20 | | | | | -15 | | | | |

| TCG | ACG | TCC | GCC | GGA | TCC | CCC | GCG | GCC | AAG | GCG | GCC | GGC | GCG | ACG | GAG | 259 |
| Ser | Thr | Ser | Ala | Gly | Ser | Pro | Ala | Ala | Lys | Ala | Ala | Gly | Ala | Thr | Glu | |
| | -10 | | | | | -5 | | | | 1 | | | | | 5 | |

| GCG | GCC | ACG | GCG | ACC | CTG | ACC | CCC | CTG | CCG | AAG | GCC | ACG | CCC | GCC | GAG | 307 |
| Ala | Ala | Thr | Ala | Thr | Leu | Thr | Pro | Leu | Pro | Lys | Ala | Thr | Pro | Ala | Glu | |
| | | | | 10 | | | | | 15 | | | | | 20 | | |

| CTG | TCC | CCG | TAC | TAC | GAG | CAG | AAG | CTC | GGC | TGG | CGC | GAC | TGC | GGC | GTC | 355 |
| Leu | Ser | Pro | Tyr | Tyr | Glu | Gln | Lys | Leu | Gly | Trp | Arg | Asp | Cys | Gly | Val | |
| | | | 25 | | | | | 30 | | | | | 35 | | | |

| CCG | GGC | TTC | CAG | TGC | GCC | ACC | ATG | AAG | GCC | CCG | CTC | GAC | TAC | GCC | AAG | 403 |
| Pro | Gly | Phe | Gln | Cys | Ala | Thr | Met | Lys | Ala | Pro | Leu | Asp | Tyr | Ala | Lys | |
| | | 40 | | | | | 45 | | | | | 50 | | | | |

| CCC | GCC | GAC | GGC | GAC | GTC | CGG | CTC | GCG | GTG | GCC | CGC | AAG | AAG | GCC | ACG | 451 |
| Pro | Ala | Asp | Gly | Asp | Val | Arg | Leu | Ala | Val | Ala | Arg | Lys | Lys | Ala | Thr | |
| | 55 | | | | | 60 | | | | | 65 | | | | | |

| GGG | CCG | GGC | AAG | CGC | CTC | GGC | TCG | CTG | CTG | GTC | AAC | CCG | GGC | GGA | CCG | 499 |
| Gly | Pro | Gly | Lys | Arg | Leu | Gly | Ser | Leu | Leu | Val | Asn | Pro | Gly | Gly | Pro | |
| 70 | | | | | 75 | | | | | 80 | | | | | 85 | |

| GGC | GGC | TCG | GCG | ATC | GGC | TAC | CTC | CAG | CAG | TAC | GCG | GGC | ATC | GGC | TAC | 547 |
| Gly | Gly | Ser | Ala | Ile | Gly | Tyr | Leu | Gln | Gln | Tyr | Ala | Gly | Ile | Gly | Tyr | |
| | | | | 90 | | | | | 95 | | | | | 100 | | |

| CCG | GCG | AAG | GTC | CGC | GCC | CAG | TAC | GAC | ATG | GTG | GCG | GTC | GAC | CCC | CGG | 595 |
| Pro | Ala | Lys | Val | Arg | Ala | Gln | Tyr | Asp | Met | Val | Ala | Val | Asp | Pro | Arg | |
| | | | 105 | | | | | 110 | | | | | 115 | | | |

| GGC | GTG | GCC | CGC | AGT | GAA | CCC | GTC | GAG | TGC | CTG | GAC | GGG | CGC | GAG | ATG | 643 |
| Gly | Val | Ala | Arg | Ser | Glu | Pro | Val | Glu | Cys | Leu | Asp | Gly | Arg | Glu | Met | |
| | | 120 | | | | | 125 | | | | | 130 | | | | |

| GAC | GCG | TAC | ACG | CGC | ACC | GAC | GTC | ACC | CCG | GAC | GAC | GCG | GGC | GAG | ACG | 691 |
| Asp | Ala | Tyr | Thr | Arg | Thr | Asp | Val | Thr | Pro | Asp | Asp | Ala | Gly | Glu | Thr | |
| | 135 | | | | | 140 | | | | | 145 | | | | | |

FIG. 25B

```
GAC GAG CTG GTC GAC GCC TAC AAG GAG TTC GCC GAG GGC TGC GGG GCG    739
Asp Glu Leu Val Asp Ala Tyr Lys Glu Phe Ala Glu Gly Cys Gly Ala
150                 155                 160                 165

GAC GCG CCG AAG CTG CTG CGC CAC GTC TCC ACG GTC GAG GCG GCA CGC    787
Asp Ala Pro Lys Leu Leu Arg His Val Ser Thr Val Glu Ala Ala Arg
            170                 175                 180

GAC ATG GAC GTC CTG CGC GCG GTG CTG GGC GAC GAG AAG CTG ACC TAC    835
Asp Met Asp Val Leu Arg Ala Val Leu Gly Asp Glu Lys Leu Thr Tyr
        185                 190                 195

GTG GGA GCG TCG TAC GGC ACC TTC CTG GGC GCG ACC TAC GCC GGT CTG    883
Val Gly Ala Ser Tyr Gly Thr Phe Leu Gly Ala Thr Tyr Ala Gly Leu
            200                 205                 210

TTC CCC GAC CGG ACG GGC CGC CTG GTC CTG GAC GGC GCG ATG GAC CCC    931
Phe Pro Asp Arg Thr Gly Arg Leu Val Leu Asp Gly Ala Met Asp Pro
        215                 220                 225

TCG CTG CCC GCC CGC CGC CTG AAC CTG GAG CAG ACG GAG GGC TTC GAG    979
Ser Leu Pro Ala Arg Arg Leu Asn Leu Glu Gln Thr Glu Gly Phe Glu
230                 235                 240                 245

ACG GCG TTC CAG TCC TTC GCG AAG GAC TGC GTG AAG CAG CCG GAC TGC   1027
Thr Ala Phe Gln Ser Phe Ala Lys Asp Cys Val Lys Gln Pro Asp Cys
            250                 255                 260

CCC CTC GGC GAC AAG GAC ACC ACC CCC GAC CAG GTC GGC AAG AAC CTC   1075
Pro Leu Gly Asp Lys Asp Thr Thr Pro Asp Gln Val Gly Lys Asn Leu
        265                 270                 275

AAG TCC TTC TTC GAC GAC CTG GAC GCG AAG CCC CTG CCC GCC GGC GAC   1123
Lys Ser Phe Phe Asp Asp Leu Asp Ala Lys Pro Leu Pro Ala Gly Asp
            280                 285                 290

GCC GAC GGC CGC AAG CTC ACC GAA TCC CTC GCC ACC ACC GGC GTG ATC   1171
Ala Asp Gly Arg Lys Leu Thr Glu Ser Leu Ala Thr Thr Gly Val Ile
295                 300                 305

GCC GCG ATG TAC GAC GAG GGC GCC TGG CAG CAG CTG CGC GAG TCC CTC   1219
Ala Ala Met Tyr Asp Glu Gly Ala Trp Gln Gln Leu Arg Glu Ser Leu
310                 315                 320                 325

ACC TCG GCG ATC AAG GAG AAG GAC GGT GCG GGC CTG CTG ATC CTC TCC   1267
Thr Ser Ala Ile Lys Glu Lys Asp Gly Ala Gly Leu Leu Ile Leu Ser
            330                 335                 340

GAC AGC TAC TAC GAG CGC GAG GCC GAC GGC GGC TAC AGC AAC CTG ATG   1315
Asp Ser Tyr Tyr Glu Arg Glu Ala Asp Gly Gly Tyr Ser Asn Leu Met
        345                 350                 355
```

FIG. 25C

```
TTC GCC AAC GCC GCC GTG AAC TGC CTC GAC CTC CCC GCC GCC TTC TCC    1363
Phe Ala Asn Ala Ala Val Asn Cys Leu Asp Leu Pro Ala Ala Phe Ser
        360                 365                 370

TCC CCG GAC GAG GTG CGC GAC GCC CTC CCC GAC TTC GAG AAG GCG TCC    1411
Ser Pro Asp Glu Val Arg Asp Ala Leu Pro Asp Phe Glu Lys Ala Ser
        375                 380                 385

CCG GTC TTC GGC GAG GGC CTC GCC TGG TCC TCC CTG AAC TGC GCG TAC    1459
Pro Val Phe Gly Glu Gly Leu Ala Trp Ser Ser Leu Asn Cys Ala Tyr
390                 395                 400                 405

TGG CCG GTG AAG CCC ACG GGG GAG CCG CAC CGC ATC GAG GCG GCC GGC    1507
Trp Pro Val Lys Pro Thr Gly Glu Pro His Arg Ile Glu Ala Ala Gly
                410                 415                 420

GCC ACC CCG ATC GTC GTG GTC GGC ACC ACC CGC GAC CCG GCC ACC CCC    1555
Ala Thr Pro Ile Val Val Val Gly Thr Thr Arg Asp Pro Ala Thr Pro
                425                 430                 435

TAC CGC TGG GCC GAG GCC CTC TCC GAC CAG CTC ACC TCC GGC CAC CTC    1603
Tyr Arg Trp Ala Glu Ala Leu Ser Asp Gln Leu Thr Ser Gly His Leu
        440                 445                 450

CTC ACC TAC GAG GGA GAC GGC CAC ACC GCG TAC GGC CGC GGC AGC TCC    1651
Leu Thr Tyr Glu Gly Asp Gly His Thr Ala Tyr Gly Arg Gly Ser Ser
        455                 460                 465

TGC ATC GAC TCC GCG ATC AAC ACG TAC CTG CTG ACC GGC ACC GCC CCG    1699
Cys Ile Asp Ser Ala Ile Asn Thr Tyr Leu Leu Thr Gly Thr Ala Pro
470                 475                 480                 485

GAG GAC GGC AAG CGC TGC TCG TAA CCCCC GCCTGCCCGC CCCGGGACCC ACGCCTCCGG  1758
Glu Asp Gly Lys Arg Cys Ser ter
                490
GGGCGGGTTC GGAGCACCCC GGGAAACTGT GTAGACTTGC CGACGTTGCT GATCGCACCA TGG    1821
```

```
GGTACCGGCG GCCAAGACCG TGTGCTCCTG ACCGCGGACG CCACCACAGG TCGGCAGAAG        60
CAGCAGATCG ACAGAAGTAG CAGGTCAGAG CGTTATCCAC AGGCGTCGGC GGGTGCTGCC       120
CCCGCCACCT ACCATGGCAG GAACGCCATC CGCCGCACGG CGCGGACGGC TTGCCAGGGG       180
GGAGAGGAC ATG GCG CGT CTC GTC CGG TGG ACG GCT CTG ACG GCC GCC GCC GCA  234
          fMet Ala Arg Leu Val Arg Trp Thr Ala Leu Thr Ala Ala Ala Ala
                         5                  10                      15

CTG CTG ACG GCG GGC TGC AGC GGC GGC TCG TCC GAC GAG GAC AAG GAC        282
Leu Leu Thr Ala Gly Cys Ser Gly Gly Ser Ser Asp Glu Asp Lys Asp
             20              25                  30

GAC GGG GGC AGG AGC AGC GCG GGA CCT TCG GCG GCG GCA CCC TCC GGG        330
Asp Gly Gly Arg Ser Ser Ala Gly Pro Ser Ala Ala Ala Pro Ser Gly
             35              40                  45

GTG CCG GAG GCA CTG GCG TCC CAG ACG CTG GAC TGG GCC CGA TGC GAG        378
Val Pro Glu Ala Leu Ala Ser Gln Thr Leu Asp Trp Ala Arg Cys Glu
             50              55                  60

GGC AGC GAC GAT GCC CCG GCG CCG GAC GGC GAC TGG CGG TGC GCC ACG        426
Gly Ser Asp Asp Ala Pro Ala Pro Asp Gly Asp Trp Arg Cys Ala Thr
         65              70                  75

CTG AAG GCA CCG CTG GAC TGG TCC GAC CCC GAC GGC GAG ACG ATC GAT        474
Leu Lys Ala Pro Leu Asp Trp Ser Asp Pro Asp Gly Glu Thr Ile Asp
 80              85                  90                      95

CTC GCG CTG ATC CGG TCC CGG GCG AGC GGG GAC GAC CGC ATC GGC TCC        522
Leu Ala Leu Ile Arg Ser Arg Ala Ser Gly Asp Asp Arg Ile Gly Ser
                 100             105                 110

CTG CTG TTC AAC TTC GGC GGC CCG GGC GCC TCC GGC GTC TCC ACG ATG        570
Leu Leu Phe Asn Phe Gly Gly Pro Gly Ala Ser Gly Val Ser Thr Met
             115             120                 125

CCG TCC TAC GCC GAC ACC GTC TCC TCC CTG CAC GAG CGG TAC GAC CTG        618
Pro Ser Tyr Ala Asp Thr Val Ser Ser Leu His Glu Arg Tyr Asp Leu
         130             135                 140

GTG AGC TGG GAC CCG CGC GGG GTG GCC GCC AGC GAG GGC GTC CGC TGC        666
Val Ser Trp Asp Pro Arg Gly Val Ala Ala Ser Glu Gly Val Arg Cys
 145             150                 155

CGC ACC GAC GAG GCG ATC GAG GCC GCC GAG TCG GTG GAC TCC ACG CCG        714
Arg Thr Asp Glu Ala Ile Glu Ala Ala Glu Ser Val Asp Ser Thr Pro
 160             165                 170                 175

GAC TCC CCG GCC GAG GAG CAG GCC TAC CTG AAG GAC GCC GCC GAC TTC        762
Asp Ser Pro Ala Glu Glu Gln Ala Tyr Leu Lys Asp Ala Ala Asp Phe
         180             185                 190
```

FIG. 29B

| | |
|---|---|
| GGC AGG GGC TGC GAG AAG GCC GCC GGC AAG CTC ATG GAA CAC GTC TCG<br>Gly Arg Gly Cys Glu Lys Ala Ala Gly Lys Leu Met Glu His Val Ser<br>          195                        200                  205 | 810 |
| ACC ACG GAC ACG GCC CGC GAC ATG GAC CTG ATG CGG CAC GTC CTG GGC<br>Thr Thr Asp Thr Ala Arg Asp Met Asp Leu Met Arg His Val Leu Gly<br>          210                        215                  220 | 858 |
| GAC GAG AGG ATG CAC TAC TTC GGC ATC TCC TAC GGC ACC GAA CTC GGC<br>Asp Glu Arg Met His Tyr Phe Gly Ile Ser Tyr Gly Thr Glu Leu Gly<br>          225                        230                  235 | 906 |
| GGC GTC TAC GCC CAT CTG TTC CCC GAG CAC GTG GGC CGC GTG ATC CTC<br>Gly Val Tyr Ala His Leu Phe Pro Glu His Val Gly Arg Val Ile Leu<br>240                          245                    250                  255 | 954 |
| GAC GCG GTG GTG GAC CCG GGC GCC GAC ACG ATG GGC CAC GCC GAG AAC<br>Asp Ala Val Val Asp Pro Gly Ala Asp Thr Met Gly His Ala Glu Asn<br>                        260                    265                  270 | 1002 |
| CAG GCC AGG GGT TTC CAG CGC GCG CTG GAC GAC TAC CTG GAG TCG ACC<br>Gln Ala Arg Gly Phe Gln Arg Ala Leu Asp Asp Tyr Leu Glu Ser Thr<br>          275                        280                  285 | 1050 |
| GGC CAG GAA CCC GAA CAG GGG TCG CGG AAG ATC GCC GGC CTG CTG GAG<br>Gly Gln Glu Pro Glu Gln Gly Ser Arg Lys Ile Ala Gly Leu Leu Glu<br>          290                        295                  300 | 1098 |
| CGG CTG GAC GCC GAG CCA CTG CCC ACG TCC TCG CCG GGG CGG GAG CTG<br>Arg Leu Asp Ala Glu Pro Leu Pro Thr Ser Ser Pro Gly Arg Glu Leu<br>          305                        310                  315 | 1146 |
| ACG CAG ACC CTC GCG TTC ACC GGC ATC GTG CTG CCG CTG TAC AGC GAG<br>Thr Gln Thr Leu Ala Phe Thr Gly Ile Val Leu Pro Leu Tyr Ser Glu<br>320                        325                    330                  335 | 1194 |
| AGC GGC TGG CCG GCC CTG ACC AGT GCG CTG AAG GCG GCC GAG GAG GGC<br>Ser Gly Trp Pro Ala Leu Thr Ser Ala Leu Lys Ala Ala Glu Glu Gly<br>                    340                    345                  350 | 1242 |
| GAC GGC TCG GAG TTG CTG GCC CTC GCC GAC GGC TAC AAC GAG CGT GAT<br>Asp Gly Ser Glu Leu Leu Ala Leu Ala Asp Gly Tyr Asn Glu Arg Asp<br>          355                        360                  365 | 1290 |
| CCC TCG GGG CGC TAC GGC ACG ACG ACC CAC TCG CAA AGG GTC ATA TCG<br>Pro Ser Gly Arg Tyr Gly Thr Thr Thr His Ser Gln Arg Val Ile Ser<br>          370                        375                  380 | 1338 |
| TCG CTG GAC GAC AAG CAG AGG CCG ACC GTG GAG GAG ACG AAG AAG CTG<br>Cys Leu Asp Asp Lys Gln Arg Pro Thr Val Glu Glu Thr Lys Lys Leu<br>385                        390                    395 | 1386 |

FIG. 29C

```
CTG CCG AGG TTC GAG AAG GTC TCT CCC GTC TTC GGC GCC TTC CTC GGC    1434
Leu Pro Arg Phe Glu Lys Val Ser Pro Val Phe Gly Ala Phe Leu Gly
400                 405                 410                 415

TGG GAC ACG GCC GGG TGC TGC CAC GAC TGG CAC GGT CAG CAC            1482
Trp Asp Thr Ala Gly Cys Trp Asp His Pro Val Ala Gly Gln His
        420                 425                 430

GAG ACC GCG GTG GAG AGC GTG GAC CCC GCC GAC GCC CCG GTC GTG GTC    1530
Glu Thr Ala Glu Val Ser Ala Pro Ala Ala Pro Val Leu Val Val
    435                 440                 445

GGC AAC ACG GGC GAC CCG GCC ACG TAC GAG GGC GCC CGC AGG ATG        1578
Gly Asn Thr Gly Asp Pro Ala Thr Tyr Glu Gly Ala Arg Arg Met
    450                 455                 460

GCG GAC GAG CTG GGC AAG GAC GTC GGC GTG GTG CTG ACC TGG CAG GGC    1626
Ala Asp Glu Leu Gly Lys Asp Val Gly Val Val Leu Thr Trp Gln Gly
465                 470                 475

GAG GGA CAC GGT GCC TAC GGG AAC GGA AGC GAC TGT GTC GAC TCC GCG    1674
Glu Gly His Gly Ala Tyr Gly Asn Gly Ser Asp Cys Val Asp Ser Ala
480                 485                 490                 495

GTG GAC GCC TAC CTG TTG AAG GGG ACG GTG CCG AAG GAC GGC AAG GTC    1722
Val Asp Ala Tyr Leu Leu Lys Gly Thr Val Pro Lys Asp Gly Lys Val
    500                 505                 510

TGC TCA TGA CGGCGGCGGG GGCTTCGGGC ACCTGCGGTG CGGGAAACCC CCGCCG     1771
Cys Ser End
```

METHOD FOR EXPRESSION OF PROTEINS IN BACTERIAL HOST CELLS

This application is a continuation-in-part of U.S. application Ser. No. 08/265,310, filed Jun. 24, 1994, now U.S. Pat. No. 5,856,166, which is a continuation-in-part of U.S. application Ser. No. 08/173,508, filed Dec. 23, 1993, now U.S. Pat. No. 5,616,485, both of which are herein incorporated by reference.

FIELD OF THE INVENTION

This invention relates generally to proteases produced by Streptomyces which degrade products expressed in genetically-engineered Streptomyces as hosts, inhibitors of such proteases, improved hosts with impaired protease systems, hosts selected for high expression of such proteases and the use of such proteases, inhibitors and improved hosts.

BACKGROUND OF THE INVENTION

Production methods employing recombinant technology use genetic expression systems. These systems generally consist of host cells encompassing a genetic system to be expressed, and expression vectors which introduce the genetic expression capabilities into the host cells. Under conditions allowing expression, a product, generally a protein, is made by the host cells.

Problems in commercial use of genetic expression systems arise because host cells have a variety of endogenous proteases, each with a specific action that may degrade the product. Degradation of product may also decrease the shelf lives of the bulk protein product and of the final dosage form of drugs.

Endogenous proteases degrade substrates in different ways. Aminopeptidases have broad substrate specificity, e.g., leucine aminopeptidase (Hanson and Frohne, 1976). However, when a proline residue is reached during degradation, such enzymes are unable to further degrade the peptide. Aminopeptidase P enzymes hydrolyse aminoacyl-proline bonds when proline is in the penultimate position from the amino terminus (X-Pro) of a polypeptide (Yoshimoto et al., 1988). After that action, proline aminopeptidase is capable of removing the exposed amino terminal proline residue.

Dipeptidyl peptidases have been found in many eukaryotic species (Kreil, 1990), but only in a few prokaryotic species (Lloyd et al., 1991; Fukusawa and Harada, 1981). These enzymes can remove N-terminal dipeptides including X-Pro dipeptides.

Tripeptidyl aminopeptidases are capable of degrading a peptide or polypeptide at its amino terminus by removing an amino acid triplet. Serine proteases from human, rat and pig tissues with tripeptidyl aminopeptidase activity have been characterized (McDonald et al., 1985, Balon et al., 1986), and a cDNA sequence has been reported (Tomkinson and Jonsson, 1991).

Various bacteria are known in the art to secrete proteases. For example, Bacillus PB92 produces a protease that degrades casein and a tripeptide substrate (z-Gly-Pro-citrulline-PNA). Roig et al., Appl. Biochem. Biotechnol. 55:95 (1995). A serine exopeptidease that cleaves Leu or Phe from tripeptide substrates has been characterized in Bacillus. Sharipova et al. Biotechnol. 94—Ferment. Physiol. pages 31–33 (1994). B. licheniformis produces a serine protease that is inhibited by PMSF. Pavlova et al. Mikrobiologiya 57:398 (1988). See also Balaban et al. Biokhimiya 59(9):1393 (1994). Lactobacillus helveticus produces a prolyl dipeptidyl aminopeptidase, a di/tripeptidase, and other dipeptidases. Nowokokski et al. Appl. Microbiol. Biotechnol. 39(2):204 (1993). Lactococcus lactis produces a tripeptidase with specificity for, inter alia, (Leu)$_3$ and Leu-Gly-Gly. EP 440 303 (Bosman et al.; publication date Aug. 7, 1991). Salmonella typhimurium produces a tripeptidase. Strauch et al. J. Bacteriol. 156:743 (1983).

Endoproteases can also cause rapid degradation of secreted proteins. Serine proteases are widespread throughout the prokaryotes as are metalloproteases. A wide variety of cleavage site specificities have been observed in various microbial species. Enzymes which cleave adjacent to positively charged, negatively charged, and aromatic amino acids have all been reported.

Proteases may be neutralized by various methods including by using inhibitors and by constructing improved strains with impaired proteases. The use of protease inhibitors to prevent the degradation of proteins during their purification is well established for proteins derived from yeast and higher eukaryotes. This approach has also been employed in the isolation and purification of proteins generated as inclusion bodies from E. coli. The general method involves lysing the protein source in the presence of broad spectrum protease inhibitors. Such inhibitors may include leupeptin, EDTA, phenylmethanesulfonylfluoride, or pepstatin.

The application of protease inhibitors in a system involving a living organism is more delicate. EDTA increases the fragility of many microorganisms and can cause cell lysis. Some inhibitors may be taken up by the organism. Such a process may lead to cell death or a disruption of cellular functions. Ideally, a protease inhibitor employed under these conditions should 1) be soluble in the fermentation media, 2) inhibit the target protease as selectively as possible, 3) not inhibit cell growth, and 4) be cost-effective.

The use of improved strains with impaired proteases also can prevent degradation of proteins during production. Improved strains carrying deletional mutations in multiple protease-encoding genes have been made in Bacillus strains (Sloma et al, 1992). International Application Number PCT/US92/01598 of Omnigene, Inc. describes a Bacillus cell containing a mutation in the residual protease III gene resulting in the inhibition of the production by the cell of proteolytically active RP-III. In that case, the inactivation of the major protease allowed detection of other minor proteases which were still present in quantities sufficient to cause degradation of secreted products.

International Application Number PCT/US92/05532 of Amgen Inc. entitled "Isolation and Characterization of a Novel Protease from Streptomyces lividans" describes a protease called "Protease X" of S. lividans, its DNA and amino acid sequence, antibodies raised against such protease and a strain of S. lividans deficient in such protease. Protease X has different DNA and amino acid sequences than the proteases described in this application and cleaves different substrates than those described in this application.

A specific recombinant genetic expression system designated CANGENUS™ has been used to ferment and produce a variety of protein products, for example, granulocyte macrophage-colony stimulating factor (GM-CSF), interleukin-3 (IL-3), interleukin-6 (IL-6), and erythropoietin (EPO) (see Canadian Patent Numbers 1,295,563; 1,295,566; and 1,295,567; and U.S. Pat. No. 5,200,327).

Although the CANGENUS™ system has been successful in producing exogenous products, some undesirable proteases produced by expression of endogenous genes deleteriously affect the quality, quantity or stability of exogenous products.

Thus, a need exists to impair the action of these Streptomyces proteases. Among strategies which can be employed to meet this need are the use of inhibitors to inhibit the effect of proteases during the production processes and the use of improved strains which lack such proteases or which have impaired proteases.

Isolation of the protease genes could also be useful in the design of vectors directing the expression and secretion of heterologous proteins from Streptomyces. The promoter and signal sequence of such proteases could be used to enhance and direct the export of heterologous proteins from Streptomyces. The proteases themselves could be usefully employed to remove specific amino acid sequences, peptides or polypeptides from a protein. Furthermore, it would be useful if the level of expression of such proteases could be enhanced through mutation, selection or genetic engineering.

SUMMARY OF THE INVENTION

Streptomyces strains secrete a wide variety of heterologous proteins including GM-CSF, IL-3, IL-6, EPO, TNF, SCF, IL-7 and IL-2. These strains are useful in production of these proteins as desired products of commercial manufacturing systems. However, proteases of such Streptomyces strains impair the quality and quantity of secreted proteins. Before this invention, attempts to improve the quality and quantity of such proteins were not successful. This invention meets that goal by (A) inhibiting certain Streptomyces proteases, and (B) providing new Streptomyces strains which lack or have impaired degradative proteases.

To circumvent protein degradation, this invention uses selective inhibitors which are capable of protecting secreted peptides, and polypeptides including heterologous protein biopharmaceuticals from degradation by secreted host proteases. This invention encompasses the use of such selective inhibitors for production of heterologous proteins in any bacterial host, including, but not limited to Streptomyces, Eschericia, Bacillus, and Pseudomonas.

This invention also uses improved strains that have impaired protease production systems, yet which are capable of expressing desired products.

This invention relates to the selection of Streptomyces strains with enhanced expression of proteases and the isolation and purification of Streptomyces proteases. An embodiment of a protease is a tripeptidyl aminopeptidase designated Tap. Amino acid sequences of the proteases and substantially equivalent sequences are aspects of the present invention. Promoters and signal sequences of such proteases are further aspects of the present invention.

A signal sequence is typically composed of the amino-terminal portion of the unprocessed polypeptide, extending from the amino terminal residue to the beginning of the mature protein sequence. The signal sequence is typically a small peptide which directs the protein to a particular cellular or extracellular location, or for export from the cell, at which point the signal peptide is preferably cleaved.

This invention also relates to nucleotide sequences encoding impaired proteases and the use of those sequences to increase the quality, quantity or stability of peptides and polypeptides including heterologous proteins secreted from a host transformed with a vector containing the nucleotide sequence for such impaired proteases.

This invention also relates to the use of the isolated and purified proteases to cleave peptides or polypeptides or to cleave amino acids, peptides or polypeptides from a protein.

A further aspect of this invention is the construction of an inhibitor comprising, L-alanyl-L-prolyl-L-alanine chloromethylketone (APACMK), its salts and analogs. Another aspect of this invention is the use of the inhibitor L-alanyl-L-prolyl-L-alanine chloromethylketone to inhibit a tripeptidyl aminopeptidase derived from Streptomyces.

This invention also relates to a method of increasing the quality, quantity or stability of peptides or polypeptides including heterologous proteins secreted from a host by using an inhibitor comprising L-alanyl-L-prolyl-L-alanine chloromethylketone.

The invention further relates to a method for the production of a heterologous protein, comprising:
 (a) providing a bacterial host cell transformed with a nucleic acid expression construct that comprises a nucleic acid sequence encoding said heterologous protein; and
 (b) incubating said host cell in the presence of an aminopeptidase inhibitor.

Other embodiments of the claimed invention relate to the above-described method, wherein said inhibitor is a tripeptidyl aminopeptidase inhibitor, or a peptide-substituted chloromethylketone.

The invention further relates to a method for the production of a heterologous protein, comprising:
 (a) providing a Streptomyces host cell transformed with a nucleic acid expression construct that comprises a nucleic acid sequence encoding said heterologous protein; and
 (b) incubating said host cell in the presence of an aminopeptidase inhibitor.

Other embodiments of the claimed invention relate to the above-described methods, wherein said inhibitor is a tripeptidyl aminopeptidase inhibitor, or a peptide-substituted chloromethylketone.

In a further embodiment, the invention relates to the above-described methods for producing heterolgous protein, wherein said inhibitor has the structure: X-Proline-Y-chloromethylketone, where X denotes an aliphatic or hydroxy amino acid and Y denotes an aliphatic, hydroxy, or sulfur-containing amino acid.

In yet another embodiment, the invention relates to the above-described methods for producing heterolgous protein, wherein said inhibitor has the structure: X-Proline-Y-chloromethylketone, where X and Y denote non-polar amino acids.

In another embodiment, the invention relates to the above-described methods for producing heterolgous protein, wherein said inhibitor is selected from the group consisting of APA-chloromethylketone, APM-chloromethylketone, APS-chloromethylketone, GPL-chloromethylketone, SPA-chloromethylketone, and APF-chloromethylketone.

Another aspect of the invention relates to the above-described method for producing heterolgous protein, wherein said heterologous protein is selected from the group consisting of GM-CSF, IL-3, IL-6, EPO, SCF, IL-7, and IL-2. In further aspect of the invention relates to the above-described method for producing heterologous protein, wherein said heterologous protein is secreted from said Streptomyces host cell. The Streptomyces host cell employed with the above-described method may be any wild-type Streptomuces that is suitable for expression of heterologous protein. alsternatively, the host cell may be a Streptymyces strain having impaired expression of at least one endogenous protease, such as a tripeptidyl aminopeptidase. Similarly, other bacterial expression hosts are employed, such as *E. coli, Bacillus subtilis, B. brevis*, and Pseudomonas.

Thus, another aspect of this invention is the construction of an improved Streptomyces strain having impaired expression of at least one endogenous protease. The strain is capable of expressing an exogenous gene product *S. lividans, S. ambofaciens, S. coelicolor, S. alboniger, S. fradiae, S. griseus, S. parvulus* and *S. rimosus*. The impaired expression decreases the activity or quantity of endogenous protease resulting in an increase in quality, quantity or stability of exogenous gene product.

Impaired expression is accomplished by deleting or mutating one or more nucleotides in the sequence encoding for a protease, or by deleting and substituting nucleotides in the sequence encoding for a protease.

A further aspect of this invention is a vector which has a recombinant DNA sequence encoding a Streptomyces protease or an impaired Streptomyces protease and a regulatory sequence for expression of the coding sequence. The regulatory sequence includes a promoter sequence, an operator sequence, a transcriptional-start sequence, a ribosome-binding site sequence, and a signal sequence.

Another aspect of this invention is a method of fermentation using genetically engineered Streptomyces host cells with impaired protease activity, The method includes the steps of: (a) constructing Streptomyces host cells with impaired protease activity and which express a desired exogenous product under suitable conditions; and (b) placing the cells in suitable conditions for expression of the desired product. The method of fermentation can be used to express GM-CSF, IL-3, IL-6, EPO, TNF, SCF, IL-7 and IL-2 or any other desired product.

In another aspect, this invention envisions introducing the DNA sequences encoding such proteases into recombinant vectors which, when transformed into suitable host strains, enable the production of heterologous proteases having the biological activity of the wild type proteases. Both prokaryotic and eucaryotic hosts may serve as hosts for producing such proteases.

Further aspects of this invention are kits containing (a) isolated and purified proteases derived from Streptomyces, or (b) inhibitors of proteases derived from Streptomyces.

A kit for ELISA would consist of:

1) A protease, Tap, covalently linked to biotin or other carrier capable of participating in the formation of an antigen-antibody complex (example: Tap covalently linked to a goat antirabbit IgG);

2) A substrate, APA-pNA or APA-AMC, which would be cleaved by the Tap bound in the antigen-antibody complex thereby generating an increase in light absorbance at 405 nm with APA-pNA as substrate or an increase in fluorescence when an excitation/emission near 380/460 nm is employed with APA-AMC as substrate.

The present invention describes a method for improving the secretion of mature protein from a genetic expression system. The levels of secreted proteins that are increased are those that have amino terminal structures that interfere with the processing of the signal peptide (structural constraints). Secretion of heterologous proteins by a genetic expression system is improved by adding tripeptides (propeptides) to the amino terminal end of the protein which is a precursor to the desired product of the system, the addition occurring immediately adjacent to the signal peptidase cleavage site, allowing the cleavage to occur to form a mature protein, and then removing the tripeptide from the mature protein by use of a protease such as Tap.

The invention also relates various new protease such as SlpD and SlpE that are useful to attach polypeptides to bacteria during processing.

In this application, the following terms have the following meanings:

"Heterologous" or "exogenous" refers to nucleic acids, amino acids, peptides, polypeptides or proteins which do not naturally occur in a particular host cell.

"Host cell" means a prokaryotic or eucaryotic cell, strain, species or genera, suitable for introduction and for expression of heterologous DNA sequences. Such DNA sequences may be modified for expression in a particular host as a DNA sequence containing (i) codons preferably used by the host, or (2) promoters, operators, ribosome binding sites and terminator sequences used by the host.

"Substantially equivalent" in reference to a sequence means a sequence, whether natural or engineered, which has additions, deletions, or substitutions compared to the sequence of another protease described or claimed in this application and which produces a functionally similar protease to the protease described or claimed.

"Wild type" means the activity characteristic of a host cell in which endogenous proteases are not impaired. Illustrative embodiments of impaired proteases include a host strain in which DNA at the chromosomal locus encoding a protease in a Streptomyces strain is deleted. This strain exhibits a significantly reduced level of activity or no activity when compared to a wild type Streptomyces strain.

"Impaired" means that the activity and/or the quantity of protease produced by a nucleotide sequence is impaired compared to a "wild type" nucleotide sequence, that is, a sequence not altered to affect expression as it generally occurs in the host species and strain.

"Endogenous protease" means a protease that is able to cleave one or more of the substrates referred to in this application.

"Selective inhibitor" means an inhibitory molecule that inhibits a secreted protease, or a protease released into the fermentation as a result of cell breakage.

| ABBREVIATIONS | |
|---|---|
| –3 | protein from which three amino acid residues have been removed from the N-terminus of the protein |
| –4 | protein from which four amino acid residues have been removed from the N-terminus of the protein |
| –6 | protein from which six amino acid residues have been removed from the N-terminus of the protein |
| aa | amino acid |
| AAPA-pNA | L-alanyl-L-alanyl-L-prolyl-L-analine p-nitroanilide |
| AA-pNA | L-alanyl-L-alanine p-nitroanilide |
| AMC | 7-amino-4-methylcoumarin |
| APACMK | L-alanyl-L-prolyl-L-alanine chloromethylketone |
| APA-AMC | L-alanyl-L-prolyl-L-alanine 7-amino-4-methylcoumarin |
| APF-bNA | L-alanyl-L-prolyl-L-phenylalanine beta-naphthylamide |
| APA-pNA | L-alanyl-L-prolyl-L-alanine p-nitroanilide |
| APM-pNA | L-alanyl-L-prolyl-L-methionine p-nitroanilide |
| A-pNA | L-alanine p-nitroanilide |
| APS-bNA | L-alanyl-L-prolyl-L-serine beta-naphthylamide |
| bNA | beta-naphthylamide |
| Boc | N-t-butoxycarbonyl |

-continued

ABBREVIATIONS

| | |
|---|---|
| Boc-AAPA-pNA | N-t-butoxycarbonyl L-alanyl-L-alanyl-L-prolyl-L-alanine p-nitroanilide |
| Boc-APARSPA-bNA | L-alanyl-L-prolyl-L-analyl-L-arginyl-L-seryl-L-prolyl-L-alanine beta-napthylamide |
| D-FPR-bNA | D-phenylalanyl-L-prolyl-L-arginine beta-napthylamide |
| DMSO | dimethyl sulphoxide |
| D-PFR-pNA | D-prolyl-L-phenylalanyl-L-arginine p-nitroanilide |
| EDTA | Ethylenediaminetetraacetic acid |
| ELISA | enzyme-linked immunosorbent-assay |
| FPLC | fast protein liquid chromatography |
| GPL-bNA | Glycyl-L-prolyl-L-leucine beta-napthylamide |
| GP-pNA | Glycyl-L-proline p-nitroanilide |
| GPM | Glycly-L-prolyl-L-methionine |
| HEPES | N-2-hydroxyethylpiperazine-N'-2-ethanesulphonic acid |
| HOHD | 2-hydroxy-6-oxohepta-2,4-dienoate |
| L-pNA | L-leucine p-nitroanilide |
| MNNG | N-methyl-N'-nitro-N-nitrosoguanidine |
| N-Ac | N-acetyl |
| N-Ac-APA-pNA | N-acetyl-L-alanyl-L-prolyl-L-alanine p-nitroanilide |
| N Bz | N-benzoyl |
| N Bz-R-pNA | N-benzoyl-L-arginine |
| N Bz-VGR-pNA | N-benzoyl-L-alanyl-glycyl-L-arginine p-nitroanilide |
| nt | nucleotide |
| ORF | open reading frame |
| PAGE | polyacrylamide gel electrophoresis |
| PMSF | phenylmethanesulfonyl fluoride |
| pNA | p-nitroaniline |
| P-pNA | L-proline p-nitroanilide |
| R-pNA | L-arginine p-nitroanilide |
| SDS | sodium dodecyl sulphate |
| S-bNA | L-serine beta-napthylamide |
| SPA-bNA | L-seryl-L-prolyl-L-alanine beta-napthylamide |
| Ssp | Streptomyces Subtilisin-like protein |
| ssp | gene encoding Ssp |
| Tap | tripeptidyl aminopeptidase-S |
| tap | gene encoding Tap |
| TSB | Trypticase Soya Broth |

DESCRIPTION OF DRAWINGS

FIGS. 3A–3B. Demonstration of purification of Tap.

FIG. 4. Inhibition of IL-3 cleavage by Tap after PMSF treatment.

FIG. 8. (B) The tap-deletion clones.

FIG. 8. (C) The tap-integration clones.

FIG. 11. Conversion of the substrate of intact GM-CSF to its "-3 form" upon incubation with fermentation culture supernatants from cells carrying the tap clones.

FIGS. 12A–12C. Nucleic acid (SEQ ID NO:1) and encoded amino acid (SEQ ID NO:2) sequences of the tripeptidyl aminopeptidase (tap) gene.

FIG. 13. Amino acid sequence similarity between Tap (amino acids 199–228 of SEQ ID NO:2) and HOHD (amino acids 98–127 of SEQ ID NO:11) from *Pseudomonas putida* F1.

FIGS. 20A–20C. Nucleic acid (SEQ ID NO:3) and encoded amino acid (SEQ ID NO:4) sequences of the cloned P5-4 DNA.

FIG. 21. Comparison of the predicted amino acid sequence encoded by the P5-4 (SEQ ID NO:4) DNA and that of subtilisin BPN (SEQ ID NO:12).

FIGS. 25A–25C. Nucleic acid (SEQ ID NO:7) and predicted amino acid (SEQ ID NO:8) sequence of P5-6 DNA.

FIG. 26. Comparison of the predicted amino acid sequences for the Tap (SEQ ID NO:2) and P5-6-encoded putative protein.

FIGS. 29A–29C. Nucleic acid (SEQ ID NO:5) and predicted amino acid (SEQ ID NO:6) sequence of P8-2.

FIGS. 32A–32C. Demonstration of the use of Tap in ELISA technology by standard calibration curve in hIL-3.

DETAILED DESCRIPTION OF PREFERRED EMBODIMENTS

Figure 1A:
FIGS. 1A–1B. Degradation of GM-CSF and IL-3 by *S. lividans* fermentation broth.

A previously unknown protease, a tripeptidyl aminopeptidase ("Tap") derived from Streptomyces, has been identified, isolated, and characterized. The enzyme was purified by pH precipitation and chromatography. The proteolytic activity was followed both by assaying the degradation of GM-CSF and by the release of the yellow p-nitroaniline molecule from the specially synthesized substrate L-alanyl-L-prolyl-L-aniline p-nitroanilide (APA-pNA). The pure protease had an apparent molecular weight of 55,000 daltons as determined by SDS-PAGE. The amino terminal sequence of the purified protease was determined by Edman degradation of the protein after purification.

Chloromethylketones (CMK) are known to provide selective inhibition of some proteases. The earliest studied chloromethylketones, tosyllsine chloromethylketone (TLCK) and tosylphenylalanine chloromethylketone (TPCK), selectively inhibit trypsin and chymotrypsin, respectively (Schoellman et al., 1963, Shaw et al., 1965). Longer peptide sequences are needed for the inhibition of certain proteases and improve the specificity of the inhibition in some cases.

Based on the substrate specificity of Tap, a selective inhibitor of Tap, L-alanyl-L-prolyl-L-alanine chloromethylketone (APACMK), has been designed, synthesized, and applied to inhibit this protease. APACMK stopped the release of p-nitroaniline from APAPNA by Tap. APACMK stopped the cleavage of GM-CSF by Tap. In fermentations of GM-CSF, APACMK prevented cleavage of GM-CSF by Tap during fermentation but did not significantly retard the rate of cell growth.

Other suitable aminopeptidase for the production of heterologous protein are based on the substrate specificity of Tap, and include, but are not limited to APA-chloromethylketone, APM-chloromethylketone, APS-chloromethylketone, GPL-chloromethylketone, and SPA-chloromethylketone, APF-chloromethylketone.

Other suitable inhibitors have the structure X-Proline-Y-chloromethylketone, where X denotes an aliphatic or hydroxy amino acid and Y denotes an aliphatic, hydroxy, or sulfur-containing amino acid. The skilled artisan will recognize that glycine (G), alanine (A), valine (V), leucine (L), and isoleucine (I) are classified as aliphatic amino acids. The skilled artisan also will recognize that hydroxy amino acids are serine (S) and threonine (T). Sulfur-containing amino acids are methionine (M) and cysteine (C).

Still other inhibitors have the structure: X-Proline-Y-chloromethylketone, where X and Y denote non-polar amino acids. The skilled artisan will recognize that non-polar amino acids include Alanine (A), Valine (V), Leucine (L), Isoleucine (I), Proline (P), Phenylalanine (F), Tryptophan (W) and Methionine (M).

Therefore, the invention relates to a method for the production of a heterologous protein, comprising:

(a) providing a bacterial host cell transformed with a nucleic acid expression construct that comprises a nucleic acid sequence encoding said heterologous protein; and (b) incubating said host cell in the presence of an aminopeptidase inhibitor.

Suitable host cells for such a method includes, but are not limited to, Streptomyces, Bacillus, Pseudomonas and Escherichia.

The invention also relates to a method for the production of a heterologous protein, comprising:

(a) providing a Streptomyces host cell transformed with a nucleic acid expression construct that comprises a nucleic acid sequence encoding said heterologous protein; and (b) incubating said host cell in the presence of an aminopeptidase inhibitor.

Including a suitable aminopeptidase inhibitor the methods of the invention will increase the yield and integrity of the expressed heterologous protein. In particular, including the inhibitor will prevent aminopeptidase-catalyzed degradation of heterologous protein.

Any of the above-described peptide-CMK protease inhibitors are suitable for use in the methods of the invention. The skilled artisan will recognize that selection of a particular aminopeptidase inhibitor will vary according to the nature of the expressed heterologous protein. In general, the tripeptide in the aminopeptidase inhibitor will be the same as the N-terminal tripeptide in the heterologous protein. For example, APACMK prevented degradation of human GM-CSF, and the N-terminal sequence of human GM-CSF is A-P-A. See Example 9.

Although it is preferred to use an aminopeptidase inhibitor with a tripeptide sequence that is the same as the N-terminal tripeptide of the heterologous protein produced, chloromethylketones with tripeptide terminals that are different to the N-terminal tripeptide of a particular heterologous protein will also inhibit the aminopeptidase (bind the active site) and minimize protein degradation. The inhibitory potencies of the aminopeptidase inhibitors with different tripeptide terminal are directly proportional to the affinity of the enzyme for the particular tripeptide substrate as described in Tables III, IV and V. For example, a GPL-chloromethylketone inhibits aminopeptidase and minimizes GM-CSF degradation but the IC50 of GPL-chloromethylketone is higher than APA-chloromethylketone (i.e. a higher concentration of GPL-CMK is required to achieve the same extent (50%) of inhibition as APA-CMK). Determination of the appropriate concentration of the aminopeptidase inhibitor will vary with experimental conditions and is a matter of routine optimization.

Other embodiments of the claimed invention relate to the above-described methods, wherein said inhibitor is a tripeptidyl aminopeptidase inhibitor, or a peptide-substituted chloromethylketone.

Any heterologous protein may be produced according the inventive method. Suitable proteins include, but are not limited to, GM-CSF, IL-3, IL-6, EPO, SCF, IL-7, and IL-2. When a peptide-substituted chloromethylketone is used to inhibit aminopeptidase activity, it will be most advantageous to use a substituted CMK having the same peptide as the N-terminal peptide as that in the heterologous protein. A further aspect of the invention relates to the above-described method for producing heterologous protein, wherein said heterologous protein is secreted from said Streptomyces host cell.

Techniques for transformation of Streptymyces with a nucleic acid expression construct are well known in the art. Furthermore, the skilled artisan will be aware that many art-recognized vectors are suitable for the expression of such constructs in Streptomyces. For example, see U.S. Pat. No. 5,200,327, hereby incorporated by reference. Techniques for expressing and secreting heterologous protein from Streptomyces are also well known in the art. See U.S. Pat. No. 5,200,327. The skilled artisan will recognize that Streptomyces bacterium has been used successfully to express homologous and heterologous proteins. See Tomich, et al. *Genet. Eng.* (N.Y.) 12: 53 (1990), Hopwood, D. A. *Prospects*

*Ind. Appl. Genet. Eng.* 73–85 (1983), Anne, et al. *FEMS-Microbiol. Lett.* 114: 121 (1993), and Fornwold, et al. *Bio/Technology* 11: 1031 (1993), hereby incorporated by reference. See also Perez, et al. *Gene* 123: 109 (1993); Tsao, et al. *Biochim. Biophys. Acta-N* 1171: 255 (1993); Gusek, et al. *Critical Rev. Microbiol.* 18: 247 (1992); Wallace, et al. *Frontiers Bioprocess II.* 168 (1992); ; Bibb, M. J., et al. *Biol. Biochem. Biomed. Aspects-Actinomycetes* 32: 25 (1986); U.S. Pat. No. 5,192,669; U.S. Pat. No. 5,063,158; European Patent No. 475195; PCT Patent Application WO 91/10739.

Briefly, a construct comprising a promoter, operably linked to a signal sequence functional in Streptymyces, which is in turn operably linked to a gene encoding a heterologous protein, is expressed in a Streptomyces host. Suitable promoter sequences include, but are not limited to, the promoter from the aminoglycoside phosphotransferase gene. Suitable signal sequences, include, but are not limited to, the signal sequences from *S. griseus* protease B, *S. plicatus* endo-B-N-acetylglucosaminidase H, the signal sequence from any other protein that is secreted by Streptomyces, or a hybrid of any of such signal sequences.

Any Streptomyces host cell that is suitable for expression of heterolgous protein may be used in the above-described method for production of heterolgous protein. Wild-type Streptomyces strains, such as *S. lividans* 66, may be used. In addition, a Streptomyces strain, having impaired expression of a tripeptidyl aminopeptidase, may be used. Procedures for construction of strains with such impaired proteases are described in Examples 14 and 16. Impairment of proteases may be accomplished using art-recognized techniques, such as deletional gene inactivation via homologous recombination and chemical mutagenesis.

The skilled artisan will recognize that techniques for transforming other bacterial host cells, and expressing heterolgous proteins from such cells, are well known in the art. Thus, techniques for expressing proteins in Bacillus brevis are described in Udaka, et al. *Biotechnol. Genet. Eng. Rev.* 7:113 (1989). Techniques for Bacillus expression are also described in McConnell et al. *Ann. N.Y. Acad. Sci.* 469:1 (1986), Chater et al. *Trends-Biochem. Sci.* 7(12):445 (1982) and Dubnau, D. *Microbiol. Rev.* 55(3):395 (1991) and Errington et al. *Protein Prod. Biotechnol.* pp1–14 (1990). Additionally, techniques for expressing proteins in *E. coli* are described in Somerville, R. L. *Biotechnol. Genet. Eng. Rev.* 6:1 (1988), Yarranton et al. *Genetic Transform. and Express.* pp 409–416 (1989), Glick J. *Ind. Microbiol.* 1(5) :277 (1987), Hsiung, H. M. *Biotechnol. Adv.* 4(1):1 (1986), Bevan, E. A. *Indian J. Pharm. Sci.* 44:41 (1982). Finally techniques for expressing proteins in Pseudomonas are described in U.S. Pat. No. 4,680,260.

A tripeptidyl aminopeptidase gene (tap) was cloned from *S. lividans* 66 by screening for overexpression of endogenous enzyme activity using the chromogenic substrate GPL-bNA as a liquid overlayer on colonies of Streptomyces growing on agar medium. When these colonies were selected on the basis of activity they exhibited according to the chromogenic assay disclosed herein, and were grown in liquid culture, a major secreted protein with an estimated apparent molecular weight of 55,000 daltons as determined by SDS-PAGE was identified in the culture supernatant. The appearance of this protein was correlated with elevated levels of Tap activity in liquid assays using GPL-bNA and other substrates, suggesting that Tap presence was causative of the activity detected by the assay.

The amino terminal sequence of the overexpressed protein was determined by various procedures, e.g., by Edman degradation of the protein after purification by SDS-PAGE. The amino terminal sequence of the overexpressed protein matched the amino terminal sequence of Tap isolated from fermentations of the host strain. The tap gene was localized within the cloned DNA fragment by monitoring the Tap activity of strains containing various subclones and deletion clones derived from the original clones.

DNA sequences adjacent to the tap gene were used to construct a subclone in which the tap gene was precisely deleted. This deletion clone was then substituted into the chromosomes of *S. lividans* 66 strains by homologous recombination to replace the wild type tap locus with a mutant gene which encoded a defective Tap.

Disruption of the chromosomal tap gene in *S. lividans* resulted in a reduction in Tap activity of at least tenfold, indicating that this enzyme was responsible for the majority of the activity observed in *S. lividans* strains. Deletional inactivation of the gene encoding a second protease (Ssp) resulted in a further reduction in the ability of cell-free broth to hydrolyse APA-bNA. Strains carrying such chromosomal DNA deletions generally exhibited significantly lower Tap activity (FIG. 22), reducing the degradation of proteins produced by genetically engineered host cells, and enabling higher recovery of secreted proteins from the culture supernatant produced by fermentation of the host strain in liquid medium.

I. Prokaryotic Tripeptidyl Aminopeptidases

Tripeptidyl Aminopeptidase

Degradation products were found in fermentations producing GM-CSF and IL-3.

Figure 1B:

FIGS. 1A–1B shows the degradation products derived from GM-CSF and IL-3. (A) shows a native gel electrophoresis analysis of GM-CSF degradation. Lane 1 shows intact, full length GM-CSF. Lane 2 shows GM-CSF from *S. lividans* fermentation. Lane 3 shows degraded isolated GM-CSF(-3). Lane 4 shows a mixture of isolated GM-CSF (-4) and GM-CSF(-6). (B) shows an analysis of IL-3 degradation by electrophoresis on an SDS-urea gel (6M urea in the polyacrylamide gel). A 20-fold concentrated fermentation broth was prepared by subjecting a cell-free fermentation broth to ultrafiltration employing a membrane with a 10 kDa cutoff. Lane 1 shows IL-3 before incubation. Lane 2 shows IL-3 after 2 hours incubation at 32° C.

The major degradation products were isolated and analyzed by amino acid sequencing. This analysis indicated that the major degradation products (FIG. 1A, Lane 3 and FIG. 4, Lane 5) were produced by the removal of the N-terminal tripeptides, APA and APM, from GM-CSF and IL-3, respectively.

Based upon this information, the molecule APA-pNA was synthesized as a potential substrate. This and several commercial substrates were employed in a survey of proteolytic activities in *S. lividans* fermentation broths.

Figure 2:
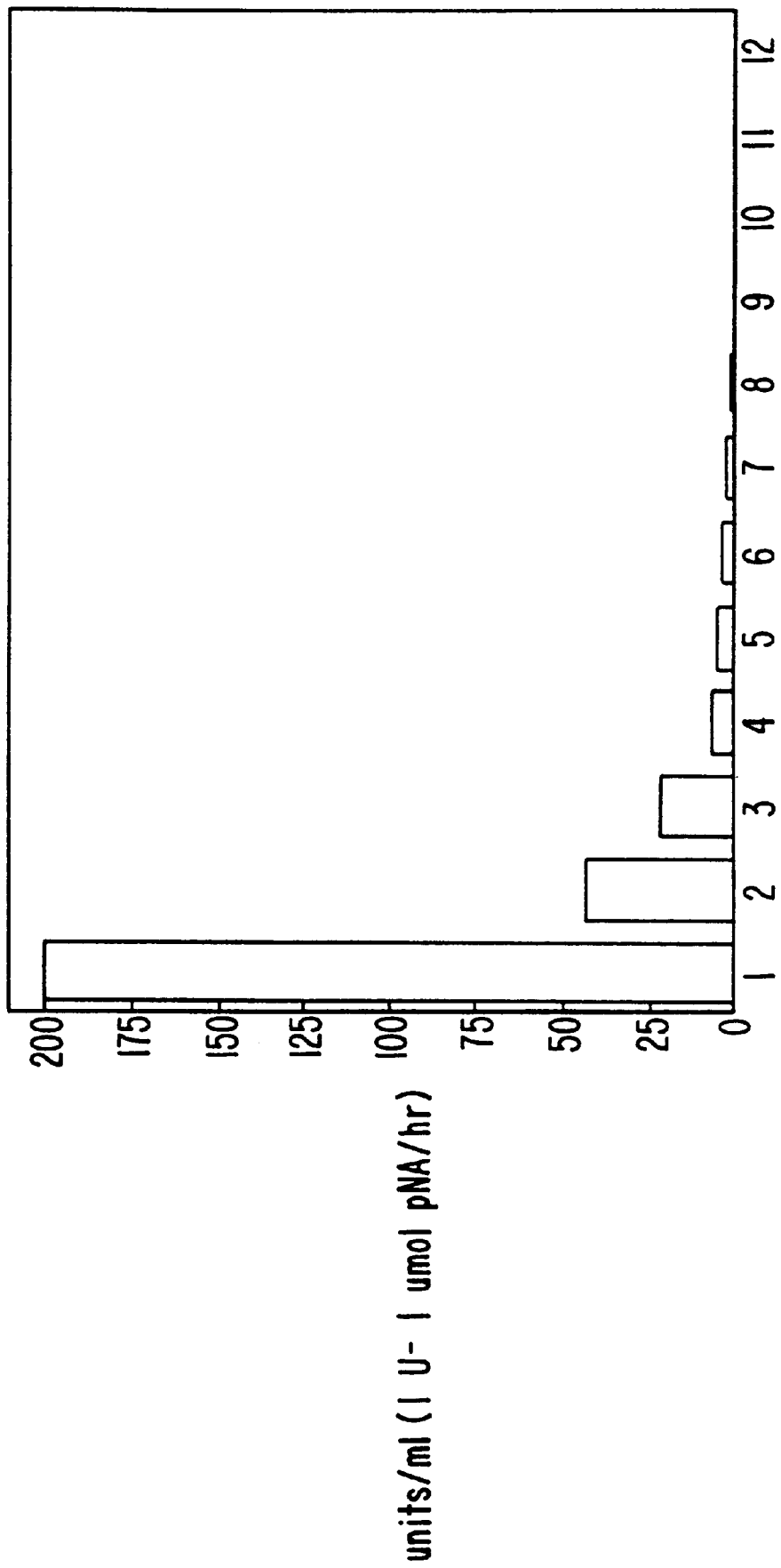
FIG. 2. Cleavage of synthetic substrates by *S. lividans* fermentation broth.

FIG. 2 is the quantification of proteolytic activities in the fermentation broth as measured with synthetic substrates. The assays were conducted in 50 mM Tris-HCl, pH 8.0 with 0.8 mM substrate incubated at 37° C. The change in absorbance at 405 nm was measured after 1, 2, and 4 hours of incubation. The results are reported as micromoles of p-nitroaniline released in 1 hour by 1.0 ml of fermentation broth. 1=APA-pNA; 2=D-PFR-pNA; 3=L-pNA; 4=R-pNA; 5=P-pNA; 6=AP-pNA; 7=A-pNA; 8=AA-pNA; 9=N-Benzoyl-R-pNA; 10=Boc-AAPA-pNA; 11=N-Acetyl-APA-pNA; 12=N-Benzoyl-Y-pNA.

As shown in FIG. 2, APA-pNA cleaving activity was greater than any other activity measured in the broth. This data suggested that a single protease, a tripeptidyl peptidase, not a group of several enzymes, was responsible for the activity. Additionally, the lack of activity towards the amino-blocked analog, N-Ac-APA-pNA, indicated that the enzyme responsible was an aminopeptidase.

The wild-type protease was purified after cell removal and concentration of the fermentation broth by ultrafiltration. The method of purification is described in Example 1. To purify Tap (FIGS. 3A–3B), approximately 20 ug of protein were denatured under reducing conditions and analyzed by SDS-PAGE on 10% polyacrylamide gel. (A) represents purification of wild-type Tap. St=Molecular weight standards; Lane 1=Broth obtained after cell removal and concentration of broth by ultrafiltration through a 10 kDa membrane; Lane 2=Redissolved pH 4.0 precipitate; Lane 3=Q-Sepharose chromatography pool; Lane 4=Phenyl-Sepharose chromatography pool. (B) represents purified Tap from the overproducer strain. St=Molecular weight standards; Lane 1=Tap purified from fermentation of the over-expressor (P3-5) strain.

The pure protease cleaved the N-terminal tripeptide from GM-CSF and cleaved the N-terminal tripeptide from IL-3. When GM-CSF or IL-3 were used as a substrate, the cleaved products produced by the pure Tap were identical to the major degradation products found in Streptomyces fermentations. These assays are described in Example 2.

As described in Example 2, Tap releases p-nitroaniline from APApNA. The enzyme was also active when APM-pNA, APA-AMC, APS-bNA, GPL-bNA, and SPA-bNA were used as substrates. It did not release the reporter group from A-pNA, L-pNA, P-pNA, R-pNA, S-bNA, N-Bz-R-pNA, AA-pNA, GP-pNA, D-PFR-pNA, N-Ac-APA-pNA, N-Bz-VGR-pNA, AAPA-pNA, Boc-AAPA-pNA, and Boc-APARSPA-bNA. The enzyme only released the reporter group from substrates with a free amino terminal. The enzyme cleaved only tripeptide units since no reporter release was seen with mono-, di-, or tetra-amino acid substrates.

The effect of pH on the activity of Tap has been examined. When APA-pNA was used as a substrate, the enzyme was active from between pH 5.0–9.5 with the maximal activity obtained from between 8.0–8.5. The enzyme cleaved GM-CSF from between pH 4.0–10.0 with greatest activity from between 5.0–9.0. The broad maximum for GM-CSF reflected the high sensitivity of this substrate to Tap. The enzyme cleaved IL-3 from between pH 5.0–9.0 with maximal activity attained between 7.0 and 8.5.

An inhibitor survey indicated that tripeptidyl aminopeptidase was a serine protease. Table I shows the inhibition of Tap activity by various protease inhibitors. The protease and inhibitor were preincubated for 15 minutes at 22° C. Substrate was added and the mixture was incubated at 37° C. Activity was measured by monitoring the change in absorbance at λ=405 nm.

TABLE I

Inhibition of TAP in the APA-pNA Assay

| Sample | Concentration | Residual Activity |
|---|---|---|
| Enzyme only | — | 100 |
| PMSF | 1.6 mM | 7 |
| HgCl$_1$ | 0.1 mM | 99 |
|  | 1.0 mM | 93 |
| CaCl$_2$ | 1.0 mM | 96 |
|  | 10 mM | 97 |
| CoCl$_2$ | 1.0 mM | 98 |
|  | 10 mM | 97 |
| EDTA | 1.0 mM | 95 |
|  | 10 mM | 95 |

TABLE I-continued

Inhibition of TAP in the APA-pNA Assay

| Sample | Concentration | Residual Activity |
|---|---|---|
| IDA | 1.0 mM | 82 |
| DTT | 1 mM | 86 |
| DTT + EDTA | 1 mM + 10 mM (respectively) | 97 |
| Elastatinal | 0.1 mM | 97 |
| Chymostatin | 0.1 mM | 98 |
| Pepstatin | 0.1 mM | 95 |
| Benzamidine | 10 mM | 94 |

The enzyme was inhibited by the serine protease inhibitor, phenylmethanesulfonyl fluoride (PMSF). Treatment of Tap with PMSF inhibited cleavage of GM-CSF, IL-3, and APA-pNA.

The inhibition of IL-3 cleavage is demonstrated in FIG. 4 and the inactivation protocol is described in Example 3. Lanes 1–4 show the incubation of IL-3 with TAP-S that has been treated with PMSF. Lane 1=4 hrs; Lane 2=2 hours; Lane 3=1 hr.; Lane 4=0 hours. Lanes 5–8 show the incubation of IL-3 with uninhibited Tap. Lane 5=4 hrs.; Lane 6=2 hrs.; Lane 7=1 hrs.; Lane 8=0 hrs. Lane 9 is a human carbonic anhydrase marker, pI=7.4. Lane 10 contains pI markers. As can be seen in Lanes 5–8 of FIG. 4, the IL-3 (pI=7.4) is completely converted to the -3 form (pI=7.1) by Tap within 2 hours. Lanes 1–4 show that with PMSF treatment, intact IL-3 is clearly detected after 4 hours. The enzyme is not affected by sulfhydryl reagents, chelators or aspartyl protease inhibitors (Table I).

Table II shows the N-terminal sequence of the isolated wild-type Tap. The sequence data was obtained as described in Example 4.

TABLE II

N-Terminal Sequence of Isolated Tap

| Cycle | Amino Acid, Wild-Type |
|---|---|
| 1 | Asp |
| 2 | Gly |
| 3 | His |
| 4 | Gly |
| 5 | His |
| 6 | Gly |
| 7 | Arg |
| 8 | Ser |
| 9 | Trp |
| 10 | Asp |
| 11 | Arg |
| 12 | Glu |
| 13 | Ala |
| 14 | Arg |
| 15 | Gly |

II. L-Alanyl-L-Prolyl-L-Alanine Chloromethylketone (APACMK)

The synthesis of APACMK is described in Example 5.

Figure 5:
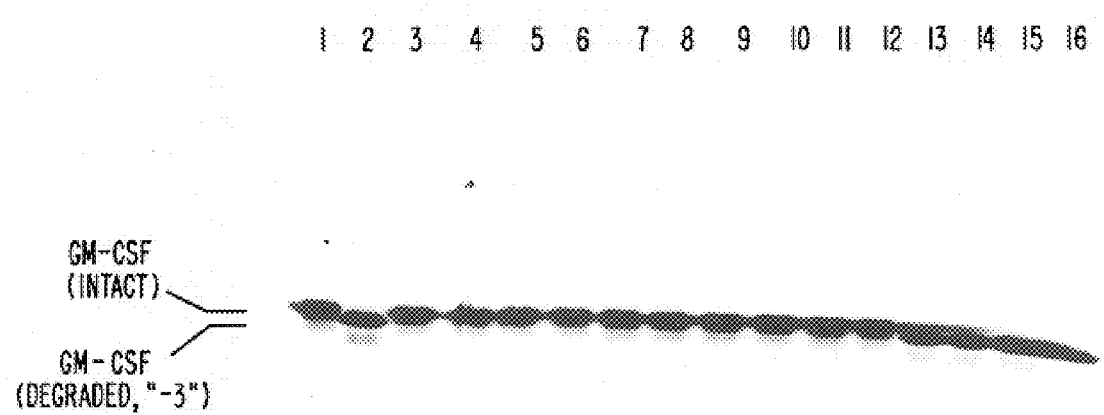
FIG. 5. Inhibition of Tap by APACMK: GM-CSF assay.
Figure 6:
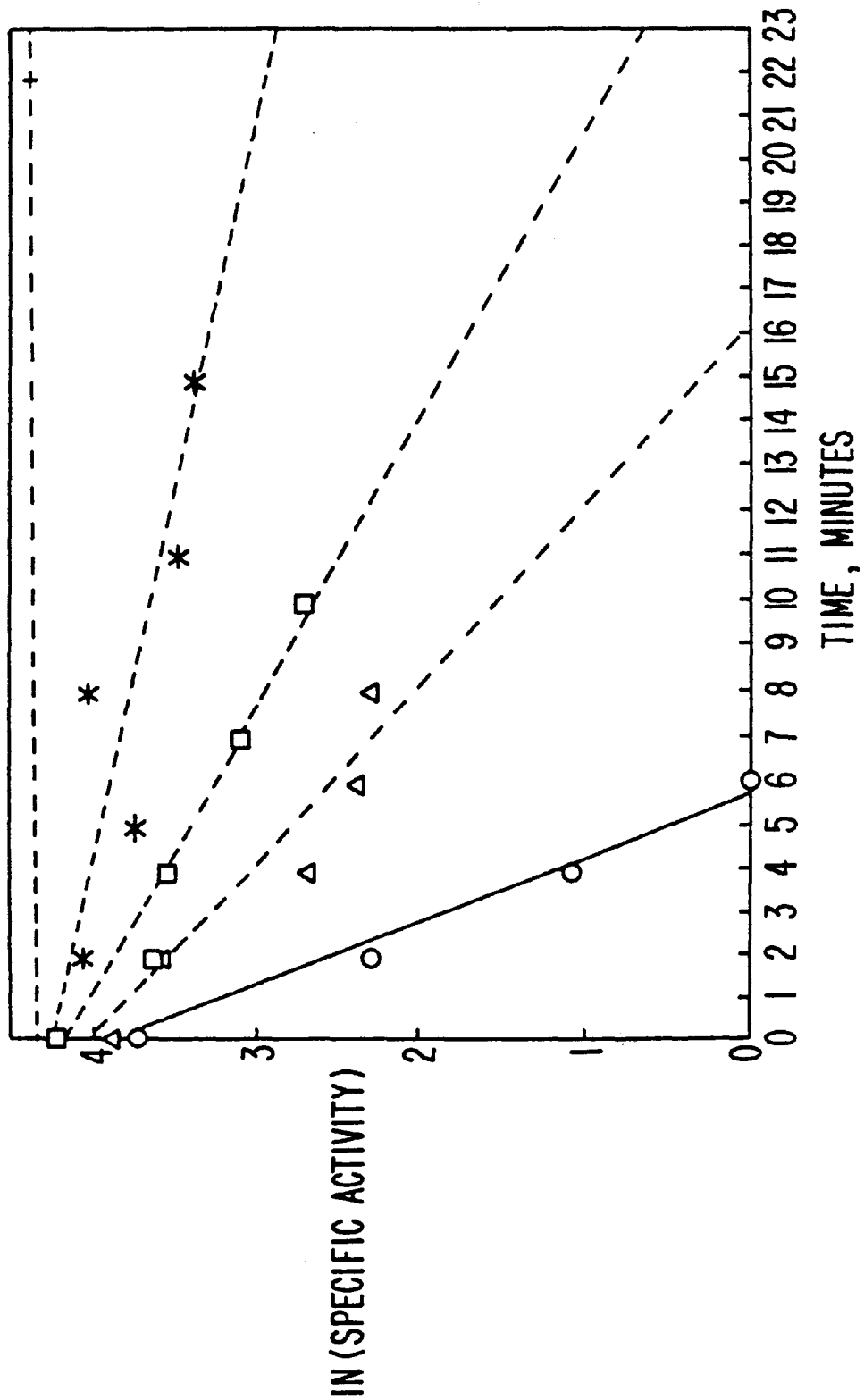
FIG. 6. Inhibition of Tap by APACMK: APA-pNA assay.

APACMK inactivated Tap at very low concentrations when residual activity was assayed with GM-CSF or APA-pNA respectively (FIGS. 5 and 6).

FIG. 5 shows the titration of Tap with APACMK as assayed with GM-CSF. The assay was performed as described in Example 7. The Tap concentration in the assays was 5 nM. Lane 1=GM-CSF standard; Lane 2=GM-CSF after digestion with Tap in the absence of APACMK; Lanes 3 and 4=150 uM APACMK; Lanes 5 and 6=15 uM APACMK; Lanes 7 and 8=1.5 uM APACMK; Lanes 9 and 10=150 nM APACMK; Lanes 11 and 12=15 nM APACMK; Lanes 13 and 14=1.5 nM APACMK; Lanes 15 and 16=150 pM APACMK.

FIG. 6 shows the inactivation of Tap by various APACMK concentrations when assayed with APA-pNA as substrate. The concentration of Tap in the inactivations was 1.0 uM. The inactivation and assay were conducted as described in Example 8. In FIG. 6, (○)=2.70 uM APACMK; (Δ)=2.16 uM APACMK; (□)=1.73 uM APACMK; (*)=1.38 uM APACMK; (+)=No APACMK.

The inhibitor APACMK yielded $K_i$=3.3 uM and $k_{inact}$=0.14 $min^{-1}$ with >99% inactivation within 6 minutes at 0° C. at an inhibitor concentration of 2.7 uM and an inhibitor/enzyme molar ratio of 2.7 (FIG. 6). The methods employed are described in Examples 6, 7, and 8.

Figure 7:
FIG. 7. Inhibition of degradation of GM-CSF during fermentation in the presence of APACMK.

FIG. 7 demonstrates the inhibition of Tap by APACMK during the fermentation of *S. lividans* grown in the presence and absence of 10 uM APACMK as described in Example 9. When APACMK and GM-CSF were added to the protease-containing broth from *S. lividans* fermentations, the formation of the GM-CSF(-3) degradation product was inhibited. Lane 1=Standard containing GM-CSF and GM-CSF(-3). Lanes 2–6 show a fermentation in the presence of 10 uM APACMK. Lane 2=25 hours growth; Lane 3=27 hours growth; Lane 4=29 hours growth; Lane 5=31 hours growth; Lane 6=48 hours growth. Lanes 7–11 show a fermentation without APACMK. Lane 7=25 hours growth; Lane 8=27 hours growth; Lane 9=29 hours growth; Lane 10=31 hours growth; Lane 11=48 hours growth. GM-CSF degradation was analyzed by native gel electrophoresis.

III. Nucleotide Sequence Encoding Streptomyces Proteases and Amino Acid Sequence of Such Proteases Methods of identifying and isolating the DNA encoding Tap are described in Example 10.

Figure 8:
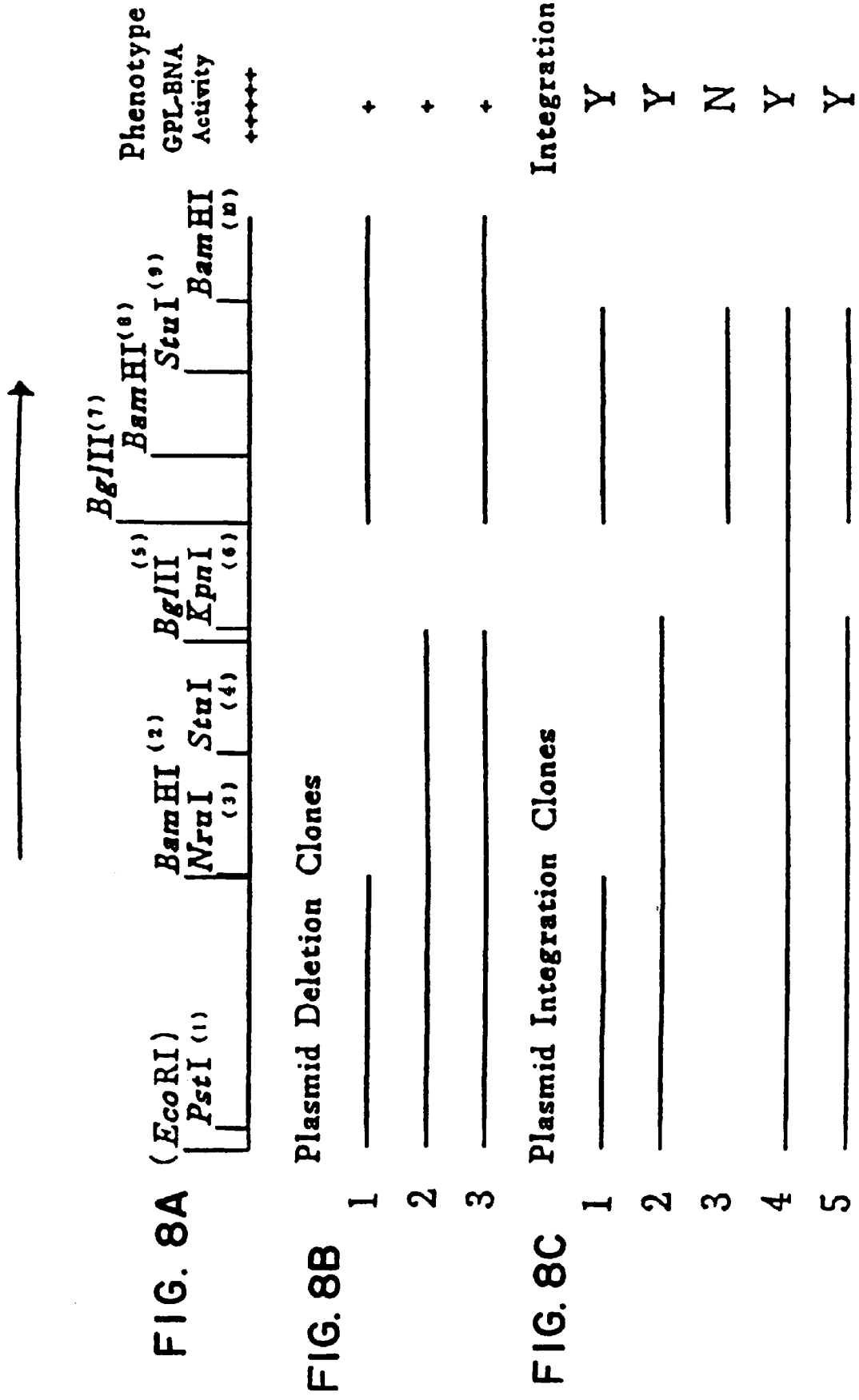
FIG. 8. (A) Common restriction map for tap-containing plasmid DNA isolated from clone P3-13 (and P3-5).

FIG. 8 is a restriction enzyme site map of cloned tap DNA. FIG. 8(A) The location and direction of potential protein encoding regions is shown by arrows, of which the larger represents the tap gene. Phenotype in the GPL-bNA hydrolysis agar plate assay is shown qualitatively as the number of + signs judging red color developed on the colonies. The EcoRI site shown in parentheses was present in the pSS12 vector adjacent to the BamHI cloning site. FIG. 8(B) None of the three deletion clones shown produced any more red color in colonies than did the pSS12 control plasmid and they were scored as "+" due to the background level of hydrolysis from the chromosomally-encoded tap gene in the *S. lividans* 66 host. (C) The DNA fragments shown were subcloned into the integration plasmid and used to transform protoplasts of *S. lividans* 66 to thiostrepton resistance. Clone numbers 1, 2, 4 and 5 all produced thiostrepton-resistant transformants, whereas clone 3 did not presumably due to the small size of the homologous DNA fragment in this clone.

Figure 9:
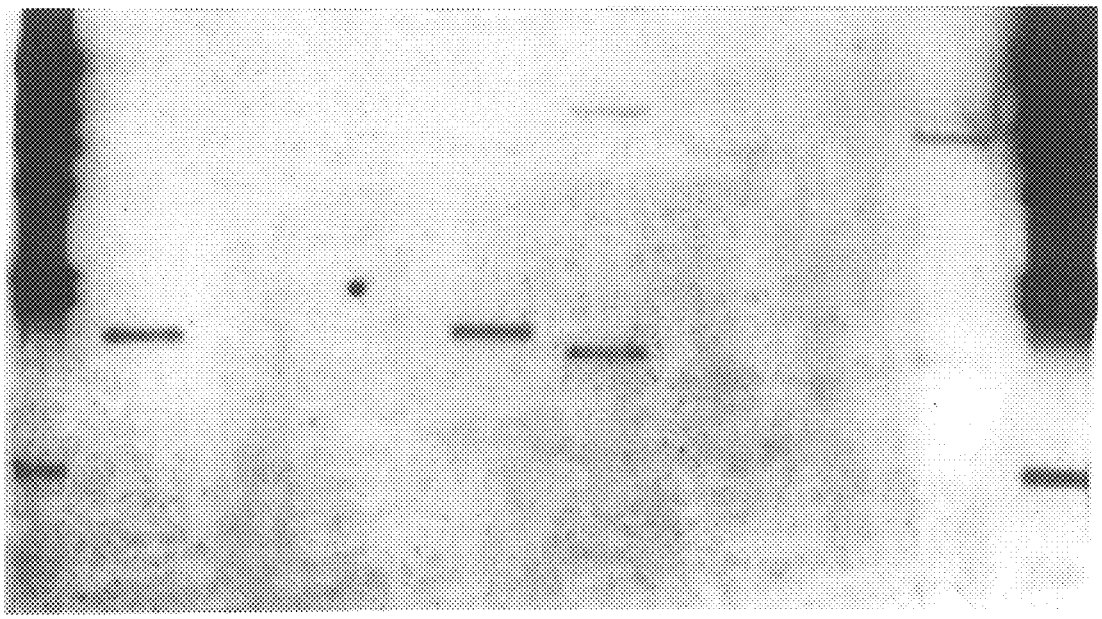
FIG. 9. Southern hybridization analysis of chromosomal DNA from *S. lividans* 66 and *S. lividans* MS7, using DNA from the P3-13 plasmid (0.3 kb BglII) as a probe.

FIG. 9 is a Southern hybridization analysis of the chromosomal tap locus in *Streptomyces lividans* 66 and deletion mutant strains. The DNA was digested with BamHI or StuI and transferred to a nylon membrane (Hybond, Amersham). Using a $^{32}$P-labelled probe for the BglII fragment internal to the tap gene resulted in a strong band of hybridization at approximately 1.8 kbp in the BamHI digests (lanes 2 and 5) and two bands in the StuI digests (lanes 6 and 9) for both the *S. lividans* control and colony #3 indicating that this DNA fragment was present in both strains. However, no hybridizing bands were observed for colonies 2 and 3 (lanes 3, 4, 7 and 8) confirming the loss of the 0.3 kbp BglII fragment. Lanes 1 and 10 show a Lambda/HindIII molecular weight marker.

Figure 10:
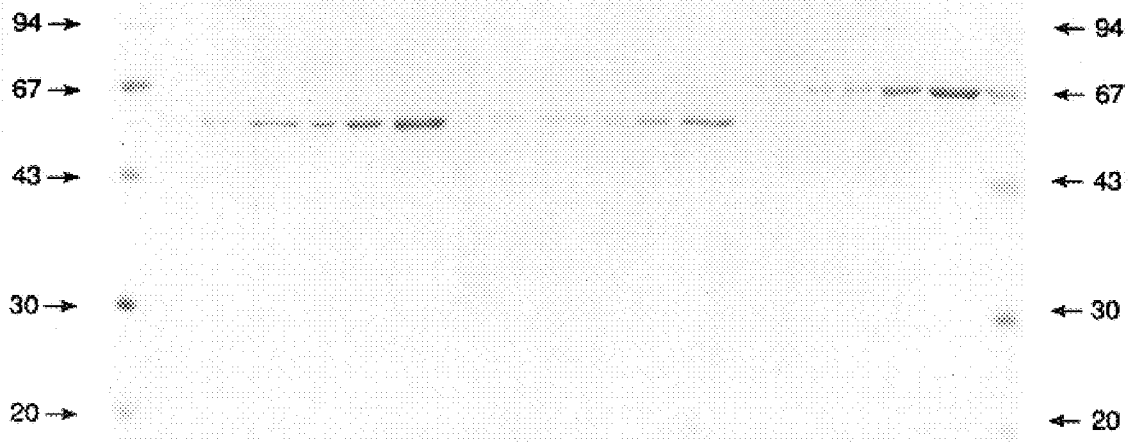
FIG. 10. Profiles of extracellular proteins from *S. lividans* 66 strains carrying the P3-5 and P3-13 clones; the profiles were generated by SDS-PAGE and the gels stained with Coomassie Brilliant Blue.

FIG. 10 is an SDS-PAGE analysis of cell-free broth supernatants from cultures of *S. lividans* 66 carrying the P3-13 or P3-5 plasmids. Cultures were sampled at 23 or 29 hours after inoculation into TSB medium.

FIG. 11 is a conversion of exogenously added, purified full length GM-CSF degraded to the -3 form upon incubation with fermentation culture supernatants from culture samples carrying the tap clones.

The nucleic acid sequence for the *S. lividans* tap gene is shown in FIGS. 12A–12C. The deduced amino acid sequence is shown for each codon.

Serine proteases possess a nucleophilic serine which attacks the carbonyl of the peptide bond to catalyze hydrolysis (White, Handler and Smith, 1973). Although the nucleophilic serine modified by PMSF has not been isolated, a homology study of the DNA sequence can identify potential candidates. The protease is encoded by the DNA sequence shown in FIGS. 12A–12C. The amino acid sequence derived from the DNA sequence is also shown.

The most likely active site serine residue was identified by its homology with that described for a serine esterase enzyme characterized in a Pseudomonas species by the conserved amino acid sequence motif (SEQ ID NO:9) GXSXG (Menn et al., 1989). The homologous sequence in Tap would be (SEQ ID NO:10) GVSYG (residues 243–247).

FIG. 13 is the amino acid sequence similarity between Tap and the HOHD from *Pseudomonas putida* F1. The amino acid sequences were compared using the BLAST (Altschul et al) program to screen the protein sequence databases.

The first 15 residues of the N-terminal of the isolated wild-type protease (Table II) have been determined and identically matched amino acids 40–54 derived from the DNA sequence (FIGS. 12A–12C). Residues -39 to -4 appear to be a signal peptide. An autolytic tripeptide cleavage removing APA after signal peptide removal would yield the N-terminal found for the secreted protease.

Table III shows the amino acid composition of the wild-type Tap. The amino acid composition derived from the corresponding portion of the tap gene DNA sequence (FIGS. 12A–12C) is shown for comparison. The composition data was obtained as described in Example 4.

The small differences in composition may be attributable to low level impurities in the enzyme sample. The method of analysis for the wild type enzyme is described in Example 4.

The N-terminal of the protease from the overproducer (P3-5) (Example 13) matches the sequence of the N-terminal of the wild-type enzyme. Both the isolated wild-type and isolated overproducer proteases had an apparent molecular weight of 55,000 daltons as determined by SDS-PAGE (FIG. 3). These factors indicated that the wild-type protease and the P3-5 overproduced protease were the same enzyme.

A further embodiment of this invention relates to the use of strains, containing specific impairments in their capability to

TABLE III

| | Mole Percentage | |
|---|---|---|
| Amino Acid | Protein | DNA |
| Asp + Asn | 13.6 | 12.4 |
| Glu + Gln | 10.9 | 7.6 |
| Ser | 4.7 | 4.7 |
| Gly | 10.0 | 8.9 |
| His | 2.2 | 2.3 |

TABLE III-continued

|  | Mole Percentage | |
| Amino Acid | Protein | DNA |
| --- | --- | --- |
| Arg | 7.4 | 7.4 |
| Thr | 6.3 | 6.3 |
| Ala | 14.3 | 14.3 |
| Pro | 7.2 | 7.2 |
| Tyr | 3.9 | 3.8 |
| Val | 6.4 | 7.6 |
| Met | 1.2 | 1.3 |
| Ile | 2.3 | 3.0 |
| Leu | 5.6 | 6.3 |
| Phe | 1.7 | 2.5 |
| Lys | 2.5 | 4.4 | produce secreted proteases, and the isolation and purification of other proteases which cleave substrates such as APAbNA and which also exist in the wild type strain but are expressed at much lower levels than Tap. Methods are described in Examples 20–23 to identify the genes encoding such minor proteolytic activities. It would be extremely difficult to purify such proteases from the wild type strain whereas the methods described here are rapid and simple. One protease (designated Ssp) having significant amino acid sequence homology with the B. subtilis protein Subtilisin BPN was identified by virtue of its ability to cleave APAbNA using the agar plate assay screening method. Furthermore, deletion of this gene from the S. lividans chromosome in a strain in which the tap gene had already been inactivated resulted in an incremental reduction in the APA-pNA hydrolytic capability of the strain.

Another protease gene was identified and shown to encode a protease which catalyzed the hydrolysis of APA-pNA and also showed a significant amino acid sequence homology to that of the Tap. Particularly strong sequence conservation was noticed around the putative active site serine residue of the Tap.

IV. Methods of Preparing Nucleic Acid Sequences Capable of Coding For the Impaired Proteases Methods of preparing nucleic acid sequences capable of coding for the impaired proteases include: site specific mutagenesis to alter the sequence coding for an essential component of the activity and/or the expression of the protease; and deletion or mutation of the wild type gene by exposure to mutagens. Generally, the deletion of a wild type gene together with the insertion of an impaired gene, would be preferred.

Example 15 describes production of DNA clones with various deletions and mutations resulting in the identification of DNA sequences the removal of which lead to inactivation of the tap gene.

V. Methods of Producing Host Cells with Impaired Protease Activity

Vectors were prepared according to Section III.

Recombinant vectors and isolated segments may therefore variously include the basic protease active site encoding region in an inactive form, coding regions bearing selected alterations or modifications in the basic coding regions, or larger proteins which include the basic coding region. An example is shown in FIG. 8B. In any event, it should be appreciated that due to codon redundancy, this aspect of the invention is not limited to alteration of the particular DNA sequences shown in FIGS. 8B or 8C.

Recombinant vectors such as the foregoing are useful both as a means for preparing quantities of the protease-encoding DNA itself, or as a means of producing defective proteases for use in transforming recombinant host cells for use in fermentation processes to produce various peptides and proteins.

Example 16 describes the use of the deletion clones of the tap gene for integrational mutation into the S. lividans 66 chromosome resulting in inactivation of the wild type tap gene. Loss of the wild type tap gene occurred by homologous recombination with the integrated mutant DNA sequence using the natural ability of the S. lividans host cell to resolve such regions of chromosomal DNA containing directly repeated nucleotide sequences. Resolution occurred apparently at random to produce strains carrying either the wild type parental tap gene or the exchanged mutant tap gene. Mutant strains were identified by their inability to hydrolyse the chromogenic substrate GPL-bNA.

Example 14 describes the use of chemical mutagenic treatment of spores of the S. lividans 66 strain to produce mutant strains in which the Tap encoding DNA is defective, resulting in reduced or abolished expression of Tap.

EXAMPLES

Example 1

Purification of Wild-Type Tripeptidyl Aminopeptidase

S. lividans 66 was grown in 11 liters of minimal media (minimal media=12 g Difco Soytone, 10.6 g $K_2HPO_4$, 5.3 g $KH_2PO_4$, 2.5 g $(NH_4)_2SO_4$, and 1.0 g $MgSO_4$-$7H_2O$ per liter) for 24 hrs at 32° C. with stirring at 300 rpm in a Chemap fermenter. Cells were removed from the media by ultrafiltration with a 0.45 um filter (Pellicon System, Millipore). Proteins in the filtrate were concentrated by ultrafiltration employing a membrane with a 10 kDa cutoff (Millipore). The protease activity was followed by assaying with APApNA and GMCSF as described in Example 2. The protease was precipitated at 4° C. by lowering the pH to 4.0 with 0.1M HCl. The precipitate was collected by centrifugation (Model J2-21, Beckman) at 10,000 g at 4–10° C. and was redissolved in 50 ml 10 mM Tris-HCl, pH 8.0. After dialysis against 4 liters of the Tris buffer at 4° C., the protease was loaded at ambient temperature onto a 1.6×10 cm anion exchange column (Q-Sepharose Fast Flow, Pharmacia) equilibrated with the Tris buffer. After washing with equilibration buffer, the bound protease was eluted with a 200 ml gradient from 0 to 500 mM NaCl at a flow rate of 2 ml/minute. The active fractions were pooled and made 2M in ammonium sulfate. This material was loaded at ambient temperature onto a 1.6×10 cm hydrophobic interaction column (Phenyl-Sepharose Fast Flow, Pharmacia) equilibrated in 10 mm Tris-HCl, pH 8.0, 2M ammonium sulfate. After washing with equilibration buffer, the column was eluted with a 200 ml gradient from to 2 to 0M ammonium sulfate at a flow rate of 2 ml/minute. The active fractions were assayed for purity by SDS-PAGE.

Example 2

Assays of Tap Activity

Aliquots of Tap column fractions were diluted 100-fold with 20 mM Tris-HCl, pH 8.0.

GM-CSF as Substrate

To 10 ul of rhGM-CSF (10 ug, Cangene) and 20 ul 20 mM Tris-HCl, pH 8.0, 20 ul of Tap were added. The assays were incubated at 37° C. for 2 hrs. 20 ul of 125 mM Tris-HCl, pH 6.8, 0.1% bromophenol blue in 50% aqueous glycerol were added. Products were separated by native gel electrophoresis at constant current on a 17% polyacrylamide gel by a modification of the method of Davies (Davies, 1964) in which the pH of all buffers was modified with $H_2SO_4$. Products were visualized by staining with Coomassie Blue G-250 (see FIG. 1A).

IL-3 as Substrate

To 50 ul 20 mM Tris-HCl, pH 8.0, 40 ul rhIL-3 (2.5 ug/ul, Cangene) was added followed by 10 ul Tap. The assays were incubated at 37° C. 25 ul aliquots were withdrawn at the desired time points and frozen on crushed dry ice. The products were separated by isoelectric focusing from pH 3–10 using Pharmalyte 3–10 (Pharmacia) ampholytes (FIG. 4). Products were visualized by staining with Coomassie Blue G-250. Intact IL-3 had a pI=7.4. The -3 form demonstrates a pI=7.1.

APA-pNA as Substrate

The assay was conducted in a 96 well microtiter plate. To each well in the assay, 50 ul 100 mM Tris-HCl, pH 8.0, were added followed by 25 ul 3.2 mM APA-pNA. 25 ul of Tap were added to the wells and the absorbance was read at 405 nm. The assays were incubated at 37° C. for 2 hours. The absorbance was read at 405 nm. The activity (release of p-nitroaniline) was calculated from the change in absorbance.

Example 3

Inactivation of Tap with PMSF: Assayed with IL-3

Tap stock (Example 1) was diluted 100-fold with 20 mM Tris-HCl, pH 8.0. A fresh solution of 8.0 mM PMSF was prepared in isopropanol (iPrOH). A Stock Buffer of 20 mM Tris-HCl, pH 8.0 was prepared. Four preincubations were prepared as follows.

iPrOH=58 ul Stock Buffer+2 ul iPrOH
PMSF=58 ul Stock Buffer+2 ul PMSF/iPrOH
Tap+iPrOH =18 ul Stock Buffer+40 ul Tapgw 2 ul iPrOH
Tap+PMSF=18 ul Stock Buffer+40 ul Tap+2 ul PMSF/iPrOH These were incubated at 22° C. for 30 minutes. When the preincubation was complete, 40 ul rhIL-3 (2.5 ug/ul, Cangene) were added and incubation was initiated at 37° C. Aliquots of 25 ul were removed at 0, 1, 2, and 4 hours. These aliquots were immediately frozen on dry ice. When the sampling process was complete, the products were analyzed by isoelectric focusing from pH 3–10 (Example 2).

Example 4

Amino Acid Sequencing of Tap

Tap was purified as described in Example I and was desalted by size exclusion chromatography. An Immobilon PVDF membrane (Millipore) was solvated according to the manufacturers instructions. Tap was adsorbed to the membrane by filtration employing a slot blot assembly. Protein bound to the membrane was visualized with Amido Black. The sample was excised and subjected to automated Edman degradation for 15 cycles.

Example 5

Synthesis of APACMK 21.3 g (70 mmol) Boc-Ala-Pro (Bachem Biosciences) dissolved in 175 ml anhydrous dimethylformamide (DMF) were activated by adding 7.8 ml (70.7 mmol) 4-methylmorpholine followed by 9.3 ml (70.7 mmol) isobutylchloroformate at −20° C. with stirring. After 15 minutes, 15.1 g A-OBz in 175 ml anhydrous DMF were added. The solution was stirred for 1 hour at −20° C. and then for 17 hours at ambient temperature. The DMF was remove by vacuum rotary evaporation. The residue was taken up in 175 ml ethyl acetate and extracted each with 5% citric acid, saturated sodium bicarbonate, water, and brine. The organic layer was dried over anhydrous sodium sulfate for 1 hour. The sodium sulfate was remove by filtration.

2.5 g 5% pd on activated carbon were added and the suspension was agitated under a hydrogen atmosphere for 2 hours. At that time, the starting material had been completely converted to product. The hydrogenation catalyst was removed by filtration through Celite. The solvent was removed by vacuum rotary evaporation.

The resulting 23.7 g (66.3 mmol) of Boc-APA were dissolved in 140 ml anhydrous ethyl acetate and reacted with 7.8 ml (70 mmol) of 4-methylmorpholine followed by 9.2 ml (70 mmol) of isobutylchloroformate at −20° C. with stirring. After 15 minutes, a solution of diazomethane in anhydrous ether prepared from 100 mmol N-methyl-N-nitroso-p-toluenesulfonamide (Aldrich) was added. After 1 hour at ambient temperature, the solution was extracted twice with 140 ml portions of water. The organic layer was dried over 2 g anhydrous sodium sulfate powder for 1 hour. The solution was removed by decantation. Deblocking of the N-terminal and generation of the chloromethylketone group were achieved simultaneously by adding 100 ml of HCl (g) saturated ethyl acetate. The resulting solution was allowed to stand at ambient temperature for 30 minutes. The product was removed from the organic solvent by extraction into 400 ml of water. The aqueous pool was frozen and lyophilized to yield the product, APACMK, as its hydrochloride salt.

Example 5A

Synthesis of Peptide-substituted Chloromethylketones

The skilled artisan will recognize that other peptide-CMK compounds are prepared using techniques similar to those used in Example 5 to make APACMK. Other suitable inhibitors include APM-CMK, APS-CMK, GPL-CMK, SPA-CMK and APF-CMK. The method of manufacture of chloromethylketone with other tripeptidyl extensions is similar to that described for APA-chloromethylketone. In these other cases, the corresponding Boc-dipeptidyl and amino acyl starting materials are used in lieu of Boc-Ala-Pro and Ala-OBz in Example 5. For example, APS-chloromethylketone is produced by first synthesizing Boc-Ala-Pro-Ser from equimolar amounts of Boc-Ala-Pro and Ser-OBz (both commercially available from Bachem Biosciences) followed by the addition of the chloromethylketone group. Similarly, a GPL-chloromethylketone may be produced by the same general method using Boc-Gly-Pro and Leu-OBz respectively.

Example 6

Inactivation of Tap by APACMK: Assayed with APA-pNA

A stock solution of 10 nM Tap in 100 mM Tris-HCl, pH 8.0 was prepared. Serial dilutions of 210 uM, 21 uM, 2.1 uM, 210 nM, 21 nM, and 2.1 nM APACMK (Example 5) were prepared. To the microtiter well, 25 ul of Tap followed by 25 ul of an APACMK dilution or distilled water, for an uninhibited control, were added. The assays were incubated for 20 minutes at 22° C. 50 ul 1.6 mM APA-pNA were added to each well. The absorbance was read at 405 nm then incubated at 37° C. The change in absorbance at 405 nm was read after 15 and 60 minutes of incubation.

Example 7

Inactivation of Tap by APACMK: Assayed with GM-CSF

A stock solution of 10 nM Tap in 20 mM Tris-HCl, pH 8.0 was prepared. Serial dilutions of 210 uM, 21 uM, 2.1 uM, 210 nM, 21 nM, and 2.1 nM APACMK (Example 5) were prepared. To 20 ul Tap, 20 ul of an APACMK dilution (or water for an uninhibited enzyme control) were added and incubated at 22° C. for 30 minutes. 10 ul of GM-CSF (1 ug/ul, Cangene) were added and incubated at 37° C. for 2 hours. Products were analyzed by native gel electrophoresis as described in Example 2.

Example 8

Inactivation of Tap by APACMK—Determination of Kinetic Constants

A stock solution of 1.1 uM Tap in 50 mM Tris-HCl, pH 8.0 was prepared. APACMK stock solutions of 11 uM, 13.8 uM, 17.3 uM, 21.7 uM, 27.0 uM, 54.0 uM, 108 uM, and 1.08 mM were prepared. The Substrate Solution was 50 mM Tris-HCl, pH 8.0, 0.8 mM APA-pNA. The inactivation was performed by placing 90 ul of Tap (1 nanomole) in a 1.5 ml Eppendorf tube on ice and adding 10 ul of water (uninhibited control) or 10 ul of APACMK. A 10 ul aliquot was removed immediately and was assayed by adding it to a cuvette containing 390 ul Substrate Solution at 22° C. The initial velocity was obtained from the change in absorbance at 405 nm during the first 10 seconds of the assay. Additional aliquots were removed at time points and assayed by the same method. At APACMK concentrations greater than 5.0 uM in the incubation, it was not possible to remove an aliquot from the incubation before 90% inactivation occurred.

Example 9

Application of APACMK in Fermentation 100 ml of media was inoculated in 500 ml baffle-bottom flasks with 100 ul of S. lividans 66 working seed bank material. The cultures were grown in a New Brunswick gyratory incubator at 32° C. and 240 rpm. The cultures were sampled at 25, 27, 29, 31, and 48 hours post-inoculation and analyzed by native gel electrophoresis (see FIG. 7). Following removal of the 25 hour sample, 100 mM APACMK in sterile water were added to yield a final concentration of 10 uM. A control flask without APACMK was retained. The addition of APACMK significantly reduced formation of GM-CSF(-3) but did not inhibit cell growth.

Example 9A

Use of APACMK During Expression of Heterologous Protein in S. lividans

Protoplasts are prepared from S. lividans, and are transformed using GM-CSF expression vector pAPO.GMCSF (as U.S. Pat. No. 5,200,327). The transformed cells are grown in liquid culture and the supernatant fractions are collected following the teaching of Example 11. 100 mM APACMK in sterile water is added to yield a final concentration of 10 uM. Sterile water (without APACMK) is added to control cultures. Aliquots of each culture supernatant are analyzed by SDS-PAGE. The degree of degradation of GM-CSF in the presence and absence of APACMK is assessed using the results of the SDS-PAGE.

The skilled artisan will recognize that the selection of an appropriate aminopeptidase inhibitor is a matter of routine optimization, depending on experimental conditions and the nature of the expressed heterologous protein. Furthermore, the appropriate concentration of the aminopeptidase inhibitor will also vary with expermental conditions. The skilled artisan will recognize that determination of a suitable inhibitor concentration is a matter of routine optimization.

Example 9B

Use of APACMK During Expression of Heterologous Protein in E. coli, Bacillus or Psudomonas E. coli, Bacillus or Psudomonas are transformed with expression vectors encoding GMCSF using art-recognized techniques. The transformed cells are grown in liquid culture and the supernatant fractions are collected following the teaching of Example 11. 100 mM APACMK in sterile water is added to yield a final concentration of 10 uM. Sterile water (without APACMK) is added to control cultures. Aliquots of each culture supernatant are analyzed by SDS-PAGE. The degree of degradation of GMCSF in the presence and absence of APACMK is assessed using the results of the SDS-PAGE.

The skilled artisan will recognize that the selection of an appropriate aminopeptidase inhibitor is a matter of routine optimization, depending on experimental conditions and the nature of the expressed heterologous protein. Furthermore, the appropriate concentration of the aminopeptidase inhibitor will also vary with expermental conditions. The skilled artisan will recognize that determination of a suitable inhibitor concentration is a matter of routine optimization.

Example 10

Construction and Screening of a S. lividans Genomic Library

A S. lividans 66 (Hopwood et al., 1983) genomic library was made using size fractionated (3–12 kbp) fragments of chromosomal DNA partially digested with Sau 3AI and ligated into the BamHI site of the bifunctional cloning vector, pSS12 (Butler et al., 1992). The ligated DNA was used to transform competent cells of E. coli HB101 and pooled plasmid DNA was isolated from a mixture of approximately 30,000 transformed colonies grown in SOB medium (Maniatis et al., 1982) containing ampicillin (Sigma). This DNA was used for transformation of S. lividans 66 protoplasts yielding 15,000 transformant colonies resistant to thiostrepton (E. R. Squibb). Two days later the colonies were screened by overlaying with substrate mixture (containing 5 ml phosphate buffer (50 mM, pH 7.0), 25 $\mu$l GPLbNA (20 mg.ml$^{-1}$ in DMSO), 0.1 ml Fast Garnet GBC [10 mg.ml$^{-1}$ in water]). The plates were incubated for three minutes at room temperature and washed three times with saline solution (Atlan et al., 1989, Alvarez et al. , 1985). Positive colonies stained intensely orange against a background for pale orange colonies.

Two colonies reproducibly showed strong color. Plasmid DNA was isolated from each of these two colonies and the phenotype was retained when the DNA was used to transform protoplasts of S. lividans 66.

The plasmid DNA from each of these clones (P3-5 and P3-13) was investigated by restriction enzyme analysis. The data indicated that P3-5 and P3-13 were identical (presumably siblings) and the common restriction map is shown in FIGS. 8A–8C. Southern hybridization analysis of chromosomal DNA, using the plasmid P3-13 as a probe (FIG. 9), suggested that the DNA contained in P3-13 had not been rearranged during cloning.

Example 11

Tap Activity of S. lividans 66 Strains Carrying the P3-5 and P3-13 Clones

The S. lividans 66 strains carrying the P3-5 and P3-13 clone or pSS12 were grown in TSB (containing 1% glucose, 0.1 M MOPS and 20 µg ml$^{-1}$ thiostrepton). Aliquots (40 ml) of each culture were removed at 23 and 29 hours, and the supernatant and mycelium fractions were separated by centrifugation. Aliquots of the supernatant fractions were added to reactions (100 µl) containing various tripeptide-bNA substrates (8 nmol) in microtiter wells. After incubation at 37° C. for 4 hours, a solution (50 µl) containing Fast Garnet GBC dye was added and the $A_{540}$ was measured in a microtiter plate reader. The results are shown in Table IV.

TABLE IV

| Sample Supernatants | Tripeptidyl Aminopeptidase Activity ($A_{540}$ above background) | | | |
|---|---|---|---|---|
| | GPL-bNA | GPM-bNA | APF-bNA | D-FPR-bNA |
| P3-5/23 HRS | Max | Max | Max | 0.02 |
| P3-5/29 HRS | Max | Max | Max | 0.08 |
| SS12/23 HRS | 0.19 | 0.28 | 0.63 | 0.02 |
| SS12/29 HRS | 1.38 | 2.46 | Max | 0.17 |

("Max" indicates a $A_{540}$ reading of >3.0)

At as early as 23 hours of culture, a 1 µl aliquot of the supernatant from S. lividans carrying the P3-5 clone was showing strong activity against the GPL-, GPM- and APF-bNA substrates. At the same time point, a 25-µl aliquot of the control culture had at least 15 to 20 fold lower activity with the same substrates. However, against the D-FPR- and APF-bNA substrates, the Tap over-producer had little activity over the control. An aliquot (1 µl) of each supernatant (which was harvested after 23 hours of growth) was added to a reaction containing 4 µg of purified intact GM-CSF. Following a 2.5-min. incubation at 37° C., the proteins were analyzed by native PAGE and stained with Coomassie Brilliant Blue. The full-length GM-CSF (lane 1 of FIG. 11) was rapidly converted to the -3 form upon incubation with culture supernatants from cells carrying the tap clones. By contrast, no significant degradation was observed when GM-CSF was incubated with the control culture due to the small volumes of culture supernatant and short time of incubation used compared to those described in Example 2.

Example 12

Analysis of Extracellular Proteins From S. lividans 66 Strains Carrying the p3-5 and p3-13 Clones The S. lividans 66 carrying the P3-5 and P3-13 clones were grown in liquid culture, and supernatant fractions were collected following the teaching of Example 11. As described by Laemmli (1970), samples were prepared from aliquots (200 µl) of the supernatant fractions, and SDS-10% polyacrylamide gels were run at 100 v for 5 to 6 hours. The profile of separated proteins was then visualized by staining with Coomassie Brilliant Blue (FIG. 10). An abundant protein with an apparent molecular weight of 55,000 daltons was present among the extracellular proteins from S. lividans 66 carrying either P3-5 (lanes 2 to 7) or P3-13 (lanes 8 to 13). From 23 to 29 h of culture, the level of Tap increased to approximately 0.1 mg/ml, relative to the BSA standards (lanes 14 to 19). Lanes 1 and 20 show molecular weight markers.

Example 13

Amino Terminal Amino Acid Sequence of the Tap Protein Purified From an S. lividans 66 Strain Carrying the P3-13 Clone The S. lividans 66 strain carrying the P3-13 clone was grown in liquid culture and supernatant fractions were collected, following Example 11. The extracellular proteins were separated by SDS-PAGE, following the teaching of Example 12, and transferred onto Immobilon PVDF (Millipore) membranes as directed by the supplier. After briefly staining the filters with Coomassie Brilliant Blue, the bands containing the major protein (apparent molecular weight 55,000 daltons) were excised from the filter, and subjected to automated Edman degradation analysis. The N-terminal amino acid sequence determined was: Asp-Gly-His-Gly-His-Arg-Ser-Gln (or Ser)-Asp-Ala.

Example 14

Production of Mutant Strains of S. lividans Defective in Protease Activities Using Chemical Mutagenesis S. lividans 66 spores were treated with N-methyl-N-nitro-N-nitrosoguanidine (MNNG) according to the method of Hopwood et al., (1985). Briefly, a suspension containing $2.5 \times 10^{12}$ spores in 3 mls of Tris/maleic acid buffer was incubated at 30° C. in a preweighed vial containing 10 mgs of MNNG (which had been solubilized in 0.5 ml DMSO immediately prior to the addition of the spore suspension). 1 ml aliquots were removed from the mixture at 30 minute intervals and washed twice by centrifugation to remove the MNNG. Serial dilutions of the treated spores were plated on agar medium to determine the effectiveness of the mutagenic treatment in terms of the proportion of viable surviving colony forming units remaining compared to untreated spores. Survival rates of $2.8 \times 10^{-3}\%$, $1.2 \times 10^{-4}\%$ and $9 \times 10^{-6}\%$ were observed after 30, 60 and 90 minutes, respectively.

Two hundred surviving colonies from each of the three treatment times were purified and examined for their ability to grow on minimal media. Colonies which were unable to grow were classified as auxotrophic mutants of which 1, 4 and 2 were observed at the 30, 60 and 90 minute treatment times, respectively.

Spores from the 60 minute treatment were, therefore, examined for the presence of strains carrying mutations which inactivated specific proteolytic phenotypes. A direct agar plate screening technique was used in which the colonies were overlayed with substrate mixture (containing 0.1 ml of GPL-bNA (Bachem Inc., 1 mg dissolved in DMSO), 0.1 ml Fast Garnet GBC (Sigma) dye (10 mg.ml$^{-1}$ in water), 6 ml of 50 mM phosphate buffer, pH 7.0 and 0.2 ml DMSO. The plates were incubated for twenty minutes at room temperature and washed three times with saline solution (Atlan et al., 1989, Alvarez et al., 1985).

Screening of 2,700 colonies using GPL-bNA revealed two colonies which did not turn red. Testing supernatants from liquid cultures of one of these colonies (12-5 or 12–8), with various chromogenic tripeptide substrates (Table V), confirmed that this specific hydrolytic ability had been either eliminated or at least very substantially reduced compared to the original untreated S. lividans strain.

TABLE V

Tripeptidyl Aminopeptidase Activity
($A_{540}$ above background)

| Sample Supernatants | GPL-bNA | GPM-bNA | APF-bNA | D-FPR-bNA |
|---|---|---|---|---|
| 12-5/T2 | 0.01 | 0.01 | 0 | 0 |
| 12-5/T4 | 0.10 | 0.10 | 0.05 | 0.06 |
| 12-8/T2 | 0.02 | 0.02 | 0 | 0 |
| 12-8/T4 | 0.13 | 0.12 | 0.12 | 0.08 |
| 1-5/T2 | 0.01 | 0.01 | 0.01 | 0.02 |
| 1-5/T4 | 2.55 | Max | Max | 0.09 |

("Max" indicates a $A_{540}$ reading of >3.0)

In a similar experiment to that described above, a L-bNA substrate was used, resulting in the isolation of one mutant (lap⁻) strain (1–5) from 1500 colonies screened. By comparison, the Tap activity of this mutant strain was unchanged from that of wild type S. lividans 66.

Aliquots of each culture supernatant were added to reactions containing 2.5 μg GM-CSF and incubated at 32° C. for 2 minutes. The proteins were separated by SDS-PAGE and visualized by Western blotting, using an antiserum raised against the amino terminal 35 amino acids of GM-CSF. At 40 h (T3), the cultures from the tap mutants, #11 and #12 contained less activity for converting GM-CSF to the -3 from than those from the S. lividans, MS2 and the lap mutant, #1.

Protoplasts were prepared from the various S. lividans 66 mutants, and were transformed using the GM-CSF expression vector pAPO.GMCSF (as described in Canadian patent number 1,295,567 and U.S. Pat. No. 5,200,327). The transformed cells were grown in liquid culture and the supernatant fractions were collected following the teaching of Example 11. Aliquots of each culture supernatant were analyzed by SDS-PAGE. The transformants with the tap mutants, 12-5 and 12-8 generally showed more intact GM-CSF at later time points in the culture than the S. lividans, MS2. However, the formation of the -3 form of GM-CSF was not completely eliminated with the tap mutants.

Example 15

Construction of A Deletion Subclone From the tap Clone

Specific deletions were made in the tap clone to localize the gene and enable chromosomal disruption. A 1.2-kbp DNA fragment was removed between BamHI (1100) and BglII (2300) (see FIG. 8B) to construct the deletion clone Δ1. P3-5 DNA was digested by means of EcoRI and BglII, and the vector fragment was isolated; and P3-5 was digested with EcoRI and BamHI and the 1.1-kbp insert fragment was isolated. The vector and insert fragments were ligated, using T4 DNA ligase, and used to transform E. coli. The plasmids were screened by restriction analysis and the correct plasmid, Δ1, used to transform protoplasts of S. lividans 66. The S. lividans 66 carrying the Δ1 deletion clone was screened with a plate assay using GPL-bNA. A transformant was grown in liquid culture, and the level of Tap activity was determined in a liquid assay using tripeptide-βnapthylamide substrates. The S. lividans 66 carrying the Δ1 deletion subclone had a similar Tap activity to that of the untransformed host strain.

Deletion clone Δ2 was constructed by subcloning the EcoRI-BglII fragment into the vector pSS12 which had previously been digested with EcoRI and BamHI. Δ3 was made by digestion of P3-5 DNA with BglII, followed by relegation, resulting in the loss of the 300 nt BglII fragment around the centre of the tap gene. The high level of Tap activity associated with the P3-5 plasmid was not observed with Δ2 or Δ3, confirming that the deletions resulted in loss of enzyme activity.

Example 16

Deletion Clones Used for Integrational Mutation of tap into the S. lividans 66 Chromosome Subcloning of the DNA insert sequences from the deletion clones was not straightforward due to the presence of multiple BamHI sites. A partial BamHI digestion of P3-5 DNA was followed by a complete EcoRI digestion. The 3.1 kbp tap-encoding fragment was isolated from an agarose gel and subcloned into the E. coli vector pT7T3 which had previously been digested with BamHI and EcoRI. Appropriate transformants were identified and the DNA insert was used to create further subclones in the pINT vector as follows. Δ1int was produced by a three way ligation of the EcoRI-BamHI, BglII-HindIII (in the polylinker of the pT7T3 vector) fragments from the pT7T3 subclone and the EcoRI-HindIII fragment produced by digestion of pINT. Δ2int was the result of a direct subcloning of the EcoRI-BglII fragment from the pT7T3 subclone into pINT digested with EcoRI and BamHI. Δ3int involved the BglII-HindIII fragment from the pT7T3 subclone and BamHI plus HindIII digested pINT. Δ4int was a direct subcloning of the whole inserted fragment in the pT7T3 subclone (EcoRI+HindIII) into the same sites in pINT. Δ5int was made from Δ4int by digestion with BglII and relegation. The DNA contained within the various Δint clones is shown in FIG. 8C.

Plasmid DNA was isolated from the E. coli transformed strains and used to transform protoplasts of S. lividans MS5 (a strain derived from S. lividans 66 by deletion of DNA fragments at the slpA and slpC (Butler el al., 1992) loci; in addition the pepP gene (Butler et al., 1993) and a second PepP-encoding gene (Butler et al., J. Ind. Microbiol., in the press) were also subjected to specific chromosomal DNA deletion events, each of which reduced the PepP activity of the S. lividans strains). Integrative transformants resistant to thiostrepton were purified and allowed to grow in the absence of thiostrepton to allow recombinational resolution to occur. Strains which had undergone excision events were easily identified by screening for the loss of the ability to hydrolyse GPL-bNA. The results obtained were somewhat unexpected. Δ1int did not produce any integrative thiostrepton-resistant transformants in three independent experiments. Δ2int did lead to integrative transformants, indicating that there was no practical impediment to recombination events at this locus on the S. lividans chromosome. Δ3int failed to produce integrative transformants, possibly due to the relatively small length of DNA (900 nt) available for homologous recombination to occur. Δ4int yielded tranformants as did Δ5int. Subsequent experiments using Δ1int were successful using S. lividans 66 protoplasts (to make a strain designated MS9 which was defective only at the tap locus) suggesting that the earlier failure in the MS5 experiment was due to the lower transformation capability of that particular batch of MS5 protoplasts.

Integrative transformants from Δ5int were grown in the absence of the thiostrepton selection on agar medium. After sporulation had occurred the spores were harvested and replated onto fresh agar plates. Colonies were screened using the βnaphthylamide substrate assay for tap activity. The frequency of excision events which led to loss of the activity was very low (approximately 1 in 1000). Three colonies were obtained with reduced Tap activity. Chromosomal DNA was isolated and Southern hybridization analysis (FIG. 9) confirmed that one colony (#2) had lost the 300 nt BglII fragment (lanes 3 and 7 compared to the S. lividans 66 control lanes 2 and 6). Similar experiments with a 3.3 kbp DNA probe revealed a complex hybridizing band pattern in colony 1 chromosomal DNA whereas colony 2 DNA showed only the expected bands with a reduction in size of one band consistent with the desired specific chromosomal deletion. Colony 2 was designated *Streptomyces lividans* MS7. Another strain was constructed using Δ5int and *S. lividans* 66 protoplasts. This strain was designated MS8 and shown to have properties indistinguishable from those of MS9.

Example 17

The *S. lividans* MS7 Strain Shows a Substantial Reduction in its Ability to Hydrolyse Tripeptide bNA Substrates and GM-CSF in vitro The *S. lividans* MS7 strain was grown in liquid culture (TSB medium) and supernatants collected by centrifugation to remove the mycelial material. Aliquots (50 μl) of the supernatants were added to each of the tripeptide substrates (8 nmol) in a final volume of 100 μl. After incubation at 37° C. for 45 minutes, 50 μl of a solution of Fast Garnet GBC dye was added and the $A_{540}$ measured using a microtiter plate reader.

Figure 14:
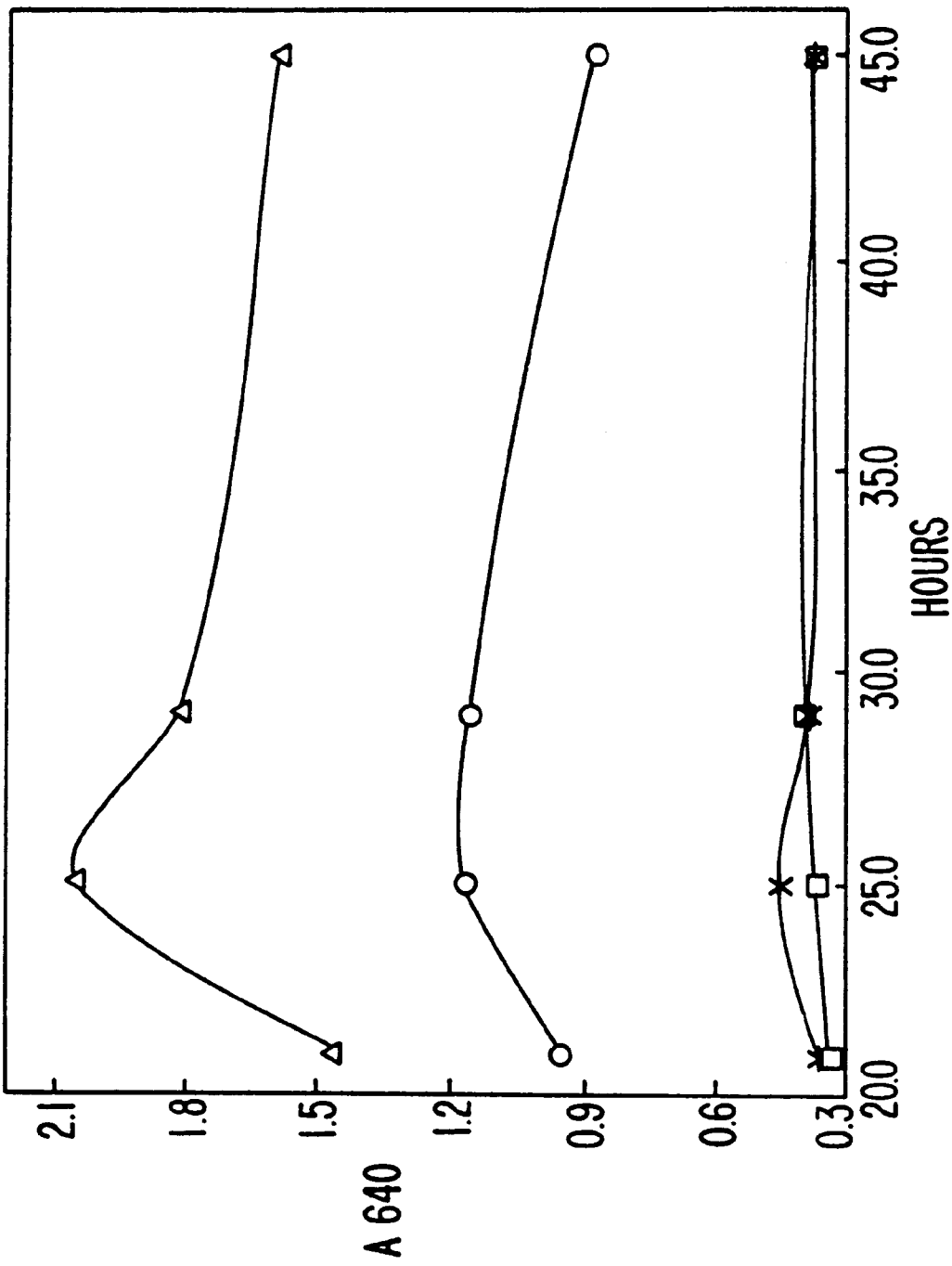
FIG. 14. Activity of fermentation culture supernatants from *S. lividans* MS5 (tap+) and *S. lividans* MS7 (tap−) strains against chromogenic tripeptide substrates.

FIG. 14 shows the activity of *S. lividans* MS5 (tap+) and MS7 (tap) strains against chromogenic tripeptide substrates. Cell-free broth from the strains was isolated at various times of fermentation (without thiostrepton) and incubated with either APA-bNA or GPL-bNA.

The symbols represent the following combinations:
MS7+APAbNA (-□-)
MS7+GPLbNA (-*-)
MS5+APAbNA (-Δ-)
MS5+APLbNA (-○-)

The results are summarized in FIG. 14 and indicate that under these assay conditions, the supernatants derived from the MS7 culture were (within experimental error) devoid of any significant hydrolytic ability against these substrates, whereas the supernatant derived from *S. lividans* MS5 showed the ability to rapidly degrade both substrates.

Figure 15:
FIG. 15. Reduction in the rate of degradation of intact GM-CSF by fermentation supernatants of cultures of the tap mutant.

FIG. 15 shows the degradation of full-length GM-CSF by cell-free broth from *S. lividans* MS5 and MS7. Cell-free broth was isolated from cultures grown without thiostrepton for 25 hours. Degradation was significantly slower for MS7 than MS5.

When the same supernatant samples were analyzed for the ability to degrade GM-CSF in vitro (according to the teaching of Example 15), it was clear that the rate of degradation of GM-CSF for the MS7 samples (FIG. 15, lanes 4–6) was much slower than for the MS5 samples (FIG. 15, lanes 1–3).

Example 18

Production of Undegraded GM-CSF by the *S. lividans* MS7 Strain

The GM-CSF expression plasmid vector pAPO.GMCSF was used to transform protoplasts of the *S. lividans* MS7 strain. Following the teaching of Example 11, liquid cultures were prepared from the transformed strain as well as transformants from the *S. lividans* MS5 strain.

Figure 16:
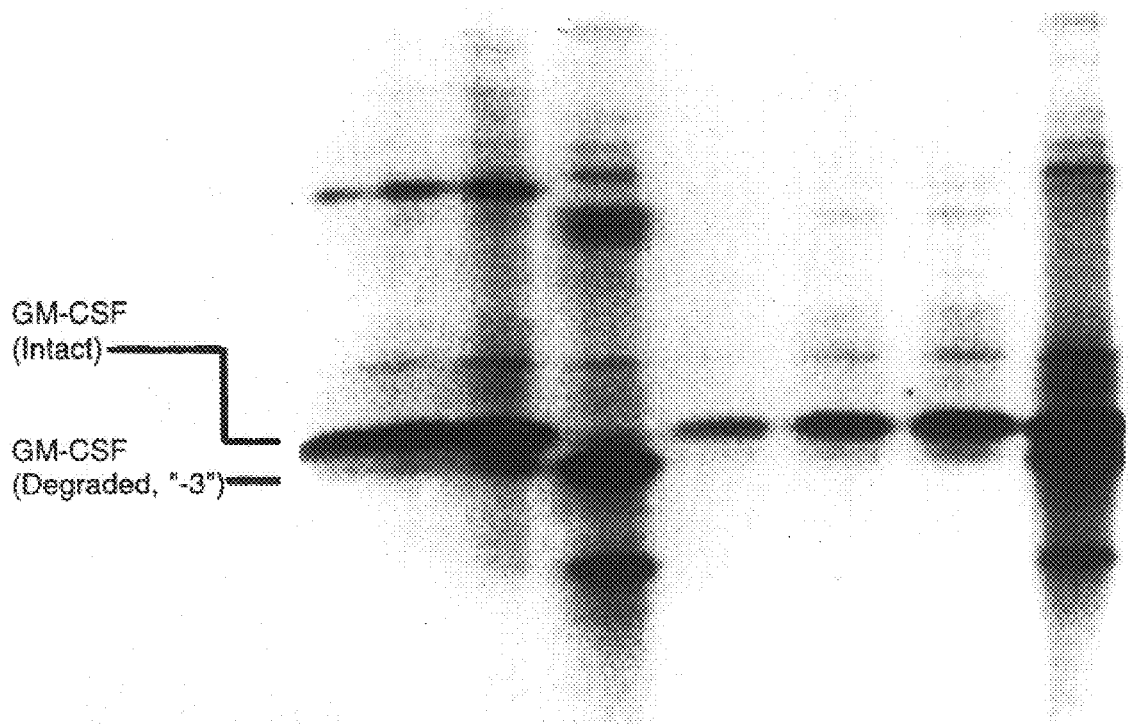
FIG. 16. PAGE resolution and Coomassie Brilliant Blue staining of fermentation supernatants from cultures of *S. lividans* 66 and *S. lividans* MS7 mutant protoplasts transformed with the GM-CSF expression vector pAPO.GMCSF.

FIG. 16 illustrates production of GM-CSF by *S. lividans* 66 and the deletion mutant strain MS7. Cell-free broth from the strains was harvested after fermentation for the times shown and analyzed by native PAGE.

Native PAGE analysis of the culture supernatants revealed that while degradation of the secreted GM-CSF occurred in both strains, it was only evident in the MS7 supernatant material (FIG. 16, lanes 5–8) at later times of growth compared to the MS5 samples (FIG. 16, lanes 1–4). This property of the new *S. lividans* MS7 strain allowed it to be used to produce a higher yield of undegraded GM-CSF than was possible using the wild-type *S. lividans* 66 strain.

Example 19

Tap Activity is Present in a Wide Variety of Streptomyces Species

Genomic DNA was isolated from the following Streptomyces strains. *S. alboniger* 504 (P. Redshaw, Austin College, Texas, USA), (*S. coelicolor* M130 (John Innes Institute), *S. fradiae* ATCC 14544, *S. griseus* IMRU 3499, *S. griseus* ATCC 10137, *S. parvulus* 2283 (John Innes Institute) *S. rimosus* ATCC 10970. 10 μg of each DNA were digested in 100 μl of appropriate buffer for the restriction enzymes BamHI and PstI respectively. 30 units of each enzyme were added together with 1 μl of RNAse A (10 mg/ml, Sigma). The reactions were incubated at 37° C. for 3 hours. A further 15 units of enzyme were added and the samples incubated overnight at 37° C. Digestions were terminated by the addition of 11 μl of stop buffer (Orange G, 0.08%; glycerol, 50%; EDTA, 67 mM; pH8). Approximately 3 μg of each digested DNA sample were loaded onto a 1% agarose horizontal gel and electrophoresed at 100 V for 4 hours. A molecular weight marker was included (Lambda DNA digested with HindIII, Bethesda Research Laboratories to calibrate the gel. After electrophoresis the gel was soaked in 0.25 M HCl, followed by 0.5M NaOH, 1.5M NaCl and rinsed in water. The DNA was transferred to a Nylon membrane (Boehringer Mannheim) using a Vacublot (Pharmacia) apparatus with 20× SSC buffer for 1 hour at 50 mbars pressure. After transfer the membrane was washed in 2× SSC and baked for 1.5 hours at 80° C.

The DNA insert fragment from the EcoRI site to the right-most BamHI site was isolated by partial BamHI and complete EcoRI digestions of the P3-13 DNA. The fragment was subcloned into the *E. coli* plasmid vector pT7T3 (Pharmacia). From this clone it was possible to isolate larger quantities of the same DNA fragment by digestion with EcoRI and HindIII. 0.5 μg of this 3.3 kbp-fragment were labelled according to the manufacturers's recommendations (Boehringer Mannheim) to produce a digoxigenin—labelled probe. 25 ng of probe were used per ml of hybridization solution. Lambda DNA was labelled in the same way to allow visualization of the molecular weight marker fragments. Hybridization was carried out at 68° C. overnight using 2.5 ml of hybridization solution per 100 cm² of nylon membrane. The hybridization solution contained; 5× SSC; blocking reagent, 1% (w/v); N-lauroylsarcosine, 0.1% (w/v); sodium dodecyl sulphate, 0.02% (w/v). Filters were prehybridized for 1 hour at 68° C. Probes were boiled for 10 minutes, quick chilled on an ice/NaCl bath, diluted with 100 μl hybridization solution and added to the prehybridized membrane in a stoppered glass bottle. Hybridization and prehybrization were carried out using a Hybaid mini-hybridization oven. Membranes were washed twice at 68° C. for 30 minutes in 5× SSC, 0.1% SDS (50 ml/100 cm² membrane). The membranes were then transferred to plastic containers and processed according to the manufacturer's instructions.

Finally, membranes were transferred to plastic bags, sealed and incubated at 37° C. for 30 minutes. Membranes were then exposed to X-ray film for 10 minutes. After development of the X-ray film the autoradiogram shown in FIG. 17 was obtained.

Figure 17:
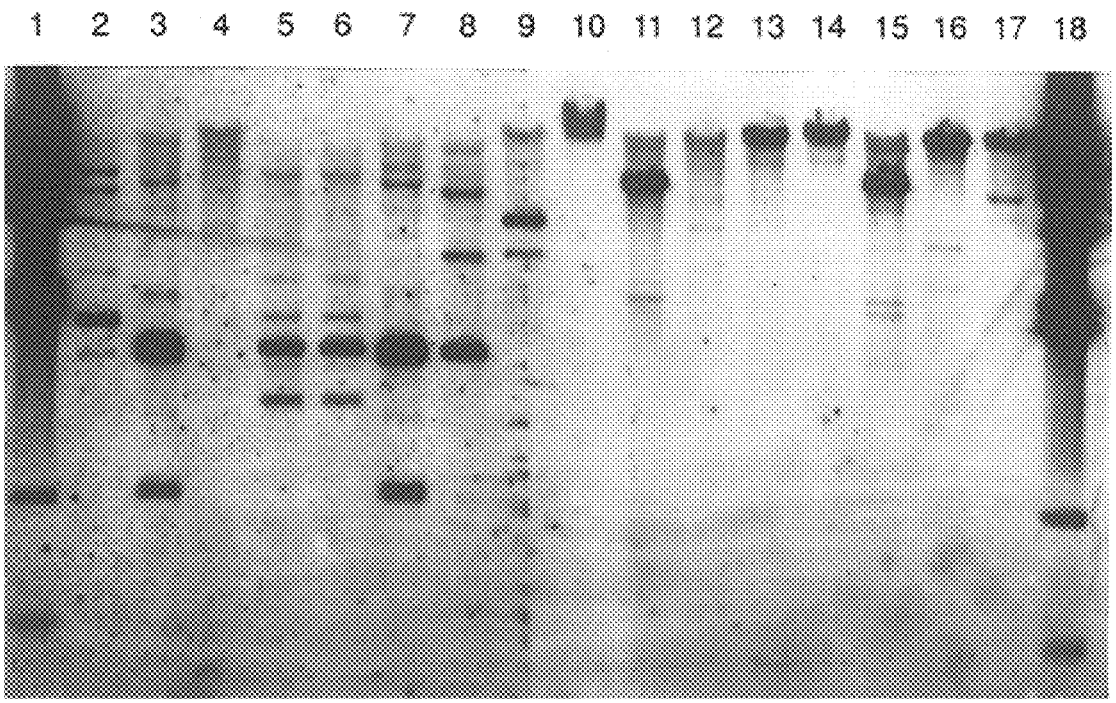
FIG. 17. Homologs of tap are present in many Streptomyces strains.

The autoradiogram showed hybridizing bands in all lanes except those containing S. fradiae DNA. Lanes 1 and 18 contained Lambda/HindIII molecular weight markers. In FIG. 17, lanes 2 and 10, S. alboniger; lanes 3 and 11, S. coelicolor; lanes 4 and 12, S. fradiae; lanes 5 and 13, S. griseus IMRU 3499; lanes 6 and 14, S. griseus ATCC 10137; lanes 7 and 15, S. lividans 66; lanes 8 and 16, S. parvulus; lanes 9 and 17, S. rimosus.

Identical hybridizing bands were observed with S. lividans and S. coelicolor with a common band in both S. griseus strains as well as the S. parvulus DNA. S. rimosus and S. alboniger produced hybridizing bands at different molecular weights suggesting restriction fragment length differences in these species. No strong band was observed for the S. fradiae DNA. Taken overall the results suggested that the Tap-encoding DNA sequence occurs widely throughout the Streptomyces strains examined.

In a similar experiment using S. ambofaciens ATCC 23877 DNA, strongly hybridizing bands were observed after digestion with BamHI, PstI, SacI, and SalI. This indicated the likely presence of a tap gene in S. ambofaciens which would be expected to be detrimental to product yield when expression of secreted proteins is desired in this strain.

The following examples relate to proteases, other than Tap, derived from Streptomyces, their DNA sequences and amino acid sequences. These proteases degrade certain substrates under certain conditions. Example 20 describes one such protease, which displayed a significant amino acid sequence homology with the Bacillus subtilis protease BPN' (using the BLAST program [Altschul et al] to screen the protein sequence databases) and was therefore designated Ssp (Subtilisin-like-protein). An improved strain of Streptomyces in which this protease is impaired, was created. Southern blot hybridization indicated that Ssp is present in many Streptomyces species. Three other proteases, the DNA sequences and deduced amino acid sequences for two of them, are described in Examples 21, 23 and the n-terminal amino acid sequence of the third protease is indicated in Example 22.

Example 20

Characterization of P5-4 and P5-15.

Following the teaching of Example 10, the S. lividans 66 genomic library was used to transform protoplasts of the MS7 mutant strain. Transformant colonies were screened with the substrate APA-bNA. Among the thirteen thousand colonies screened, two clones were isolated by virtue of the plasmid-encoded phenotype (colonies appeared red against a background of pale colonies). Plasmid DNA was isolated from these colonies and used to transform E. coli competent cells from which larger quantities of plasmid DNA were isolated.

Figure 18:
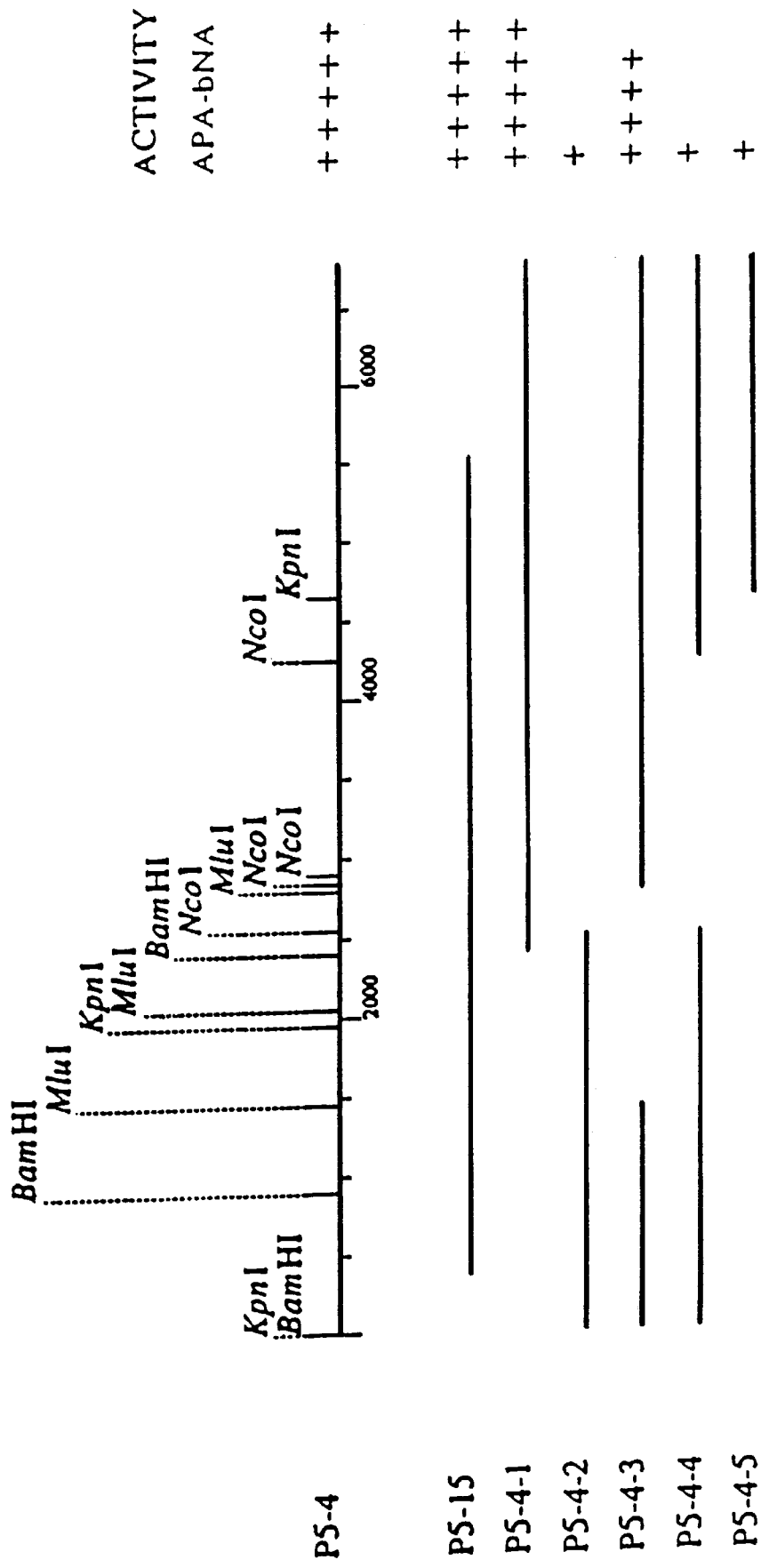
FIG. 18. Common restriction map for P5-4 and P5-15 and their deletion clones.

Restriction enzyme site mapping established that two clones (designated P5-4 and P5-15) were shown to represent overlapping fragments of S. lividans chromosomal DNA containing the Ssp-encoding gene. FIG. 18 shows the restriction enzyme sites present in the P5-4 and P5-15 DNA. K=KpnI, B=BamHI, M=MulI. The hydrolytic capabilities of strains containing the cloned DNA (or deletions thereof) was measured visually using the agar plate assay method. Southern hybridization against chromosomal DNA showed the expected pattern of hybridizing bands indicating that no major DNA rearrangements had occurred during the isolation of these clones.

Following the teaching of Example 15 the region of DNA encoding the proteolytic activity was defined within the deletion clones P5-4-1 and P5-4-3 (FIG. 18). Specifically, the larger of the two NcoI fragments deleted in P5-4-2, P5-4-4 and P5-4-5 appears to be correlated with the proteolytic activity.

Figure 19:
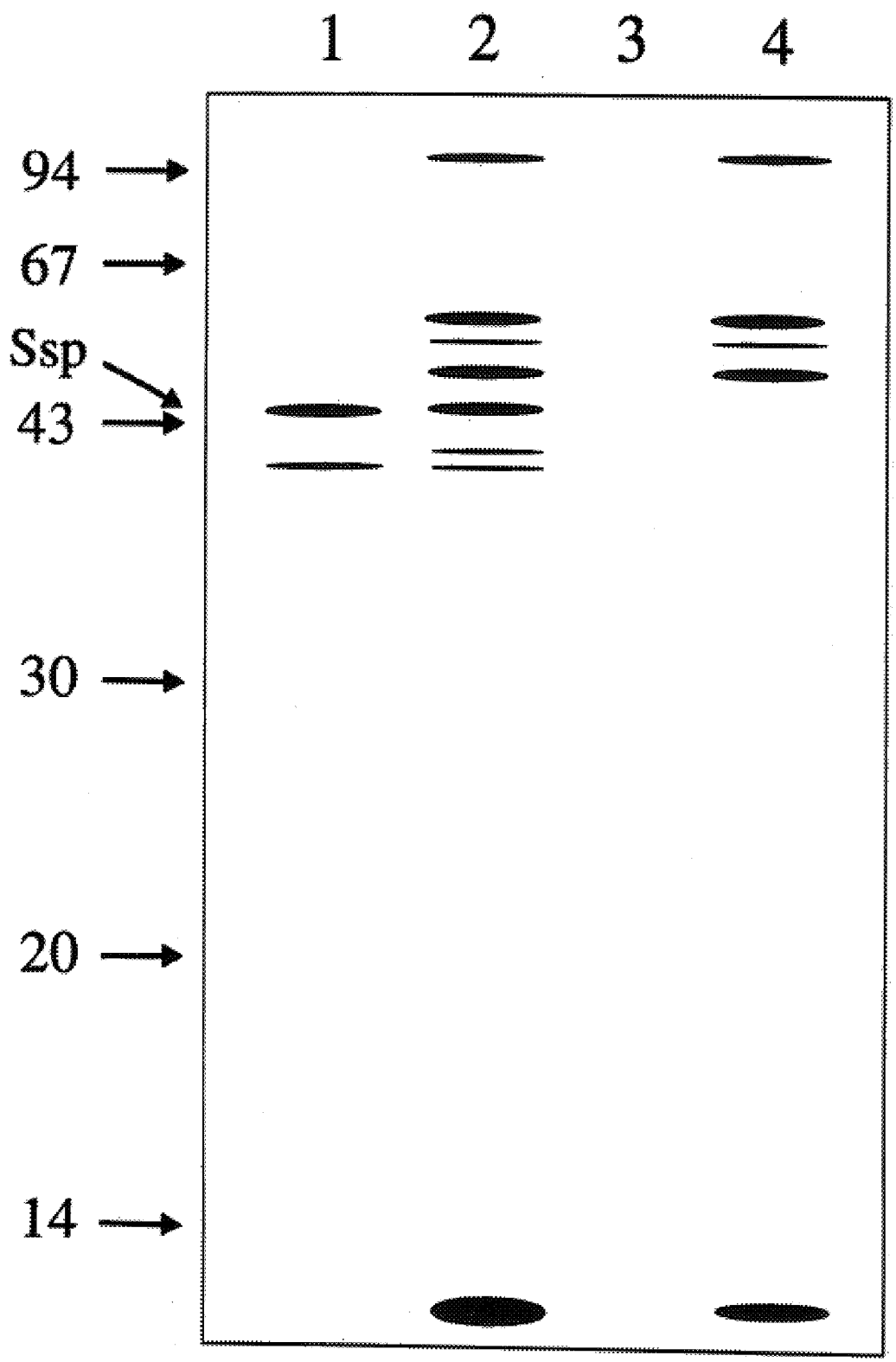
FIG. 19. SDS-PAGE resolution and silver staining of proteins secreted in a fermentation culture containing the P5-4 plasmid DNA.

FIG. 19 shows SDS-PAGE analysis of protein secreted by strains carrying the P5-4 DNA (Lanes 1 and 2) or the P5-4-4 deletion clone (Lanes 3 and 4). Lanes 1 and 3 contained 30 µl of cell-free broth. Lanes 2 and 4 contained approximately 2 µg protein derived from the cell-free broth samples by ammonium sulphate precipitation. The positions of molecular weight marker are shown by arrows. A major protein species was observed at a position consistent with a molecular weight of approximately 45,000. Preparative SDS-PAGE followed by electrotransfer to PVDF membrane (as described in Example 13) allowed direct automated Edman degradation to be carried out to yield the amino acid sequence (SEQ ID NO:22) NH$_2$-Asp-Thr-Gly-Ala-Pro$^5$-Gln-Val-Leu-Gly-Gly-$^{10}$-Glu-Asp-Leu-Ala-Ala-$^{15}$-Ala-Lys-Ala-Ala-Ser$^{20}$-Ala-Lys-Ala-Glu-Gly$^{25}$-Gln-Asp-Pro-Leu-Glu$^{30}$.

DNA sequence analysis (shown in FIGS. 20A–20C) of the P5-4 DNA revealed a potential protein coding region located within the region of DNA defined by the two NcoI fragments in FIG. 18. This was consistent with the respective activities of the plasmid deletion clones P5-4-1, P5-4-2, P5-4-3, P5-4-4 and P5-4-5. Inspection of the predicted protein sequence reveals the exactly matching, experimentally determined amino terminal amino acid sequence noted above. Furthermore, the predicted amino acid sequence also shows a putative signal sequence at the amino terminus, followed by a putative pro region defined by the amino terminal end of the experimentally determined mature amino acid sequence.

Figure 30:
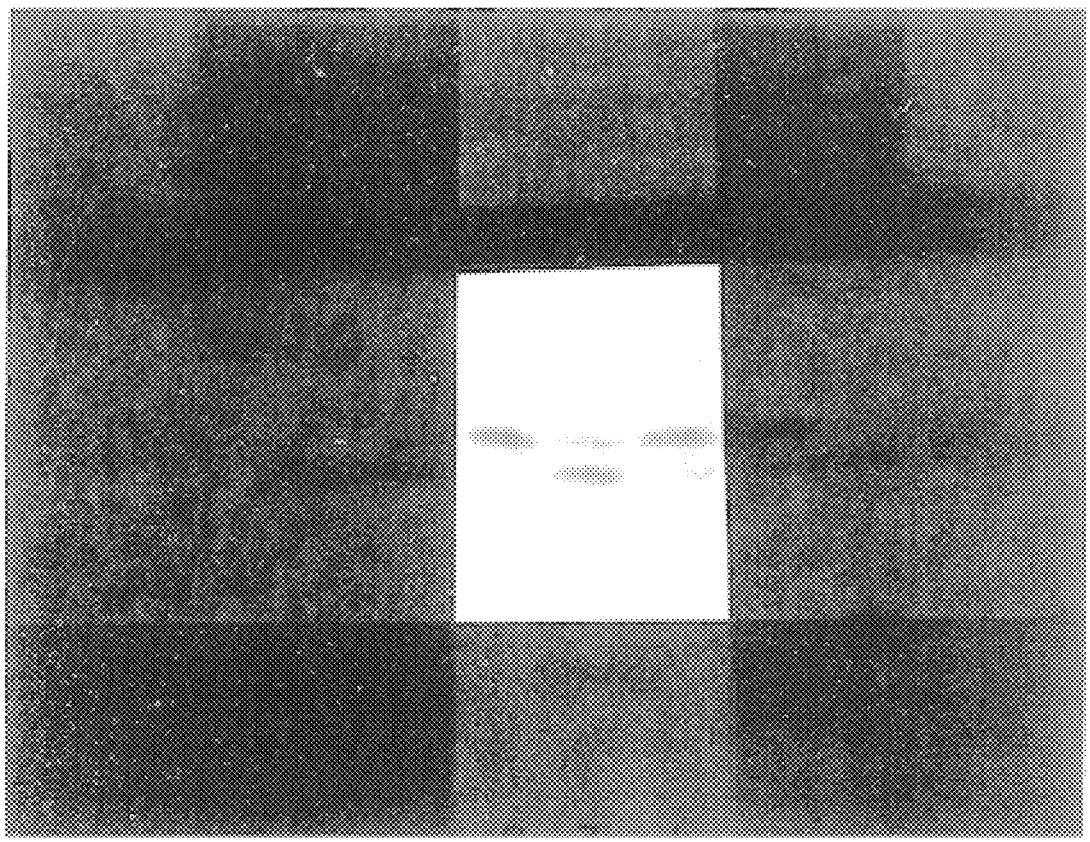
FIG. 30. Conversion of an intact substrate GM-CSF to its "-3 form" upon incubation with fermentation culture supernatants from cells carrying P5-4, P5-10 and P5-15.

FIG. 21 shows a comparison of the amino acid sequence of the proteins predicted from the P5-4 DNA sequence with that of the Bacillus protein subtilisin BPN. 1 designates the S. lividans sequence while 2 designates the Bacillus sequence. GM-CSF degradation assays according to methods used in Example 2 using cell-free broth from S. lividans MS7 strain carrying the P5-4 plasmid DNA culture in TSB medium demonstrated that the overproduced Ssp also degraded GM-CSF. In FIG. 30, lane 1 shows such GM-CSF degradation by a P5-4-containing MS7 strain; lane 3 shows a similar result with a P5-15-containing MS7 strain. In contrast, lane 2 shows broth from a P5-10 culture which shows only slight degradation to the "-3 form". The same results were obtained with samples from cultures carrying only the PSS12 plasmid.

Deletion of the Ssp-encoding DNA from the S. lividans chromosome was accomplished following the teaching of Example 16. Specifically, the DNA from plasmid deletion clone P5-4-4 (FIG. 18) was subcloned into pT7T3 using the EcoRI site immediately adjacent to the leftward side of the DNA insert (shown in FIG. 18). Since there was no convenient restriction enzyme site to the rightward side of the DNA insert this was excised using the XhoI site (in the replication origin of the plasmid vector, pSS12) which was subsequently ligated to the SalI-digested pT7T3. Hence, overall the EcoRI-XhoI fragment was inserted in EcoRI and SalI digested T7T3 DNA. The fragment was subsequently excised by digestion with EcoRI and HindIII and inserted into the integration vector, pINT using the same restriction enzyme sites. The pT7T3 intermediate step was required because the SalI site in the multiple cloning site of pINT was not unique and, therefore, not convenient for subcloning purposes.

This integration clone was used to create strains containing the specific deletion at the ssp locus in two S. lividans host strains. Firstly, the MS7 host strain was used to create a new strain designated MS11 (pepP1⁻, pepP2⁻, slpA⁻, slpC⁻, tap⁻, ssp⁻). Secondly, another tap-deleted strain (MS9) was used to create MS12 (tap⁻, ssp⁻). The deletion strains MS7, 9, 11 and 12 were cultured in TSB/PPG liquid medium for 22 hours and examined for the ability of cell-free broth to hydrolyse APA-pNA.

Figure 22:
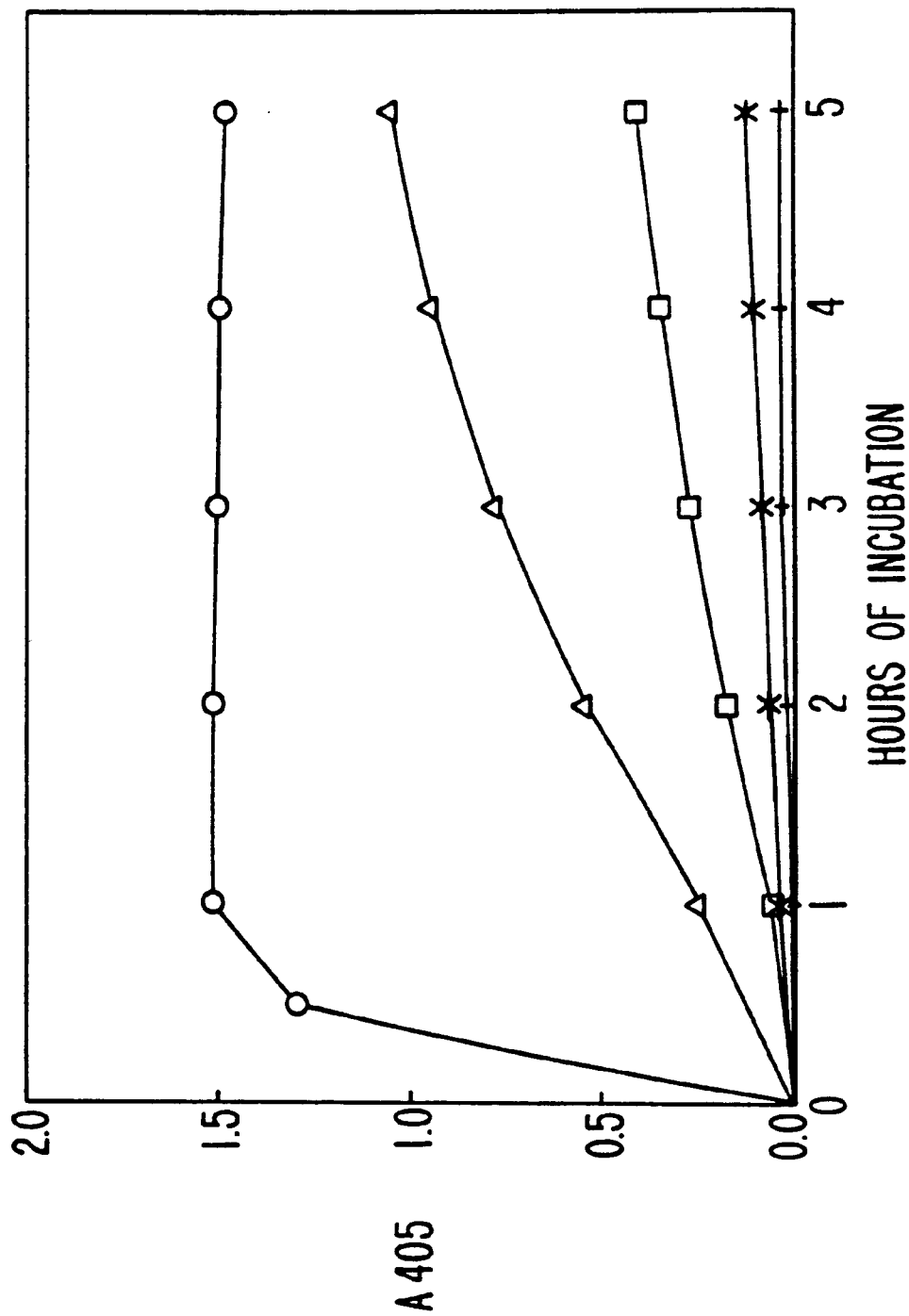
FIG. 22. Proteolytic activity of *S. lividans* deletion strains using the substrate APA-pNA.

FIG. 22 shows the activity of cell-free broth samples derived from S. lividans 66 (-○-), MS7 (-Δ-), MS9 (-□-), MS11 (-*-) and MS12 (-+-) strains against the APA-bNA substrate according to the teaching of Example 2.

The results (FIG. 22) showed a reduction in hydrolytic capability with the MS12 strain showing the lowest activity. All the strains displayed a significantly reduced hydrolytic capability compared to S. lividans 66 but the MS9 strain showed a lower level than the MS7 strain. (This was shown in a separate experiment not to be due to the different integration clones used, since MS8 used the same integration clone as MS7 but was derived from S. lividans 66 protoplasts and showed indistinguishable properties to MS9).

Figure 23:
FIG. 23. Homologs of the P5-4 DNA are present in the chromosomal DNA of many Streptomyces strains.

Southern hybridization experiments detected DNA sequences homologous to the ssp DNA in many Streptomyces species. FIG. 23 shows a Southern blot hybridization experiment using the 2.25 kb EamHI—KpnI DNA fragment which had been subcloned into pT7T3.18μ. Lanes 1 and 18 are lambda/HindIII molecular weight markers. Lanes 2 to 9 represent chromosomal DNA digested with NcoI while lanes 10 to 17 show DNA digested with SphI. Lanes 2 and 10, S. alboniger; Lanes 3 and 11, S. ambofaciens; Lanes 4 and 12, S. coelicolor; Lanes 5 and 13, S. fradiae; Lanes 6 and 14, S. griseus; Lanes 7 and 15, S. lividans 66; Lanes 8 and 16, S. parvulus; Lanes 9 and 17, S. rimosus.

It should be noted that the same library of clones was screened as in Example 10. Presumably, the lower background level of APA-bNA-hydrolysing activity in MS7 (compared to S. lividans) allowed the P5-4 and P5-15 clones to be identified. This has been noticed by other workers particularly relating to neutral protease activities in B. subtilis (Sloma et al., 1990).

Example 21

A Protease Encoding Gene, P5-6 and a Predicted Protein

Following the teaching of Example 21 yet another protease-encoding gene was isolated from the same library screening experiment. Two clones were identified as being different (in terms of restriction enzyme sites) from the tap or ssp clones described in this application. Clone numbers P5-6 and P5-17 were shown to represent overlapping fragments of chromosomal DNA (FIG. 24).

Figure 24:
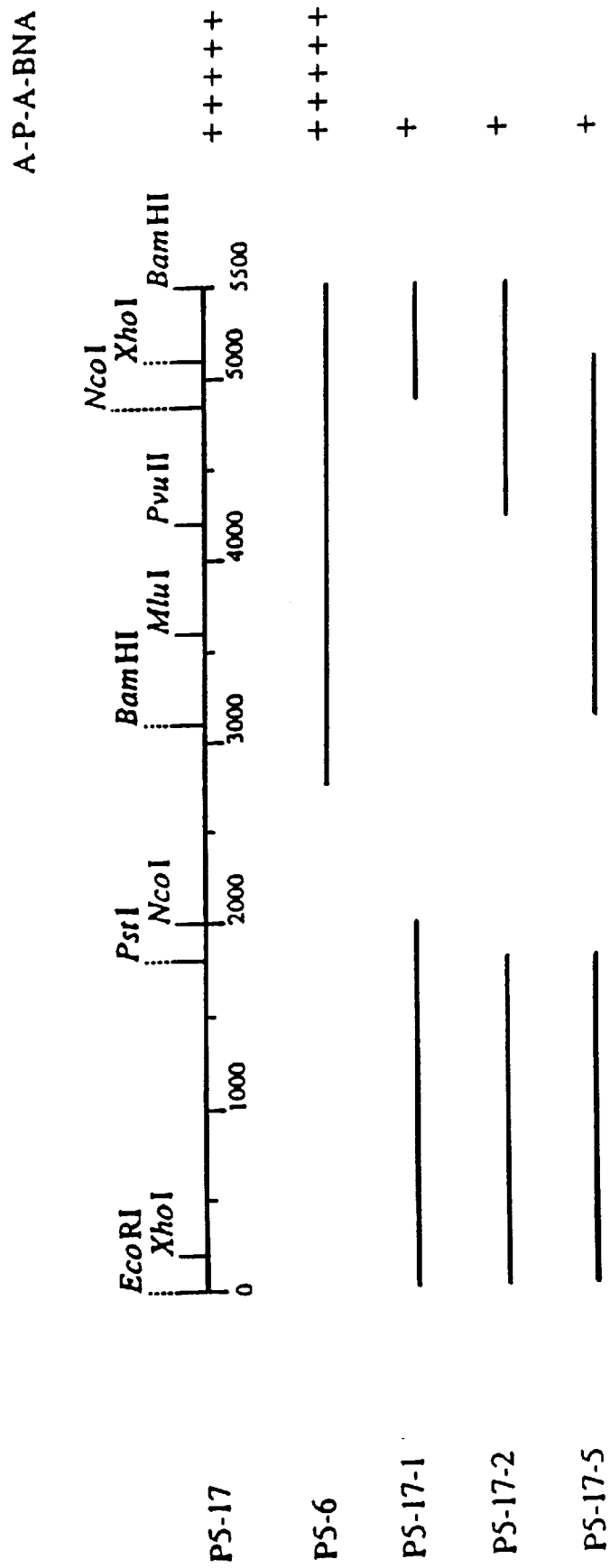
FIG. 24. Common restriction map for P5-6 and P5-15 and their deletion clones.

FIG. 24 shows the common restriction enzyme site map of the P5-6 and P5-17 DNA and deletion clones derived from P5-17. Activity against APA-bNA is shown by the number of asterisks adjacent to each plasmid and was estimated using the agar plate assay method described in Example 10.

Figure 31:
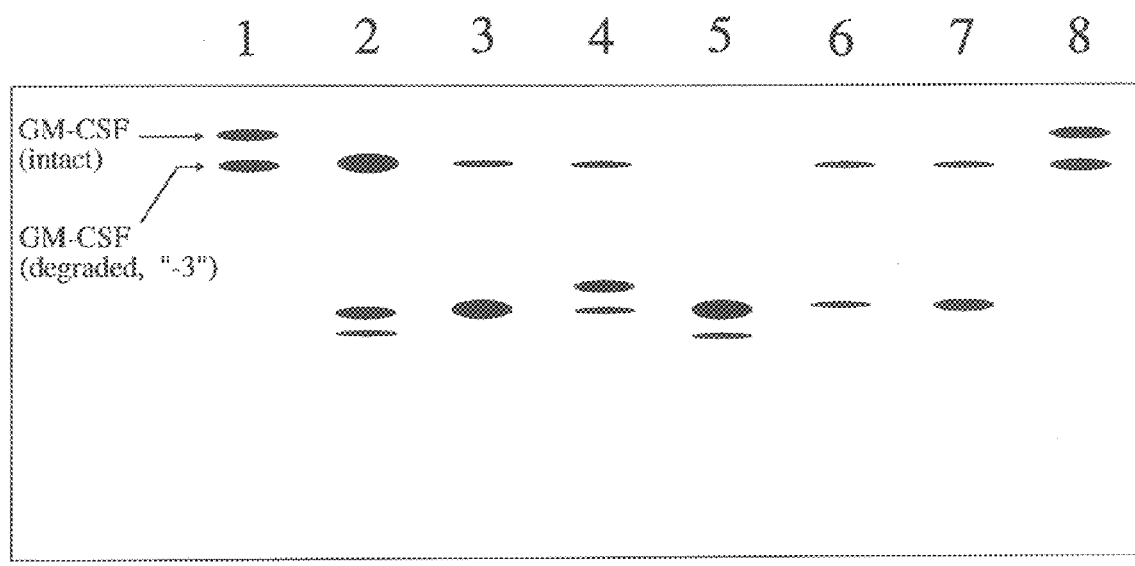
FIG. 31. Conversion of an intact GM-CSF to its "-3 form" upon incubation with fermentation culture supernatants from cells carrying P5-6, P5-10 and P5-17.

Although these clones encoded significant hydrolytic capability against the APA-bNA substrate in the agar plate assay, no activity above background was observed in cell-free broth derived from cultures containing these plasmids grown in TSB media. Neither was it possible to experimentally identify the protein product of this locus. When cultured in liquid medium resembling the agar medium composition (i.e. R2 without added phosphate or agar and containing 0.25% yeast extract—instead of the usual 0.5%) APA-bNA-degrading activity was observed in the cell-free broth. However, in contrast to the Tap and Ssp proteins, this activity was unable to hydrolyse GPL-bNA in R2, although it did show degradation of full-length GM-CSF according to the methods described in Example 2 (FIG. 31, lanes 3 and 7).

Figure 26:
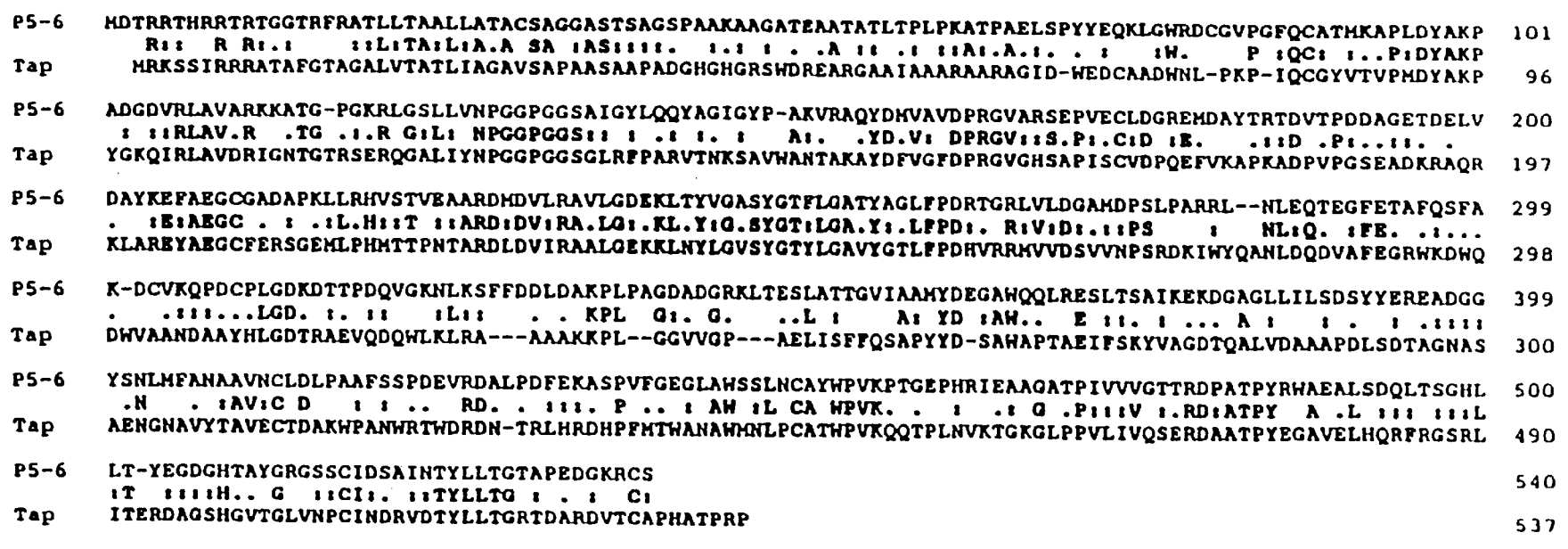

DNA sequence analysis of the P5-6 DNA (FIGS. 25A–25C) revealed a potential coding region. The predicted protein once again displayed a putative secretion signal peptide, followed by a predicted protein of 492 amino acid residues (FIGS. 25A–25C). Furthermore, when the amino acid sequence was compared to that of the Tap (FIG. 26) a strong homology was obvious around the region encoding the putative active site serine residue.

Plasmid deletion clones were constructed from P5-17 and shown to encode no activity above background in the agar plate assay.

Example 22

Characterization of P5-10

Figure 27:
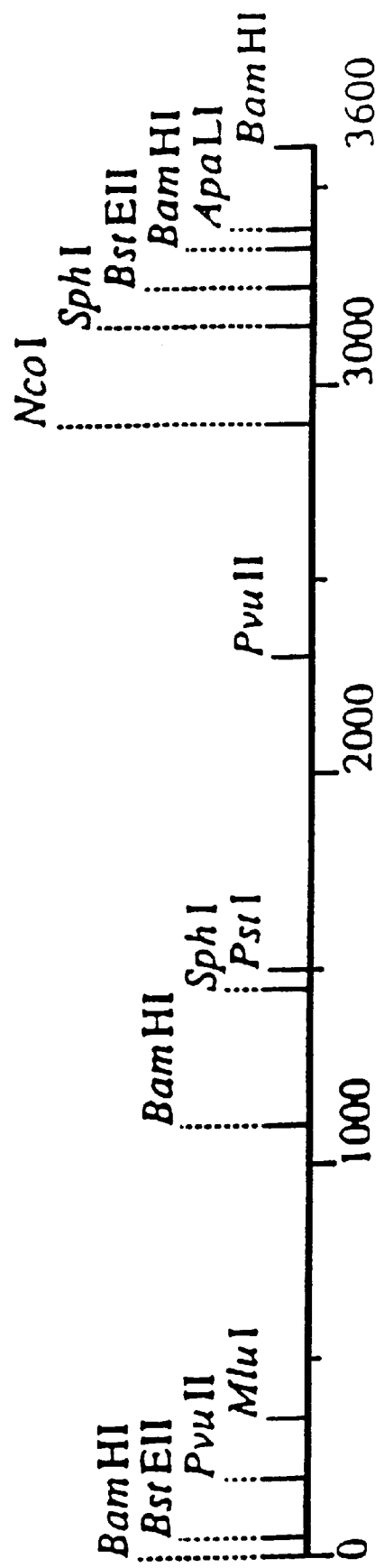
FIG. 27. Restriction map of P5-10 DNA.

Another cloned DNA fragment was isolated from the same APA-bNA screening experiment described in Examples 20 and 21. This DNA species was designated P5-10 and showed a different pattern of characteristic restriction enzyme sites (FIG. 27) than those observed for the other clones described above. A significant protein band was observed by SDS-PAGE analysis of supernatants of strains carrying this plasmid. Its molecular weight is approximately 50,000 daltons. Amino terminal amino acid sequence analysis was carried out according to the teaching of Example 13 yielding the following sequence (SEQ ID NO:13): Ala-Glu-Pro-Xaa-Ala⁵-Val-Asp-Ile-Asp-Arg¹⁰-Leu. The activity of supernatant material containing this protein from MS7 host cultures, grown in TSB medium, was very low against APA-bNA and GPL-bNA. However, when cultured in R2YE liquid medium a high level of activity was observed against APA-bNA but not GPL-bNA. Furthermore, degradation of full-length GM-CSF according to the methods described in Example 2, was also detectable in samples grown in R2YE but not TSB (FIG. 31, lane 5).

Example 23

Characterized of P8-1, 2 and 3

A chromogenic substrate was designed to model the amino terminal region of GM-CSF except that the amino terminal residue was modified by the addition of a Boc-group (or other similar moieties such as Fmoc), such that proteases whose activity requires a free NH$_2$-group would be unable to act directly on this substrate. However, any endoprotease present in the S. lividans host having a recognition sequence compatible with that of the substrate (SEQ ID NO:15) (specifically Boc-APARSPA-bNA) would be able to cleave and remove the Boc-group in addition to some portion of the peptide. Such cleavage would generate a smaller peptide-linked bNA moiety which now contains a free $NH_2$-group at the N-terminus and can be acted upon to release the chromogenic bNA moiety which can subsequently be visualized by reaction with Fast Garnet GBC dye.

Figure 28:
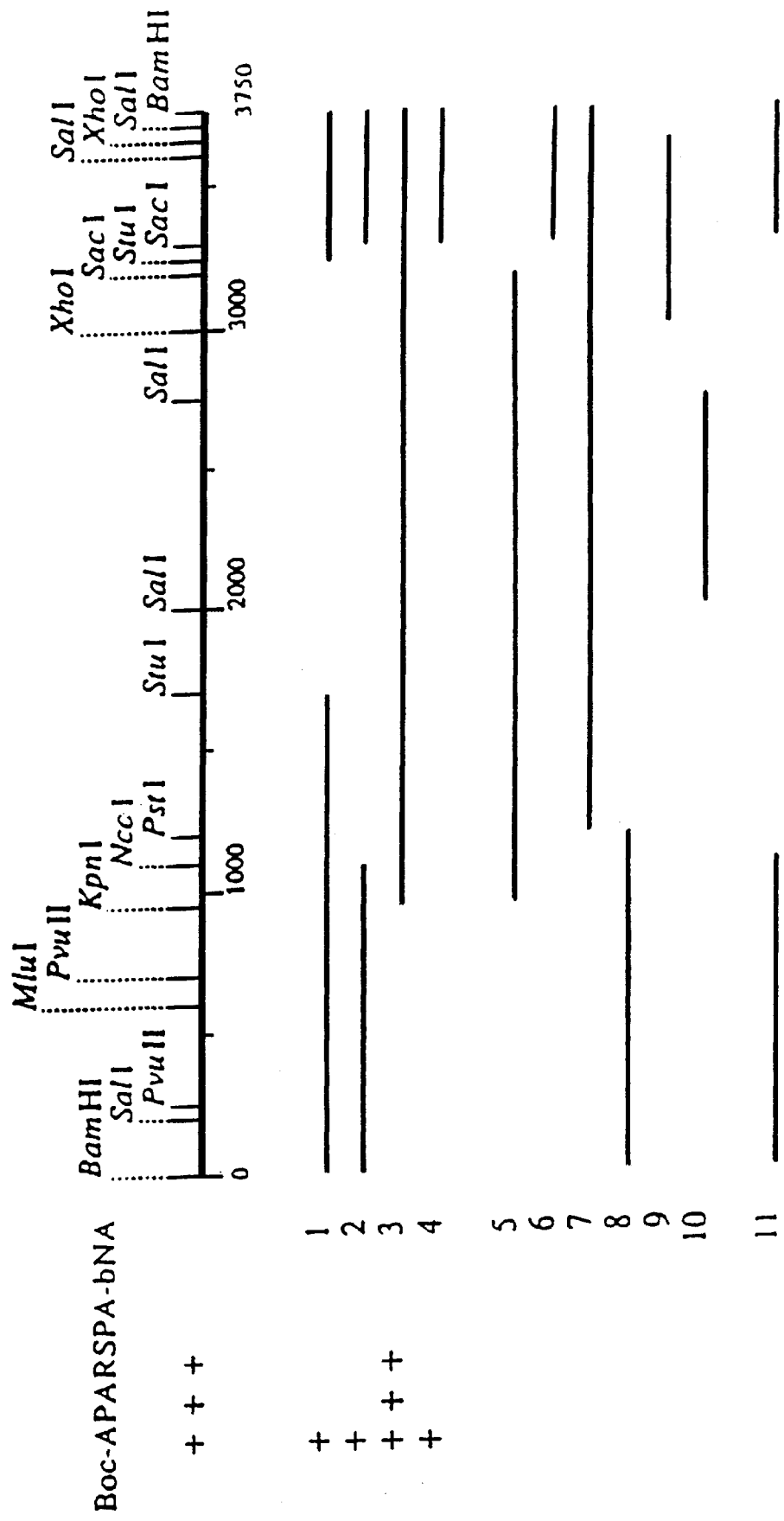
FIG. 28. Restriction map of P8-2 and its deletion clone.

This strategy was used to screen the S. lividans 66 genomic DNA library after transformation into the MS5 host strain (tap+). After screening of eight thousand colonies, six clones were confirmed to encode the ability to degrade the substrate significantly faster than the host strain alone. Two clones proved on restriction enzyme site analysis to be identical to P5-6 described in Example 21. Another clone was similarly shown to be the same as P5-17. Three other clones (P8-1, 2 and 3) were isolated and shown to represent the same region of chromosomal DNA (by Southern hybridization experiments). P8-3 contained a larger DNA fragment which was probably derived from the cocloning of non-contiguous Sau3AI fragments in the construction of the library. P8-1 contained an inserted DNA fragment of approximately 8 kbp, while P8-2 had a smaller insert (3.6 kbp). Deletion mapping and DNA sequence analysis revealed a potential protein coding region in the central part of the cloned DNA (FIG. 28.) Comparison of the predicted protein sequence derived from the DNA sequence (FIGS. 29A–29C) with those encoded by the tap and P5-6 clones showed a significant homology between the proteins encoded by P8-2 and P5-6. A smaller but still significant homology was detectable with the Tap protein. Specifically of interest is the conservation of amino acid sequences around the putative active site serine residues of these proteins as follows (SEQ ID NOS 23–25, respectively):

Tap—GVSYGTYLGAVYGTLFPDHVRR
P5-6—GASYGTFLGATYAGLFPDRTGR
P8-2—GISYGTELGGVYAHLFPEHVGR

Example 24

An Immunoassay Using Tap

Tap as a unique protease with a well established assay using a synthetic substrate for determination of its activity (described in this patent application) may be applied as a useful tool for immunoassay.

The uses of high performance immunoassay have increased greatly in the last decade, extending to almost every discipline in the life sciences. In the majority of applications, antibodies are labelled with enzymes, biotin or fluorochromes, and serve as components of a signal generating/amplifying system. This technology has a broad applicability and can be used in a wide variety of laboratory techniques including enzyme-linked immunosorbent-assay (ELISA), immunoblotting, immunohisto/cytochemistry and immuno- electrophoresis. In the following example we will show how one can use Tap in the most widely used technique—microwell ELISA.

In microwell ELISA, antigens are immobilized in a microwell and probed by labelled antibody (conjugate). The enzyme-labelled reagents are detected with the appropriate substrate, which is converted to a visible colored product at the reaction site. The intensity of color produced is proportional to the amount of measured antigen.

To date, the most common enzymes used for generating color are alkaline phosphatase or horseradish peroxidase. In this example, those enzymes are replaced with Tap and using the synthetic substrate, developed and described in this patent application, such as APA-pNA for visible color and APA-AMC for fluorescence technology detection.

To demonstrate this idea, IL-3 was used as an example for antigen quantitation. Rabbit anti-IL-3 antisera (Cangene Corporation, Canada) was used as the first antibody. The second antibody, goat anti-rabbit IgG linked to biotin (Sigma, St. Louis, U.S.A.), and streptoavidin (Boehringer Mannheim GmbH) were used as the amplification system. Tap linked to biotin was used as the enzyme. The Tap was purified as described in Example 1 and 9.0 mL of the Tap (approximately 0.3 mg/mL) were biotinylated with D-Biotinyl-E-aminocaproic acid N-hydroxysuccinimide ester as described in Biochemia Bulletin of Boehringer Mannheim (1989, Antibodies and Reagents for Immunochemistry, p.115). Serial dilutions of recombinant hIL-3 (Cangene Corporation, Canada) were applied to the microplate wells (100 µL/well), and then incubated at 4° C. for over 16 hours. The wells were then washed and 5% BSA (bovine serum albumin) was added as a blocker. After 1 hour incubation, the wells were washed and rabbit anti hIL-3 sera (Cangene Corporation, Canada) was added at a dilution of 1/2000. Incubation was performed at 37° C. for 1 hour. The wells were then washed and the second antibody, goat anti-rabbit IgG-Biotin (Sigma), was added at a dilution of 1/2000 for 1 hour at 37° C. After washing, a mixture of Streptoavidin and Biotin-Tap was added. This mixture was prepared previously as follows: 40 µL of Streptoavidin (Boehringer Mannheim, 1 mg/mL) and 35 µL of Biotin-Tap were added to 5 mL Tris buffer pH 8.0 containing 1% BSA. The mixture was pre-incubated for 45 minutes before being added to the microplate assay. The mixture was washed from the microplate after incubation for 45 minutes at room temperature. Then 100 µL of the enzyme substrate (0.8 mM) were added. For color developing, APA-pNA was used as a substrate and the assay was read after 2 and 16 hours incubation by absorbance at 405 nm. For faster analysis, APA-AMC was used as a fluorescent substrate, where the incubation was performed for 30 minutes and the assay was analyzed at exitation/emission of 400/450 nm by the multiwell plate scanning fluorescent system.

Figure 32A:
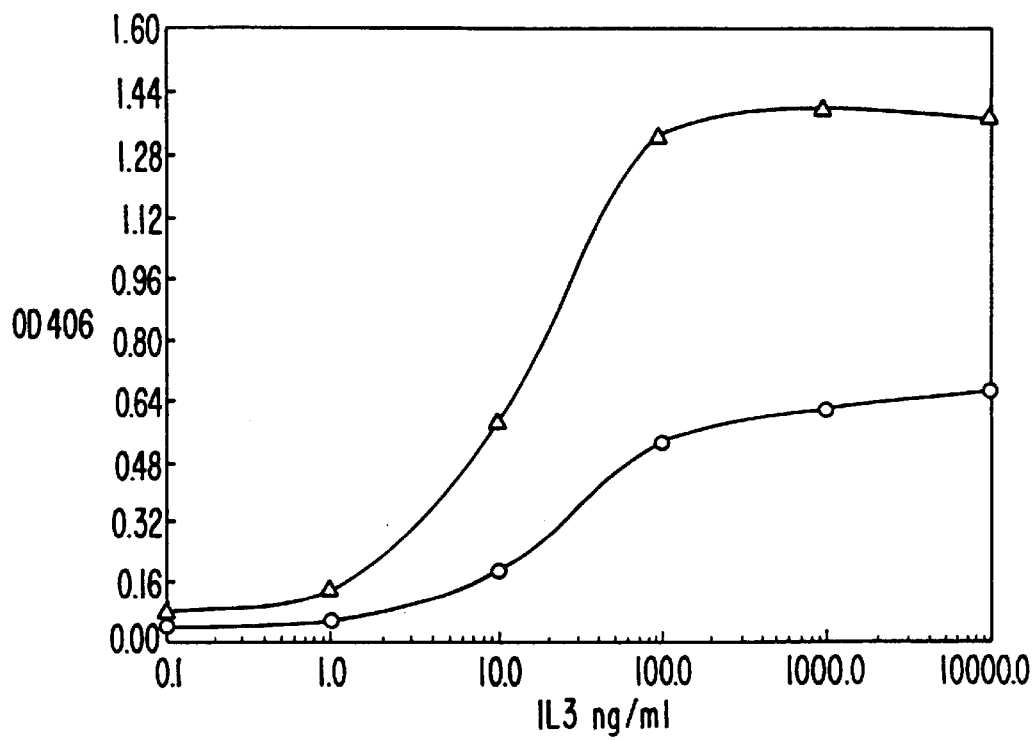
Figure 32B:
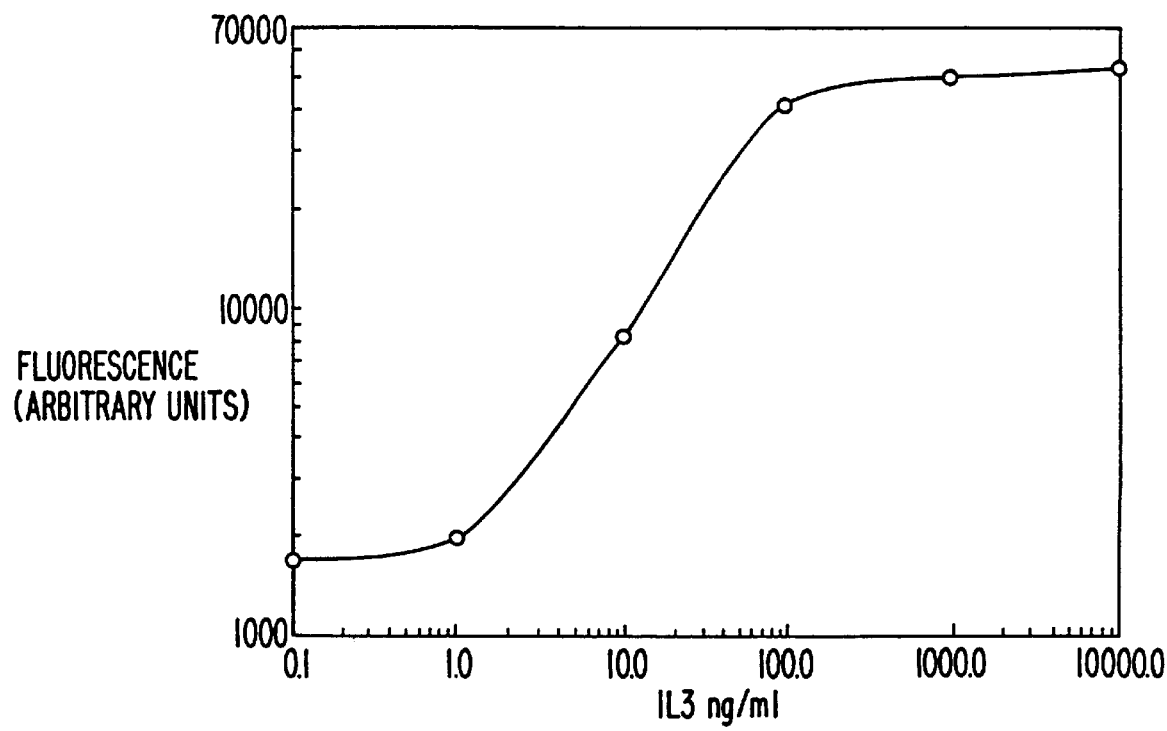

FIGS. 32A–32C shows a hIL-3 calibration curve using ELISA technology with Tap as the enzyme and APA-pNA as the substrate for color forming (Panel A) incubated for either 2 hours (o---o) or 16 hours (Δ---Δ), and APA-AMC as a fluorescent substrate (Panel B) incubated 30 minutes.

There are some advantages to using Tap in the ELISA system compared to the common enzymes. The substrates for Tap are much more stable and simple. The reaction can be incubated much longer and can be measured anytime without stopping the reaction. If necessary, the reaction can be stopped specifically by APA-CMK. Tap activity is not affected by peroxidases, catalases, phospatases, chelators, or sodium azide which may interfere with common ELISA enzymes. Using Tap in ELISA does not compromise the sensitivity and may even increase sensitivity by using fluorescent substrate.

Example 25

Secretion of Soluble Forms of the Enzymes Encoded by P5-6 and P8-2

No extracellular hydrolytic activity could be observed in liquid cultures of strains carrying the cloned P8-2 DNA sequence of FIG. 28 even when modified R2 liquid medium was used. Moreover, SDS PAGE analysis with silver staining could not detect extracellular proteins of the anticipated sizes in modified R2 liquid cultures of *S. lividans* MS7 carrying the cloned DNA sequences of FIG. 25 (eg. P5-6) or FIG. 28 (eg. P8-2). Although the strains carrying these cloned DNA sequences clearly exhibited hydrolytic activities against their respective substrates on modified R2 agar plates, significant levels of these activities could not be localized to either the intracellular or extracellular fractions.

Consistent with these observations, the amino termini of the potential coding regions of P5-6 and P8-2, unlike conventional signal peptides, contain sequences which match well with the signal peptidase II consensus sequence characteristic of lipoproteins. As predicted by von Heijne (1989), the signal peptidase II processing would precede the cysteines in the sequence LATACSAGGAS of P5-6 (FIGS. 25A–25C) and LTAGCSGGSS of P8-2 (FIG. 28). Each sequence shows a striking clustering of turn-producing amino acids following the cysteine, consistent with the amino termini of lipoproteins. The highly positively charged amino terminus of the potential coding region of P5-6, with 7 arginines and a single aspartate, is commonly found on other Gram positive signal peptides. Overall, the amino-terminal sequences for the potential coding regions of P5-6 and P8-2 are consistent with membrane bound forms of each enzyme, designated SlpD and SlpE, respectively.

In order to allow biochemical purification of the predicted proteins from culture supernates, to examine their hydrolytic capabilities and to confirm that the predicted proteins are directly responsible for these activities, the nucleotides encoding both the putative promoter region and the lipoprotein signal peptide including the +1 cysteine were replaced by sequences encoding the aminoglycoside phosphotransferase (aph) promoter and the protease B signal peptide (Henderson et al., 1987). Also, a small leader peptide was added to the C-terminus of the protease B signal peptide which preceded the sequences coding for the SlpD and SlpE proteins. This was accomplished by the use of oligonucleotides to adapt the protease B signal peptide at its C-terminal coding region with the leader and a cloning site, and to adapt the SlpD and SlpE proteins at their N-termini with appropriate cloning sites.

Figure 33A:
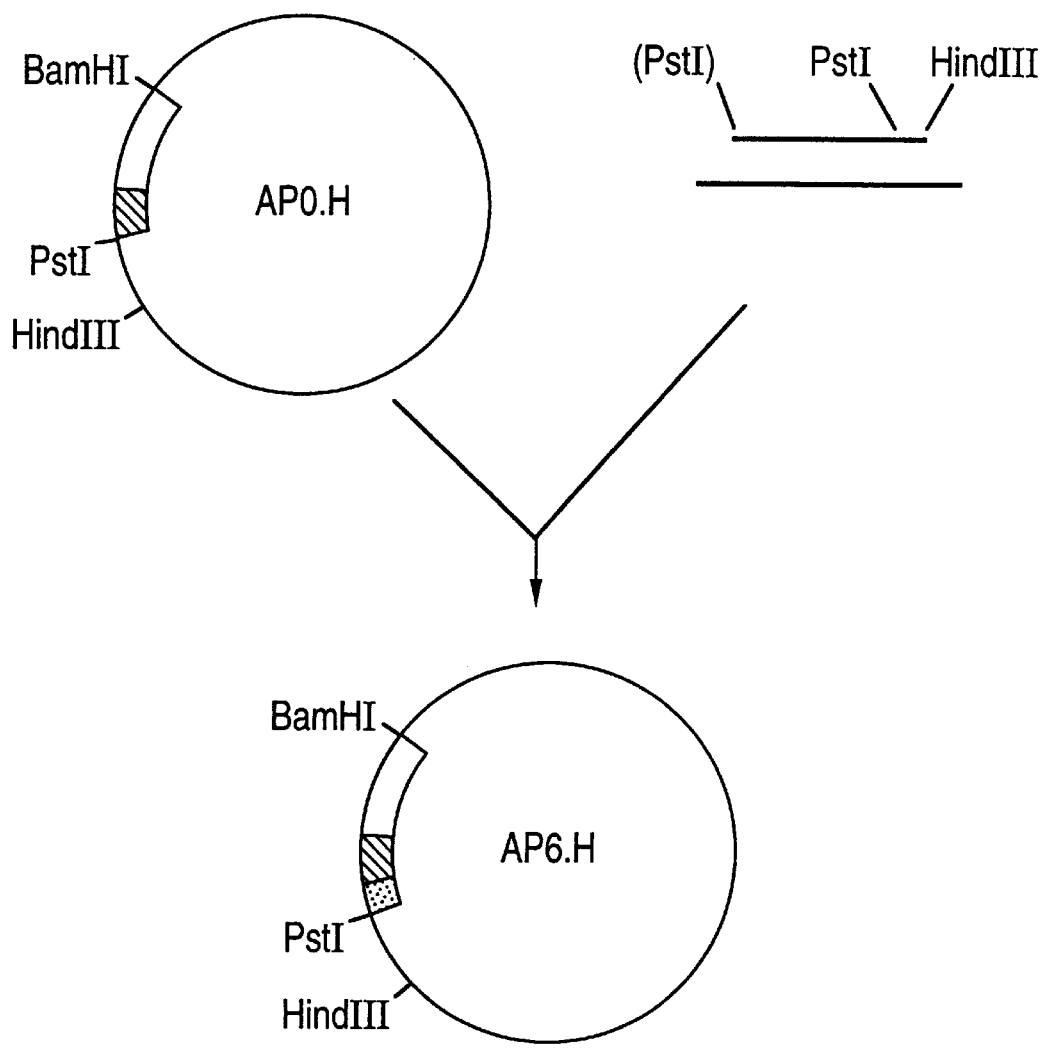
FIG. 33A. The AP6.H vector.

To adapt the C-terminus of the protease B signal peptide, a Streptomyces expression vector (APO.H) containing the aph promoter followed by the protease B signal peptide (Garven and Malek, U.S. Pat. No. 5,200,327), was used. It contained an NsiI cloning site at the 3' end of the protease B signal, with an internal GCA codon encoding the −1 Ala of the protease B signal. A HindIII site was located adjacent to the NsiI site. Oligonucleotides encoding a smaller leader peptide were inserted at the 3' end of the protease B signal peptide by the digestion of APO.H with NsiI and HindIII, then insertion of this pair of oligonucleotides with complementary base extensions to the NsiI and HindIII sites. These oligonucleotides encoded six amino acids (SEQ ID NO:14) (APAAPA), with an internal PstI cloning site containing a GCA codon at the last Ala of the leader to allow subsequent insertion of the N-termini of the sequences encoding sIpD and sIpE downstream of this leader. This modified vector was designated AP6.H (See FIG. 33A).

To adapt the N-terminus of the SlpD protein, oligonucleotides encoding the 11 amino acids of SlpD immediately downstream of the SPase II +1 cysteine were synthesized. An EcoRl cloning site at the 5' end allowed for ligation of the oligonucleotides into the EcoRI site contained within the polylinker of a T7T318U based subclone (#4) of SlpD clone p5-6. This subclone also contained a HindIII site from the polylinker located 380 nucleotides downstream of the SlpD stop codon. The oligonucleotides also contained at their C-terminus a BamH I site, which joins to a natural BamHI site within the SlpD encoding sequence, located 30 nucleotides downstream from the SPase II +1 cysteine.

Figure 33B:
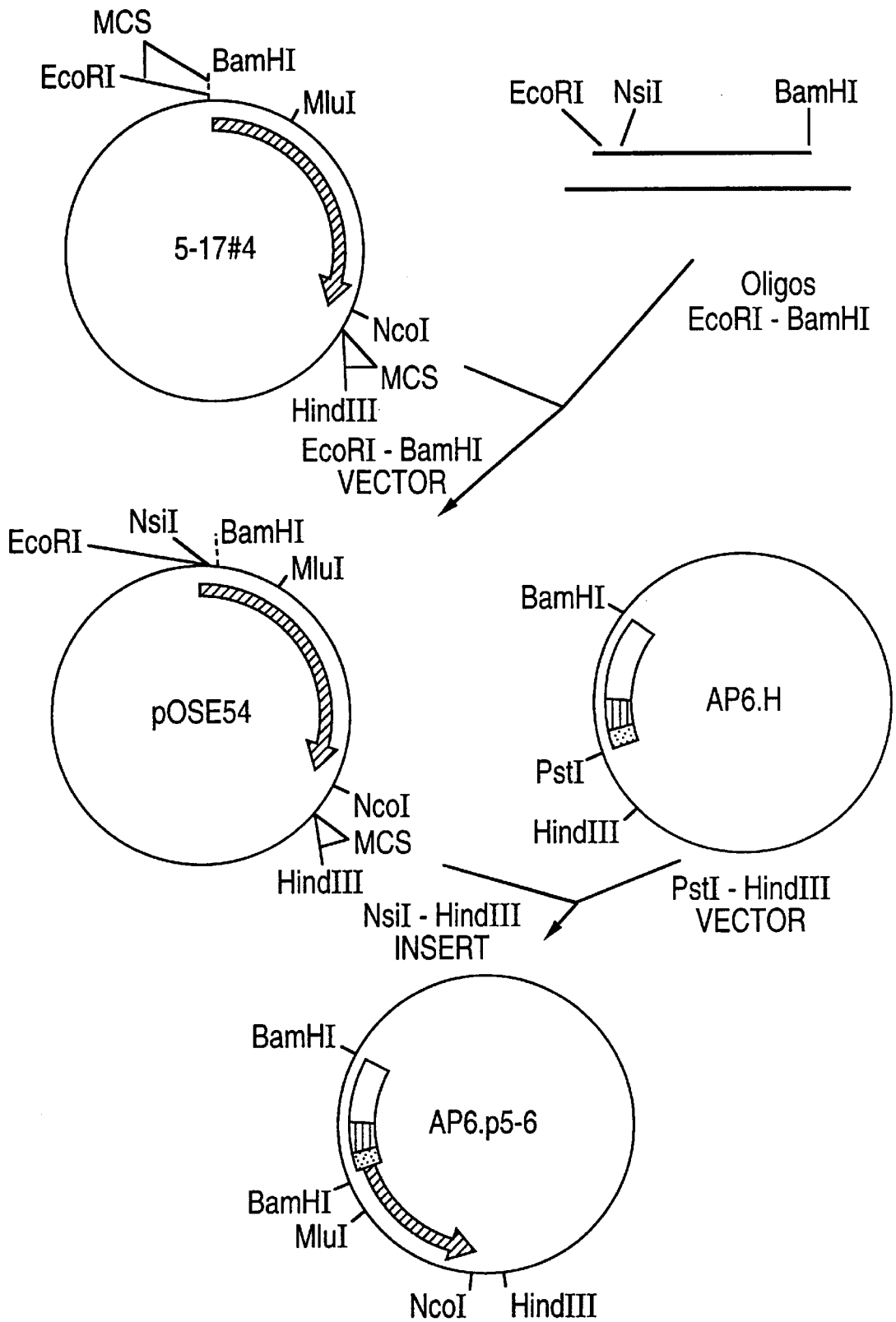
FIG. 33B. The AP6.SlpD vector.

A subclone containing these oligonucleotides was subjected to DNA sequence analysis, a routine procedure employed to confirm the fidelity of the cloned oligonucleotide sequence, and the sequence was found to be correct. An NsiI cloning site contained within the N-terminus of the oligonucleotides allowed for ligation to the Pst I site of AP6.H and subsequent joining of the protease B signal plus leader directly to the SlpD at the serine residue immediately adjacent to the SPase II cysteine. The 1920 NsiI to HindIII fragment encoding SlpD was subsequently cloned into AP6.H to produce AP6.SlpD (See FIG. 33B).

An analogous strategy was used to adapt the N-terminus of the SlpE protein with oligonucleotides encoding the 35 amino acids of SlpE immediately downstream of the SPase II +1 cysteine. A PstI compatible site located at the 5' end allowed for ligation of the oligonucleotides into the PstI site located within the polylinker of a T7T318U based subclone (#5) of SlpE clone p8-2. The oligonucleotides also contained at their 3' end a PflMI site which joins to a natural PflMI site within the SlpE encoding sequence, located 100 nucleotides downstream from the SPase II +1 cysteine. At the 3' end of one of the oligonucleotides creating the PflMI site, there is a potential secondary structure which could potentially have caused difficulties in cloning by forming a relatively stable hairpin, thus providing the PflMI sticky end from participating in the ligation. The sequence of this oligonucleotide and its complement were modified to abolish the hairpin structure, while still encoding the correct amino acid sequence for SlpE.

DNA sequence analysis of two of the three pT7T3.18U subclones containing these oligonucleotides showed that their 5' ends did indeed contain the nucleotide sequences from the oligonucleotides (i.e. they contained an NsiI site), but surprisingly, the sequences at their 3' ends upstream of the PflMI cloning site where the nucleotides should have been substituted to abolish the potential hairpin structure, contained wild type nucleotides. The SlpE encoding sequence remained completely intact and in the correct reading frame, and sequences past the PflMI site were also intact and in the correct frame.

Figure 33C:
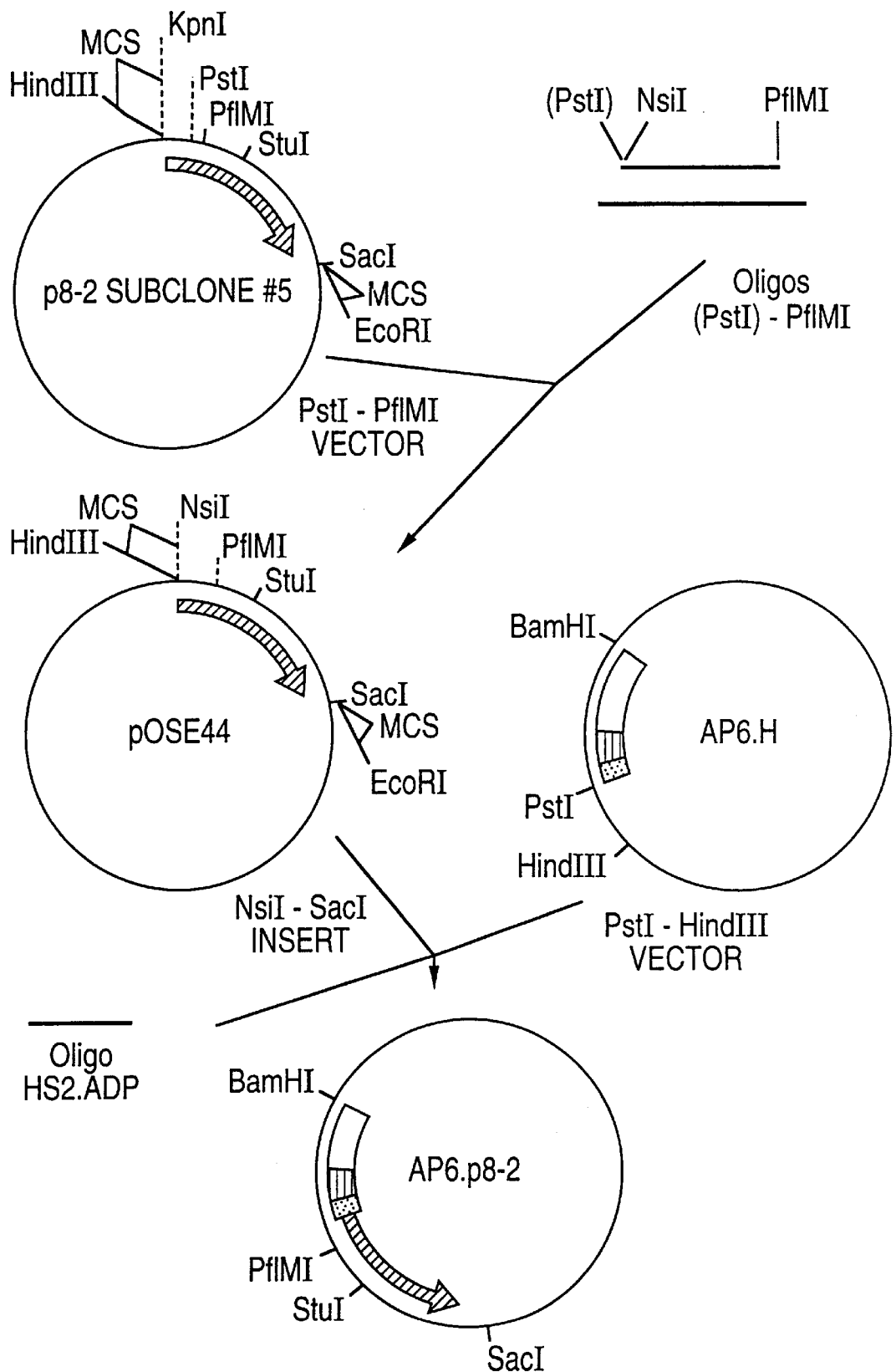
FIG. 33C. The AP6.SlpE vector.

An NsiI cloning site contained within the N-terminus allowed for the subsequent ligation in the correct reading frame into the PstI site of AP6.H and the joining of the protease B signal plus leader directly to the SlpE at the serine residue immediately adjacent to the SPase II +1 cysteine. A SacI site located 238 nucleotides downstream of the SlpE stop codon was used in conjunction with a HindIII—SacI 8mer adapter (AGCTAGCT) to join the 3' end of the SlpE clone to the HindIII site in the AP6.H expression plasmid. The 1820 bp NsiI to SacI fragment encoding SlpE was then used along with the HindIII—SacI adapter in a three way ligation into AP6.H to produce AP6.SlpE (See FIG. 33C).

When these plasmids were used to transform protoplasts of MS11, secreted proteins for both AP6.SlpD and AP6.SlpE were observed at approximate molecular weights of 55 kDa and 56 kDa, respectively. Direct automated N-terminal Edman degradation analysis of the secreted proteins produced the following amino acid sequences(SEQ ID NOS 16 & 17, respectively): SAGGASTXAG for SlpD and APAA-PASGGSSDEDK for SlpE. For SlpD, culture supernatants showed a dramatic increase in the ability to hydrolyse APA-βNA.

TABLE VI

Soluble Protease Substrate Assays

| Transformant | Timepoint | $A_{405}$ | $A_{540}$ |
|---|---|---|---|
| SS12 | 18 | 0.144 | 0.100 |
| | 23 | 0.132 | 0.038 |
| | 41 | 0.126 | 0.018 |
| p5-6 | 17.5 | 1.147 | 0.246 |
| | 23 | 0.990 | 0.278 |
| | 41 | 0.105 | 0.000 |
| p8-2 | 17.5 | 0.115 | 0.084 |
| | 23 | 0.111 | 0.015 |
| | 41 | 0.108 | 0.036 |

The $A_{405}$ values reflect the APA-6NA assay on 20 μl CFB from Tap deleted S. lividans 66 cultures. The $A_{540}$ values reflect the Boc-APARSPA-6NA (SEQ ID NO:15) assay on 20 μl CFB from S. lividans 66 cultures. There is no adjustment for dry weights.

This correlates with the N-terminal sequence data on SlpD which shows that it is lacking the leader peptide (SEQ ID NO:14) APAAPA, which may have been cleaved due to autocatalytic activity of the SlpD itself. In contrast, SlpE culture supernatants showed no ability to hydrolyse APAβNa, correlating with the presence of an intact P6 leader at the N-terminus of the secreted protein.

Example 26

Use of Tap to Improve Secretion of Heterologous Proteins

Heterologous protein secretion in bacterial cells is facilitated by the inclusion of propeptides between the signal peptide (signal sequence) and the amino acid sequence of the actual heterologous protein. These propeptides are useful for stabilizing the secreted protein against hydrolytic activities and enhancing secretion of the protein by providing a homologous signal peptidase processing site. The use of propeptides for the secretion of heterologous proteins in Streptomyces has been described using signals and propeptides from B-galactosidase for interleukin-lB (Lichenstein et al., 1988) and thaumatin (Illingworth et al., 1989); from tendamistat for proinsulin (Koller et al., 1989), interleukin-2 (Bender et al., 1990a) and hirudin (Bender et al., 1990b); and from serine protease inhibitor for domains of immunoglobulin G (Yoshikata et al., 1993) and CD4 (Ueda et al., 1993).

Although the most common mechanism for the secretion of proteins across biological membranes involves the proteolytic removal of an amino terminal signal peptide with a signal peptidase, certain amino acids of protein structures at or near the amino terminus of the mature protein may block or greatly reduce the efficiency of the signal peptidase, leading to lower secretion of the protein. Some proteins are secreted at low levels using the previously described CAN-GENUS™ expression vector APO.H (see Canadian Patent Numbers 1,295,563; 1,295,566; and 1,295,567; and U.S. Pat. No. 5,200,327 and U.S. patent application, Ser. No. 07/397,681). Some of these proteins contain structural constraints located very close to the amino terminus of the mature protein, such as cysteine residues which are involved in a disulfide bond. This may cause steric hindrance to the signal peptidase, thereby preventing cleavage and subsequent release of the mature protein. In such a case, the efficiency of signal peptide removal may be enhanced by insertion at the signal peptidase processing site of amino acids which would provide a more flexible structure between the signal peptide and the amino terminus of the mature protein. The additional amino acids could be removed from the amino terminus of the mature protein. The additional amino acids could be removed from the amino terminus of the secreted protein by an aminopeptidase. The action of the aminopeptidase would be stopped by the amino acid or protein structure at the amino terminus of mature protein. The aminopeptidase may be present in the culture medium into which the protein is being secreted, or may be subsequently added to the secreted protein during the downstream processing.

The present invention describes a process for increasing the level of secreted proteins which have amino terminal structures that interfere with the processing of the signal peptide.

In illustrative embodiments, suitable proteins are interleukin-7 (IL-7), stem cell factor (SCF) and erythropoietin (EPO), which have disulfide bonds involving the amino terminal second, fourth and seventh amino acids, respectively. A signal peptide which is suitable for use for the secretion of IL-7, SCF and EPO is the 37 amino acid signal peptide from the Streptomyces griseus protease B precursor.

The present invention further describes the use of short propeptides, that are multiples of three amino acids in length which, when placed between the signal peptide and the heterologous protein, can increase the level of secreted protein. A peptide leader of either three (APA) or six (SEQ ID NO:14) (APAAPA) amino acids is placed between the protease B signal peptide and the mature protein.

The present invention further describes the secretion of a correctly processed protein secreted from Streptomyces lividans by the successive actions of a signal peptidase to remove the protease B signal peptide, and a tripeptidyl aminopeptidase (Tap) to remove the amino terminal peptide leader. The action of Tap can remove peptides from the propeptide, but not from the heterologous protein, due to an amino-terminal structure, such as a disulfide bond, that prevents further degradation activity.

The present invention further describes the use of Tap for the removal of a propeptide from the amino terminus of a fusion protein comprising a heterologous protein. In a process for the production of a heterologous protein by the secretion of said fusion protein into the growth medium, Tap may be initially present in the growth medium, secreted into the medium during growth, or added after growth to a preparation of said fusion protein.

Two tripeptide leaders that were used were Ala-Pro-Ala (designated AP3) and (Ala-Pro-Ala)-$_2$ (SEQ ID NO:14) which was designated AP6. Oligonucleotides were designed to encode these amino acids and to create a Pst I site which was then used to introduce DNA fragments encoding proteins to be secreted. The pairs of oligonucleotides when annealed formed sticky ends complementary to NsiI and Hind III. The oligonucleotides (SEQ ID NOS 18 & 19, respectively) APA.1 (GCGCCTGCAGCCTA) and APA.2 (AGCTTAGGCTGCAGGCGCTGCA) were used to make the pAP3.H vector by direct ligation to the NsiI-Hind III vector fragment of pAPO.H, containing the aph promoter and encoding the protease B signal peptide. Similarly, APA2.1 (SEQ ID NO:20) (GCGCCGGCGGCGCCTGCAGCCTA) and APΔ2.2 (SEQ ID NO:21) (AGCTTAGGCTGCAGGCGCCGCCGGCGCTGCA) were used to make the pAP6.H vector.

Figure 34:
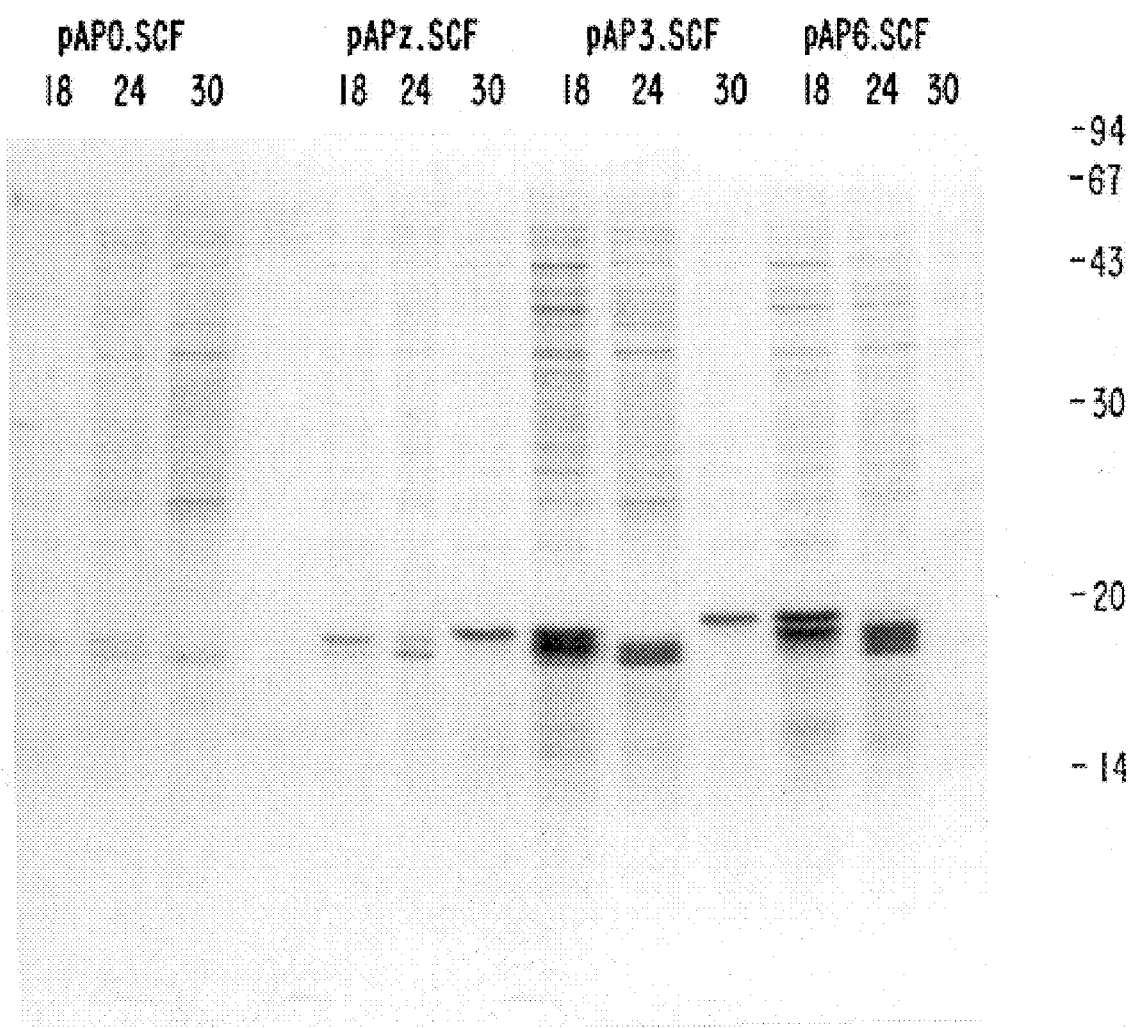
FIG. 34. Protein (SCF) secretion of AP3, AP6, AP6 and APz constructs analyzed by SDS PAGE and visualized by silver staining.

PstI-Hind III DNA fragments encoding SCF, IL7 and EPO were ligated to the PstI-Hind III vector fragments of pAP3.H and pAP6.H respectively. DNA from each of the resulting plasmids was used to transform protoplasts of *S. lividans* 66. Single transformant colonies were grown in 15 ml LB (containing 5 μg/ml thiostrepton) seed medium for 3 days. After homogenization the cultures were inoculated into 1 liter flasks containing 200 ml TSB. Aliquots were removed after 18, 24 and 30 hours of growth at 30° C. The proteins secreted into the culture supernatant fractions (15 μl aliquots) were analyzed by SDS PAGE and visualized by silver staining. The results for the SCF experiments show (FIG. 34) significantly greater protein secretion by the AP3 and AP6 constructs than those of AP0 and APz. The inclusion of the peptide leader increased the secretion of SCF approximately 20 fold, IL-7 approximately 10 fold and EPO approximately 5 fold relative to control vectors lacking the propeptides. Each protein was initially secreted with an amino terminal tripeptide or hexapeptide leader. At a later time in the same culture this initial form of each protein was processed to the mature form with the correct amino terminus by the action of the Tap which was secreted into the medium. The amino terminal structure of each of the proteins prevented the Tap from removing any tripeptides from the amino terminus of each mature protein. This invention is applicable to proteins having an amino terminal structure which would prevent Tap digestion and efficient signal peptidase processing.

The present invention has been described in terms of particular embodiments found or proposed by the present inventors to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

REFERENCES

The references listed below are incorporated herein by reference to the extent that they supplement, explain, provide a background for, or teach methodology, techniques and/or compositions employed herein.

Atlan, D., P. Laloi and R. Portalier. 1989. Isolation and characterization of aminopeptidase-deficient *Lactobacillus bulgaricus* mutants. Appl. Env. Microbiol. 55:1717–1723.

Alvarez, N. G., C. Bordallo, S. Gascon and P. S. Rendueles. 1985. Purification and characterization of a thermosensitive X-prolyl dipeptidyl aminopeptidase from *S. cersvisiae*. BBA 832:119–125.

Aretz, W., K-P. Koller and G. Riess. 1989. Proteolytic enzymes from recombinant *Streptomyces lividans* TK24. FEMS Microbiol. Lett. 65:31–36.

Balon, R-M., Tomkinson, B., Ragnorsson, U. and Zetterqvist, O. 1986. J. Biol. Chem. Purification, Substrate Specificity and Classification of Tripeptidyl Peptidase II. 261 (5) 2409–2417.

Bender, E., K-P. Koller and J. W. Engels. 1990a. Secretory synthesis of human interleukin-2 by *Streptomyces lividans*. Gene 86:227–232.

Bender, E., Vogel, R., Koller, K. P. and J. W. Engels. 1990b. Synthesis and Secretion of Hirudin by *Streptomyces lividans*. Appl. Microbiol. Biotechnol. 34:203–207.

Bibb, M. J., M. J. Bibb, J. M. Ward and S. N. Cohen. 1985. Nucleotide sequences encoding and promoting expression of three antibiotic resistance genes indigenous to *Streptomyces*. Mol. Gen. Genet. 199:26–36.

Bibb, M. J., P. R. Findlay and M. W. Johnson. 1984. The relationship between base composition and codon usage in bacterial genes and its use for the simple and reliable identification of protein-coding sequences. Gene 30:157–166.

Brawner, M., D. Taylor and J. Fornwald. 1990. Expression of the soluble CD-4 receptor in Streptomyces. J. Cell. Biochem., supplement 14A p103.

Butler, M. J., C. C. Davey, P. Krygsman, E. Walczyk, and L. T. Malek. 1992. Cloning of genetic loci involved in endoprotease activity in *S. lividans* 66: a novel neutral protease gene with an adjacent divergent putative regulatory gene. Can. J. Microbiol., in the press.

Davies, B. J. 1964. Ann, N.Y. Acad. Sci. 121, 404

Doggette, P. E., and F. R. Blattner. 1986. Personal access of sequence databases on personal computers. Nucleic Acids Res. 14:611–619.

Fornwald, J. A., Donovan, J. J., Gerber, R., Keller, J., Taylor, D. P., Arcuri, E. J. and Brawner, M. E. 1993. Soluble forms of the human T cell receptor CD4 are efficiently expressed by *Streptomyces lividans*. Bio/Technology 11:1031–1036.

Fukusawa, K. M. and M. Harada. 1981. Purification and properties of dipeptidyl peptidase IV from *Streptococcus mitis* ATCC 9811. Arch. Biochem. Biophys. 210:230–237.

Hanson, H. and M. Frohne. 1976. Crystalline leucine aminopeptidase from lens in proteolytic enzymes (Ed., L. Lorand) Methods Enzymol. 45:504–521.

Henderson, G., P. Krygsman, C. J. Lui, C. C. Davey and L. T. Malek. 1987. Characterization and structure of genes for proteases A and B from *Streptomyces griseus*. J. Bacterial. 169:3778–3784.

Hopwood, D. A., M. J. Bibb, K. F. Chater, T. Kieser, C. J. Bruton, H. M. Kieser, D. J. Lydiate, C. J. Thompson, C. P. Smith, J. M. Ward and H. Schrempf. 1985. Genetic manipulation of Streptomyces, a laboratory manual. The John Innes Foundation, Norwich, U.K.

Illingworth, C., Larson, G. and Hellekant, G. 1989. Secretion of the sweet-tasting plant protein thaumatin by *Streptomyces lividans*. J. of Industrial Microbiology 4:37–42.

Ingram, C., M. Brawner, P. Youngman and J. Westphaling. 1989. xylE functions as an efficient reporter gene in Streptomyces spp.: Use for the study of gal P1, a catabolite-controlled promoter. J. Bacteriol. 177:6617–6624.

Koller, K. P., Riess, G., Sauber, K., Uhlmann, E. and Wallmeier, H. 1989. Recombinant *Streptomyces lividans* secretes a fusion protein of tendamistat and proinsulin. Biotechnology 7:1055–1059.

Kreil, G. 1990. Processing of precursors by dipeptidyl aminopeptidases: a case of molecular ticketing. TIBS. 15:23–26.

Lichenstein, H., Brawner, M. F., Miles, L. M., Meyers, C. A., Young, P. R., Simon, P. L. and Eckhardt, T. 1988. Secretion of interleukin-1β and *Escherichia coli* galactokinase by *Streptomyces lividans*. Gene. 129:129–134.

Lloyd, R. J. and G. G. Pritchard. 1991. Characterization of X-prolyl dipeptidyl aminopeptidase from *Lactococcus lactis* subsp. lactis. J. Gen. Microbiol. 137:49–55.

Malek, L. T., G. Soostmeyer, C. C. Davey, P. Krygsman, J. Compton, J. Gray, T. Zimny and D. Stewart. 1990. Secretion of Granulocyte Macrophase Colony Stimulating Factor (GM-CSF) in *Streptomyces lividans*. J. Cell. Biochem., supplement 14A, p127.

Maniatis, T., E. F. Fritsch and J. Sambrook. 1982. Molecular cloning: a laboratory manual. Cold Spring Harbor Laboratory, Cold Spring Harbor, N.Y.

McDonald J. K., Hoisington, A. R. and Eisenhauer, D. A. 1985. Partial Purification and Characterization of an Ovarian Tripeptidyl Peptidase: A lysosomal exopeptidase that sequentially releases Collagen-related (Gly-Pro-x) Triplets. 126:63–71.

Menn, F-M., Zylstra, G. J. & Gibson, D. T. 1991. Location and sequence of the tool F gene encoding 2-hydroxy-6-oxohepta-2, 4-dienoate hydrolase in Pseudom . . . putide F1. Gene 104:91–94.

Pearson, W. R. and D. J. Lipman. 1988. Improved tools for biological sequence comparison. Proc. Natl. Acad. Sci. USA. 85:2444–2448.

Schoellmann, G. and Shaw, E. 1963. Direct evidence for the presence of histidine in the active center of chymotrypsin. *Biochemistry* 2:252.

Shaw, E., Mares-Guia, M., and Cohen, W. 1975. Evidence for an active center histidine in trypsin through the use of a specific reagent, TLCK, the chloromethyl ketone derived from N-tosyl-lysine. *Biochemistry* 4:2219.

Sloma, A., Rufo, G. A., Jr. and Pero, J. Residual protease III WO, A, 92/16642 (see page enclosed)

Tagakuchi, S., I. Kumagai, J. Nakayama, A. Suzuki and K. Miura. 1989. Efficient extracelluar expression of a foreign protein in Streptomyces using secretory protease inhibitor (SSI) gene fusions. Biotechnology 7:1063–66.

Tinoco, I., Jr., P. N. Borer, B. Dengler, M. D. Levine, O. C. Uhlenbech D. M. Crothers and J. Gralla. 1973. Improved estimation of secondary structure in ribonucleic acid. Nature New Biol. 246:40–41.

Tomkinson, B. and Jonsson, A-K. 1991. Characterization of cDNA for Human Tripeptidyl Peptidase II: The N-Terminal Part of the Enzyme is Similar to Subtilising. Biochemistry 30:168–174.

Ueda, Y, Tsumoto, K., Watanabe, K. and Kumagai, I. 1993. Synthesis and expression of a DNA encoding the Fv domain of an anti-lysozyme monoclonal antibody, HyHEL10, in *Streptomyces lividans. Gene*. 120:129–134.

von Heijne, G. 1989. The structure of signal peptides from bacterial lipoproteins. *Protein Engineering* 2:531–534.

White, Handler, and Smith. 1973.

Wilbur, W. J. and D. J. Lipman. 1983. Rapid Similarity searches of nucleic acid and protein data banks. Proc. Natl. Acad. Sci. USA. 80:726–730.

Yoshimoto, T., N. Murayama, T. Honda, H. Tone, and D. Tsuru. 1988. Cloning and expression of aminopeptidase P gene from *E. coli* HB101 and characterization of expressed enzyme. J. Biochem. 104:93–97.

Yoshimoto, T., H. Tone, T. Honda, K. Osatomi, R. Kobayashi, and D. Tsuru. 1989. Sequencing and high expression of aminopeptidase P gene from *E. coli* HB101. J. Biochem. 105:412–416.

Canadian Patent No. 1,295,563.
Canadian Patent No. 1,295,566.
Canadian Patent No. 1,295,567.
U.S. Pat. No. 5,200,327.
U.S. patent application, Ser. No. 07/397,681.

We claim:

1. A method for the production of a heterologous protein, comprising:
   (a) providing a Streptomyces host cell transformed with a nucleic acid expression construct that comprises a nucleic acid sequence encoding said heterologous protein; and
   (b) incubating said host cell in the presence of a peptide-substituted chloromethylketone aminopeptidase inhibitor, wherein said inhibitor has the structure X-Proline-Y-chloromethylketone, where X denotes an aliphatic or hydroxy amino acid and Y denotes an aliphatic, hydroxy, or sulfur-containing amino acid.

2. A method for the production of a heterologous protein, comprising:
   (a) providing a Streptomyces host cell transformed with a nucleic acid expression construct that comprises a nucleic acid sequence encoding said heterologous protein; and
   (b) incubating said host cell in the presence of a peptide-substituted chloromethyl ketone aminopeptidase inhibitor, wherein said inhibitor has the structure: X-Proline-Y-chloromethylketone, where X and Y denote non-polar amino acids.

3. A method according to claim 1, wherein said inhibitor is selected from the group consisting of alanine-proline-alanine-chloromethylketone, alanine-proline-methionine-chloromethylketone, alanine-proline-serine-chloromethylketone, glycine-proline-leucine-chloromethylketone, serine-proline-alanine-chloromethylketone, and alanine-proline-phenylalanine-chloromethylketone.

4. A method according to claim 1, wherein said inhibitor is alanine-proline-alanine-chloromethylketone.

5. A method according to claim 1, wherein said heterologous protein is selected from the group consisting of granulocyte macrophage-colony stimulating factor (GM-CSF), interleukin-3 (IL-3), interleukin-6 (IL-6), erythropoietin (EPO), stem cell factor (SCF), interleukin-7 (IL-7), and interleukin-2 (IL-2).

6. A method according to claim 1, wherein said heterologous protein is secreted from said host.

7. A method according to claim 1, wherein said host cell has inpaired expression of a tripeptidyl aminopeptidase.

8. A method according to claim 1, wherein said host cell gene encoding a tripeptidyl aminopeptidase is inactivated.

9. A method according to claim 2, wherein said inhibitor is selected from the group consisting of alanine-proline-alanine-chloromethylketone, alanine-proline-methionine-chloromethylketone, alanine-proline-serine-chloromethylketone, glycine-proline-leucine-chloromethylketone, serine-proline-alanine-chloromethylketone, and alanine-proline-phenylalanine-chloromethylketone.

10. A method according to claim 2, wherein said inhibitor is alanine-proline-alanine-chloromethylketone.

11. A method according to claim 2, wherein said heterologous protein is selected from the group consisting of GM-CSF, IL-3, IL-6, EPO, SCF, IL-7, and IL-2.

12. A method according to claim 2, wherein said heterologous protein is secreted from said host cell.

13. A method according to claim 2, wherein said host cell has impaired expression of a tripeptidyl aminopeptidase.

14. A method according to claim 2, wherein a host cell gene encoding a tripeptidyl aminopeptidase is inactivated.

* * * * *

SEQUENCE LISTING (1) GENERAL INFORMATION:

(iii) NUMBER OF SEQUENCES: 25

(2) INFORMATION FOR SEQ ID NO:1:

(i) SEQUENCE CHARACTERISTICS:
      (A) LENGTH: 1908 base pairs
      (B) TYPE: nucleic acid
      (C) STRANDEDNESS: double
      (D) TOPOLOGY: linear (ii) MOLECULE TYPE: cDNA (ix) FEATURE:
      (A) NAME/KEY: CDS
      (B) LOCATION: 146..1756

(ix) FEATURE:
      (A) NAME/KEY: misc_feature
      (B) LOCATION: 146..148
      (D) OTHER INFORMATION: /product= "Met at position -39
         represents fMet"

(ix) FEATURE:
      (A) NAME/KEY: sig_peptide
      (B) LOCATION: 146..262

(ix) FEATURE:
      (A) NAME/KEY: mat_peptide
      (B) LOCATION: 263..1756

(xi) SEQUENCE DESCRIPTION: SEQ ID NO:1:

```
GGCGGGGACC GGCCGACGGC CCCGCCGAAC GAACGCCCTT CTCCGTTTAT CGGATTGGCA        60

AAGAAGTAGC ACTGGCCCTG TTCTCAGGAA ACCCACAGCG GCGAGGATCC CCGTACTTGT       120

CGCGAACACG TACGGGGAGG CCAC ATG AGG AAG AGC AGC ATA CGG CGG AGG          172
              Met Arg Lys Ser Ser Ile Arg Arg Arg
              -39             -35

GCG ACC GCC TTC GGC ACG GCC GGA GCA CTG GTC ACC GCC ACG CTG ATC        220
Ala Thr Ala Phe Gly Thr Ala Gly Ala Leu Val Thr Ala Thr Leu Ile
-30             -25                 -20                 -15

GCC GGC GCC GTC TCG GCA CCC GCC GCG AGC GCC GCC CCG GCC GAC GGC        268
Ala Gly Ala Val Ser Ala Pro Ala Ala Ser Ala Ala Pro Ala Asp Gly
                -10             -5                   1

CAC GGG CAC GGG CGG AGC TGG GAC CGG GAG GCG CGC GGT GCC GCC ATC        316
His Gly His Gly Arg Ser Trp Asp Arg Glu Ala Arg Gly Ala Ala Ile
          5                  10                  15

GCC GCC GCC CGC GCC GCC CGG GCG GGC ATC GAC TGG GAG GAC TGC GCA        364
Ala Ala Ala Arg Ala Ala Arg Ala Gly Ile Asp Trp Glu Asp Cys Ala
         20                  25                  30

GCC GAC TGG AAC CTG CCC AAG CCC ATC CAG TGC GGC TAC GTC ACG GTG        412
Ala Asp Trp Asn Leu Pro Lys Pro Ile Gln Cys Gly Tyr Val Thr Val
 35                  40                  45                  50

CCG ATG GAC TAC GCC AAG CCG TAC GGC AAG CAG ATC AGG CTC GCC GTC        460
Pro Met Asp Tyr Ala Lys Pro Tyr Gly Lys Gln Ile Arg Leu Ala Val
                 55                  60                  65

GAC CGC ATC GGC AAC ACC GGA ACC AGG AGC GAG CGC CAG GGC GCC CTG        508
Asp Arg Ile Gly Asn Thr Gly Thr Arg Ser Glu Arg Gln Gly Ala Leu
             70                  75                  80

ATC TAC AAC CCC GGC GGT CCC GGC GGC TCC GGC CTG CGT TTC CCG GCC        556
Ile Tyr Asn Pro Gly Gly Pro Gly Gly Ser Gly Leu Arg Phe Pro Ala
         85                  90                  95

CGC GTC ACG AAC AAG AGC GCG GTC TGG GCC AAC ACG GCC AAG GCC TAC        604
Arg Val Thr Asn Lys Ser Ala Val Trp Ala Asn Thr Ala Lys Ala Tyr
    100                 105                 110

GAC TTC GTC GGC TTC GAC CCG CGC GGC GTC GGC CAC TCC GCG CCC ATC        652
Asp Phe Val Gly Phe Asp Pro Arg Gly Val Gly His Ser Ala Pro Ile
115                 120                 125                 130

TCC TGC GTC GAC CCG CAG GAG TTC GTC AAG GCA CCC AAG GCC GAC CCC        700
Ser Cys Val Asp Pro Gln Glu Phe Val Lys Ala Pro Lys Ala Asp Pro
                135                 140                 145

GTG CCC GGC TCC GAG GCC GAC AAG CGC GCC CAG CGC AAG CTC GCC CGC        748
Val Pro Gly Ser Glu Ala Asp Lys Arg Ala Gln Arg Lys Leu Ala Arg
            150                 155                 160

GAG TAC GCC GAG GGC TGC TTC GAG CGC AGC GGC GAG ATG CTC CCG CAC        796
Glu Tyr Ala Glu Gly Cys Phe Glu Arg Ser Gly Glu Met Leu Pro His
    165                 170                 175

ATG ACC ACG CCG AAC ACC GCG CGC GAC CTC GAC GTC ATC CGC GCC GCC        844
Met Thr Thr Pro Asn Thr Ala Arg Asp Leu Asp Val Ile Arg Ala Ala
        180                 185                 190

CTC GGC GAG AAG AAG CTC AAC TAC CTC GGC GTC TCC TAC GGC ACC TAC        892
Leu Gly Glu Lys Lys Leu Asn Tyr Leu Gly Val Ser Tyr Gly Thr Tyr
195                 200                 205                 210

CTC GGC GCC GTC TAC GGC ACC CTC TTC CCG GAC CAC GTC CGC CGC ATG        940
Leu Gly Ala Val Tyr Gly Thr Leu Phe Pro Asp His Val Arg Arg Met
                215                 220                 225

GTC GTC GAC AGC GTC GTC AAC CCG TCC CGC GAC AAG ATC TGG TAC CAG        988
Val Val Asp Ser Val Val Asn Pro Ser Arg Asp Lys Ile Trp Tyr Gln
            230                 235                 240

GCC AAC CTG GAC CAG GAC GTC GCC TTC GAG GGC CGC TGG AAG GAC TGG       1036
Ala Asn Leu Asp Gln Asp Val Ala Phe Glu Gly Arg Trp Lys Asp Trp
```

```
Ala Asn Leu Asp Gln Asp Val Ala Phe Glu Gly Arg Trp Lys Asp Trp
            245                 250                 255

CAG GAC TGG GTC GCC GCG AAC GAC GCC GCC TAC CAC CTC GGC GAC ACC    1084
Gln Asp Trp Val Ala Ala Asn Asp Ala Ala Tyr His Leu Gly Asp Thr
260                 265                 270

CGC GCC GAG GTC CAG GAC CAG TGG CTG AAG CTG CGC GCC GCC GCC GCG    1132
Arg Ala Glu Val Gln Asp Gln Trp Leu Lys Leu Arg Ala Ala Ala Ala
275                 280                 285                 290

AAG AAG CCG CTG GGC GGC GTC GTC GGA CCG GCC GAG CTG ATC TCC TTC    1180
Lys Lys Pro Leu Gly Gly Val Val Gly Pro Ala Glu Leu Ile Ser Phe
                295                 300                 305

TTC CAG AGC GCC CCG TAC TAC GAC TCC GCC TGG GCG CCG ACC GCG GAG    1228
Phe Gln Ser Ala Pro Tyr Tyr Asp Ser Ala Trp Ala Pro Thr Ala Glu
            310                 315                 320

ATC TTC AGC AAG TAC GTC GCC GGC GAC ACC CAG GCG CTC GTC GAC GCC    1276
Ile Phe Ser Lys Tyr Val Ala Gly Asp Thr Gln Ala Leu Val Asp Ala
            325                 330                 335

GCC GCA CCC GAC CTG TCC GAC ACC GCG GGC AAC GCC TCC GCG GAG AAC    1324
Ala Ala Pro Asp Leu Ser Asp Thr Ala Gly Asn Ala Ser Ala Glu Asn
340                 345                 350

GGC AAC GCC GTC TAC ACG GCC GTC GAG TGC ACC GAC GCC AAG TGG CCC    1372
Gly Asn Ala Val Tyr Thr Ala Val Glu Cys Thr Asp Ala Lys Trp Pro
355                 360                 365                 370

GCC AAC TGG CGC ACC TGG GAC CGG GAC AAC ACC CGG CTC CAC CGC GAC    1420
Ala Asn Trp Arg Thr Trp Asp Arg Asp Asn Thr Arg Leu His Arg Asp
                375                 380                 385

CAC CCG TTC ATG ACC TGG GCC AAC GCC TGG ATG AAC CTG CCC TGT GCC    1468
His Pro Phe Met Thr Trp Ala Asn Ala Trp Met Asn Leu Pro Cys Ala
            390                 395                 400

ACC TGG CCG GTC AAG CAG CAG ACC CCG CTG AAC GTG AAG ACC GGC AAG    1516
Thr Trp Pro Val Lys Gln Gln Thr Pro Leu Asn Val Lys Thr Gly Lys
            405                 410                 415

GGA CTT CCG CCG GTG CTG ATC GTC CAG TCC GAG CGT GAC GCC GCC ACC    1564
Gly Leu Pro Pro Val Leu Ile Val Gln Ser Glu Arg Asp Ala Ala Thr
420                 425                 430

CCG TAC GAG GGC GCC GTC GAA CTG CAC CAG CGG TTC CGG GGA TCC CGC    1612
Pro Tyr Glu Gly Ala Val Glu Leu His Gln Arg Phe Arg Gly Ser Arg
435                 440                 445                 450

CTG ATC ACC GAG CGG GAC GCC GGC TCC CAC GGC GTC ACC GGC CTG GTC    1660
Leu Ile Thr Glu Arg Asp Ala Gly Ser His Gly Val Thr Gly Leu Val
                455                 460                 465

AAC CCG TGC ATC AAC GAC CGG GTC GAC ACC TAC CTG CTC ACC GGC AGG    1708
Asn Pro Cys Ile Asn Asp Arg Val Asp Thr Tyr Leu Leu Thr Gly Arg
            470                 475                 480

ACG GAC GCC CGC GAC GTG ACC TGC GCG CCG CAC GCC ACG CCC AGG CCG    1756
Thr Asp Ala Arg Asp Val Thr Cys Ala Pro His Ala Thr Pro Arg Pro
            485                 490                 495

TAACCCGGGC TCAGGCCAAG CGGGGGGAGG GGGCGACCGG TCCGACCGGC CGCCCCCTCC    1816

CCCCACCTGT CGCTACCGTC CCTCGGCCCA GGCGTCCTCC GCCGCGTAGT CGAAGAGGTC    1876

GCCGTACGCC TTGAACATCT TCGGGTAGGC CT                                 1908

(2) INFORMATION FOR SEQ ID NO:2:

(i) SEQUENCE CHARACTERISTICS:
        (A) LENGTH: 537 amino acids
        (B) TYPE: amino acid
        (D) TOPOLOGY: linear (ii) MOLECULE TYPE: protein
```

(xi) SEQUENCE DESCRIPTION: SEQ ID NO:2:

```
Met Arg Lys Ser Ser Ile Arg Arg Ala Thr Ala Phe Gly Thr Ala
-39             -35             -30             -25

Gly Ala Leu Val Thr Ala Thr Leu Ile Ala Gly Ala Val Ser Ala Pro
            -20             -15             -10

Ala Ala Ser Ala Ala Pro Ala Asp Gly His Gly His Gly Arg Ser Trp
        -5              1               5

Asp Arg Glu Ala Arg Gly Ala Ile Ala Ala Arg Ala Ala Arg
10              15              20              25

Ala Gly Ile Asp Trp Glu Asp Cys Ala Ala Asp Trp Asn Leu Pro Lys
                30              35              40

Pro Ile Gln Cys Gly Tyr Val Thr Pro Met Asp Tyr Ala Lys Pro
            45              50              55

Tyr Gly Lys Gln Ile Arg Leu Ala Val Asp Arg Ile Gly Asn Thr Gly
        60              65              70

Thr Arg Ser Glu Arg Gln Gly Ala Leu Ile Tyr Asn Pro Gly Gly Pro
75              80              85

Gly Gly Ser Gly Leu Arg Phe Pro Ala Arg Val Thr Asn Lys Ser Ala
90              95              100             105

Val Trp Ala Asn Thr Ala Lys Ala Tyr Asp Phe Val Gly Phe Asp Pro
            110             115             120

Arg Gly Val Gly His Ser Ala Pro Ile Ser Cys Val Asp Pro Gln Glu
            125             130             135

Phe Val Lys Ala Pro Lys Ala Asp Pro Val Pro Gly Ser Glu Ala Asp
        140             145             150

Lys Arg Ala Gln Arg Lys Leu Ala Arg Glu Tyr Ala Glu Gly Cys Phe
155             160             165

Glu Arg Ser Gly Glu Met Leu Pro His Met Thr Thr Pro Asn Thr Ala
170             175             180             185

Arg Asp Leu Asp Val Ile Arg Ala Ala Leu Gly Glu Lys Lys Leu Asn
            190             195             200

Tyr Leu Gly Val Ser Tyr Gly Thr Tyr Leu Gly Ala Val Tyr Gly Thr
            205             210             215

Leu Phe Pro Asp His Val Arg Arg Met Val Val Asp Ser Val Val Asn
        220             225             230

Pro Ser Arg Asp Lys Ile Trp Tyr Gln Ala Asn Leu Asp Gln Asp Val
235             240             245

Ala Phe Glu Gly Arg Trp Lys Asp Trp Gln Asp Trp Val Ala Ala Asn
250             255             260             265

Asp Ala Ala Tyr His Leu Gly Asp Thr Arg Ala Glu Val Gln Asp Gln
            270             275             280

Trp Leu Lys Leu Arg Ala Ala Ala Lys Lys Pro Leu Gly Gly Val
            285             290             295

Val Gly Pro Ala Glu Leu Ile Ser Phe Gln Ser Ala Pro Tyr Tyr
        300             305             310

Asp Ser Ala Trp Ala Pro Thr Ala Glu Ile Phe Ser Lys Tyr Val Ala
        315             320             325

Gly Asp Thr Gln Ala Leu Val Asp Ala Ala Pro Asp Leu Ser Asp
330             335             340             345

Thr Ala Gly Asn Ala Ser Ala Glu Asn Gly Asn Ala Val Tyr Thr Ala
            350             355             360
```

```
Val Glu Cys Thr Asp Ala Lys Trp Pro Ala Asn Trp Arg Thr Trp Asp
            365                 370                 375

Arg Asp Asn Thr Arg Leu His Arg Asp His Pro Phe Met Thr Trp Ala
            380                 385                 390

Asn Ala Trp Met Asn Leu Pro Cys Ala Thr Trp Pro Val Lys Gln Gln
    395                 400                 405

Thr Pro Leu Asn Val Lys Thr Gly Lys Gly Leu Pro Pro Val Leu Ile
410                 415                 420                 425

Val Gln Ser Glu Arg Asp Ala Ala Thr Pro Tyr Glu Gly Ala Val Glu
            430                 435                 440

Leu His Gln Arg Phe Arg Gly Ser Arg Leu Ile Thr Glu Arg Asp Ala
            445                 450                 455

Gly Ser His Gly Val Thr Gly Leu Val Asn Pro Cys Ile Asn Asp Arg
            460                 465                 470

Val Asp Thr Tyr Leu Leu Thr Gly Arg Thr Asp Ala Arg Asp Val Thr
    475                 480                 485

Cys Ala Pro His Ala Thr Pro Arg Pro
490                 495
```

(2) INFORMATION FOR SEQ ID NO:3:

(i) SEQUENCE CHARACTERISTICS:
        (A) LENGTH: 2185 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 531..2066

(ix) FEATURE:
        (A) NAME/KEY: sig_peptide
        (B) LOCATION: 531..902

(ix) FEATURE:
        (A) NAME/KEY: mat_peptide
        (B) LOCATION: 903..2066

(ix) FEATURE:
        (A) NAME/KEY: misc_feature
        (B) LOCATION: 531..533
        (D) OTHER INFORMATION: /product= "Met at position -124
            represents fMet"

(xi) SEQUENCE DESCRIPTION: SEQ ID NO:3:

```
GGTACCAGGC GACGAAGGCG ACGGTCAGCG GGAACGCGAA GGAACGGAAG GAGCGGCGCA      60

GTTCGGCGAA CTCGGCGCTC TGCTGCACTT CGGAGAACTC CTCGGCGGAG GGGAGGCGGT     120

GCTCCTCTTG CGAGGGGGGC TCCTCTTTGG AGGGGGGCGG TGCGTCGGGT GGCCACGGAG     180

TCTCCTCGTA CGACGGACAT GACGGCTTGG ACCTCGGTGT CTCGCAGGG GGCTGATCGT     240

GCTCGGGCTC CCTGTCCAAC GACACGGCGC CCCGCGGGGC CCGGTTCAAC ACCCGTGGCA     300

CTTTCCGAAG TCGTCCTCGG CGGGTCATTG CTGGCCAGGG ACTTCGGGGG ATAGCTTCAC     360

CCTGCACCAC TACGTCATGT ACCTGCCCGG CCCGTTTCAC CCGTGCCCGG GCAGGTGCTG     420

TTTGCCGGAT GATGTGGAGA CCCCATGGAT CATCTGCGCT TCCCGCGCGA CCCGCGCTCC     480

AGACGCGGGC TCGTTTCCCG AGCTTTCCCG ACGGACTGGA GACATCACGC ATG ACC        536
                                                       Met Thr
                                                       -124
```

```
GCT CCC CTC TCG CGT CAC CGC CGT GCC CTC GCG ATT CCG GCG GGC CTG        584
Ala Pro Leu Ser Arg His Arg Arg Ala Leu Ala Ile Pro Ala Gly Leu
        -120            -115            -110

GCC GTG GCC GCG TCG CTC GCG TTC CTG CCG GGC ACC CCG GCC GCC GCG        632
Ala Val Ala Ala Ser Leu Ala Phe Leu Pro Gly Thr Pro Ala Ala Ala
        -105            -100            -95

ACC CCC GCG GCC GAG GCC GCG CCC TCG ACG GCG GCG GAC GCG ACC TCG        680
Thr Pro Ala Ala Glu Ala Ala Pro Ser Thr Ala Ala Asp Ala Thr Ser
-90             -85             -80             -75

CTC AGC TAC GTC GTC AAC GTC GCC TCC GGG CAC CGT CCT TCG GCC ACC        728
Leu Ser Tyr Val Val Asn Val Ala Ser Gly His Arg Pro Ser Ala Thr
            -70             -65             -60

GTG CGG CGG GCG ATA GCC AAG GCG GGC GGC ACG ATC GTC ACG TCG TAC        776
Val Arg Arg Ala Ile Ala Lys Ala Gly Gly Thr Ile Val Thr Ser Tyr
        -55             -50             -45

GAC CGG ATC GGC GTG ATC GTC GTC CAC TCC GCC AAC CCC GAC TTC GCC        824
Asp Arg Ile Gly Val Ile Val Val His Ser Ala Asn Pro Asp Phe Ala
        -40             -35             -30

AAG ACC GTG CGC AAG GTG CGC GGC GTG CAG TCG GCC GGT GCC ACC CGC        872
Lys Thr Val Arg Lys Val Arg Gly Val Gln Ser Ala Gly Ala Thr Arg
        -25             -20             -15

ACC GCG CCA CTG CCC TCG GCC GCC ACC ACC GAC ACG GGC GCG CCG CAG        920
Thr Ala Pro Leu Pro Ser Ala Ala Thr Thr Asp Thr Gly Ala Pro Gln
-10             -5              1               5

GTG CTC GGC GGC GAG GAC CTG GCC GCC GCC AAG GCC GCC TCC GCG AAG        968
Val Leu Gly Gly Glu Asp Leu Ala Ala Ala Lys Ala Ala Ser Ala Lys
            10              15              20

GCC GAG GGC CAG GAC CCG CTG GAG TCG CTC CAG TGG GAC CTG CCC GCC       1016
Ala Glu Gly Gln Asp Pro Leu Glu Ser Leu Gln Trp Asp Leu Pro Ala
        25              30              35

ATC AAG GCG GAC AAG GCG CAC GAG AAG TCG CTG GGC AGC AGG AAG GTG       1064
Ile Lys Ala Asp Lys Ala His Glu Lys Ser Leu Gly Ser Arg Lys Val
        40              45              50

ACC GTC GCC GTC ATC GAC ACC GGC GTC GAC GAC ACC CAC CCG GAC ATC       1112
Thr Val Ala Val Ile Asp Thr Gly Val Asp Asp Thr His Pro Asp Ile
55              60              65              70

GCC CCG AAC TTC GAC CGG CAG GCG TCC GTC AAC TGT GTG GCG GGC AAG       1160
Ala Pro Asn Phe Asp Arg Gln Ala Ser Val Asn Cys Val Ala Gly Lys
            75              80              85

CG GAC ACC GCC GAC GGG GCC TGG CGG CCG AGC GCG GCG GAG AGC CCG        1208
Pro Asp Thr Ala Asp Gly Ala Trp Arg Pro Ser Ala Ala Glu Ser Pro
            90              95              100

CAC GGC ACC CAC GTG GCC GGG GAG ATA GCC GCC GCC AAG AAC GGC GTC       1256
His Gly Thr His Val Ala Gly Glu Ile Ala Ala Ala Lys Asn Gly Val
        105             110             115

GGC ATG ACC GGC GTG GCA CCC GGG GTG AAG GTG GCC GGC ATC AAG GTC       1304
Gly Met Thr Gly Val Ala Pro Gly Val Lys Val Ala Gly Ile Lys Val
120             125             130

TCC AAC CCC GAC GGC TTC TTC TAC ACC GAG GCC GTG GTC TGC GGC TTC       1352
Ser Asn Pro Asp Gly Phe Phe Tyr Thr Glu Ala Val Val Cys Gly Phe
135             140             145             150

ATG TGG GCG GCC GAG CAC GGC GTC GAC GTG ACC AAC AAC AGC TAT TAC       1400
Met Trp Ala Ala Glu His Gly Val Asp Val Thr Asn Asn Ser Tyr Tyr
            155             160             165

ACC GAC CCG TGG TAC TTC AAC TGC AAG GAC GAC CCC GAC CAG AAG GCG       1448
Thr Asp Pro Trp Tyr Phe Asn Cys Lys Asp Asp Pro Asp Gln Lys Ala
            170             175             180

CTC GTC GAG GCC GTC TCG CGG GCC TCC CGG TAC GCG GAG AAG AAG GGC       1496
```

-continued

```
Leu Val Glu Ala Val Ser Arg Ala Ser Arg Tyr Ala Glu Lys Lys Gly
            185                 190                 195

GCG GTC AAC GTC GCC GCG GCC GGC AAC GAG AAC TAC GAC CTC ACC TCC    1544
Ala Val Asn Val Ala Ala Ala Gly Asn Glu Asn Tyr Asp Leu Thr Ser
200                 205                 210

GAC GAG ATC ACC GAC CCG TCC TCG CCC AAC GAC ACC ACG CCC GGC GAC    1592
Asp Glu Ile Thr Asp Pro Ser Ser Pro Asn Asp Thr Thr Pro Gly Asp
215                 220                 225                 230

CGG ACC GTC GAC CCG TCG AAG TGC CTG GAC ATC CCG ACC CAG CTG CCG    1640
Arg Thr Val Asp Pro Ser Lys Cys Leu Asp Ile Pro Thr Gln Leu Pro
                235                 240                 245

GGT GTC GTG ACG GTC GCG GCG ACC GGT GCG AAG GGC CTC AAG TCG TCC    1688
Gly Val Val Thr Val Ala Ala Thr Gly Ala Lys Gly Leu Lys Ser Ser
            250                 255                 260

TTC TCC AAC CAC GGG CTG GGC GTC ATC GAC ATC GCC GCG CCC GGC GGC    1736
Phe Ser Asn His Gly Leu Gly Val Ile Asp Ile Ala Ala Pro Gly Gly
            265                 270                 275

GAC TCG ACG GCC TAC CAG ACC CCG GAG CCG CCC GCC ACG AGC GGC CTG    1784
Asp Ser Thr Ala Tyr Gln Thr Pro Glu Pro Pro Ala Thr Ser Gly Leu
280                 285                 290

ATC CTG GGC ACG CTG CCC GGC GGC AAG TGG GGC TAC ATG GCC GGT ACG    1832
Ile Leu Gly Thr Leu Pro Gly Gly Lys Trp Gly Tyr Met Ala Gly Thr
295                 300                 305                 310

TCC ATG GCC TCC CCG CAC GTC GCG GGC GTC GCC GCC CTC ATC AAG TCG    1880
Ser Met Ala Ser Pro His Val Ala Gly Val Ala Ala Leu Ile Lys Ser
                315                 320                 325

ACG CAC CCG CAC GCC TCC CCC GCC ATG GTG AAG GCG CTG CTG TAC GCC    1928
Thr His Pro His Ala Ser Pro Ala Met Val Lys Ala Leu Leu Tyr Ala
            330                 335                 340

GAG GCC GAC GCC ACG GCG TGC ACC AAG CCG TAC GAC ATC GAC GGC GAC    1976
Glu Ala Asp Ala Thr Ala Cys Thr Lys Pro Tyr Asp Ile Asp Gly Asp
            345                 350                 355

GGC AAG GTC GAC GCG GTG TGC GAG GGC CCG AAG AAC CGC AAC GGC TTC    2024
Gly Lys Val Asp Ala Val Cys Glu Gly Pro Lys Asn Arg Asn Gly Phe
360                 365                 370

TAC GGC TGG GGC ATG GCC GAC GCG CTG GAC GCG GTG ACC TGG            2066
Tyr Gly Trp Gly Met Ala Asp Ala Leu Asp Ala Val Thr Trp
375                 380                 385

TAGCCGGTAC GCGTACCCGT GCGTGAGGCG GGGGCGGCGG TCCGGTTCCC GTCCGGTCCG   2126

CCGCCCCCGT CGTCGTCGTC GTACGACAGT ATCTTCGCCA TGGACACTTA CGAGGATCC    2185
```

(2) INFORMATION FOR SEQ ID NO:4:

(i) SEQUENCE CHARACTERISTICS:
        (A) LENGTH: 512 amino acids
        (B) TYPE: amino acid
        (D) TOPOLOGY: linear (ii) MOLECULE TYPE: protein (xi) SEQUENCE DESCRIPTION: SEQ ID NO:4:

```
Met Thr Ala Pro Leu Ser Arg His Arg Arg Ala Leu Ala Ile Pro Ala
-124                -120                -115                -110

Gly Leu Ala Val Ala Ala Ser Leu Ala Phe Leu Pro Gly Thr Pro Ala
            -105                -100                -95

Ala Ala Thr Pro Ala Ala Glu Ala Ala Pro Ser Thr Ala Ala Asp Ala
            -90                 -85                 -80

Thr Ser Leu Ser Tyr Val Val Asn Val Ala Ser Gly His Arg Pro Ser
            -75                 -70                 -65
```

```
Ala Thr Val Arg Arg Ala Ile Ala Lys Ala Gly Gly Thr Ile Val Thr
-60                 -55                 -50                 -45

Ser Tyr Asp Arg Ile Gly Val Ile Val His Ser Ala Asn Pro Asp
                -40                 -35                 -30

Phe Ala Lys Thr Val Arg Lys Val Arg Gly Val Gln Ser Ala Gly Ala
                -25                 -20                 -15

Thr Arg Thr Ala Pro Leu Pro Ser Ala Ala Thr Thr Asp Thr Gly Ala
        -10                  -5                   1

Pro Gln Val Leu Gly Gly Glu Asp Leu Ala Ala Lys Ala Ala Ser
 5               10                  15                  20

Ala Lys Ala Glu Gly Gln Asp Pro Leu Glu Ser Leu Gln Trp Asp Leu
                25                  30                  35

Pro Ala Ile Lys Ala Asp Lys Ala His Glu Lys Ser Leu Gly Ser Arg
            40                  45                  50

Lys Val Thr Val Ala Val Ile Asp Thr Gly Val Asp Asp Thr His Pro
            55                  60                  65

Asp Ile Ala Pro Asn Phe Asp Arg Gln Ala Ser Val Asn Cys Val Ala
 70                  75                  80

Gly Lys Pro Asp Thr Ala Asp Gly Ala Trp Arg Pro Ser Ala Ala Glu
 85                  90                  95                  100

Ser Pro His Gly Thr His Val Ala Gly Glu Ile Ala Ala Ala Lys Asn
                105                 110                 115

Gly Val Gly Met Thr Gly Val Ala Pro Gly Val Lys Val Ala Gly Ile
                120                 125                 130

Lys Val Ser Asn Pro Asp Gly Phe Phe Tyr Thr Glu Ala Val Val Cys
            135                 140                 145

Gly Phe Met Trp Ala Ala Glu His Gly Val Asp Val Thr Asn Asn Ser
150                 155                 160

Tyr Tyr Thr Asp Pro Trp Tyr Phe Asn Cys Lys Asp Asp Pro Asp Gln
165                 170                 175                 180

Lys Ala Leu Val Glu Ala Val Ser Arg Ala Ser Arg Tyr Ala Glu Lys
                185                 190                 195

Lys Gly Ala Val Asn Val Ala Ala Gly Asn Glu Asn Tyr Asp Leu
                200                 205                 210

Thr Ser Asp Glu Ile Thr Asp Pro Ser Ser Pro Asn Thr Thr Pro
    215                 220                 225

Gly Asp Arg Thr Val Asp Pro Ser Lys Cys Leu Asp Ile Pro Thr Gln
230                 235                 240

Leu Pro Gly Val Val Thr Val Ala Ala Thr Gly Ala Lys Gly Leu Lys
245                 250                 255                 260

Ser Ser Phe Ser Asn His Gly Leu Gly Val Ile Asp Ile Ala Ala Pro
                265                 270                 275

Gly Gly Asp Ser Thr Ala Tyr Gln Thr Pro Glu Pro Ala Thr Ser
            280                 285                 290

Gly Leu Ile Leu Gly Thr Leu Pro Gly Gly Lys Trp Gly Tyr Met Ala
                295                 300                 305

Gly Thr Ser Met Ala Ser Pro His Val Ala Gly Val Ala Ala Leu Ile
            310                 315                 320

Lys Ser Thr His Pro His Ala Ser Pro Ala Met Val Lys Ala Leu Leu
325                 330                 335                 340

Tyr Ala Glu Ala Asp Ala Thr Ala Cys Thr Lys Pro Tyr Asp Ile Asp
                345                 350                 355

Gly Asp Gly Lys Val Asp Ala Val Cys Glu Gly Pro Lys Asn Arg Asn
```

```
                  360                 365                 370
Gly Phe Tyr Gly Trp Gly Met Ala Asp Ala Leu Asp Ala Val Thr Trp
                375                 380                 385

(2) INFORMATION FOR SEQ ID NO:5:

(i) SEQUENCE CHARACTERISTICS:
        (A) LENGTH: 1777 base pairs
        (B) TYPE: nucleic acid
        (C) STRANDEDNESS: double
        (D) TOPOLOGY: linear (ii) MOLECULE TYPE: cDNA (ix) FEATURE:
         (A) NAME/KEY: CDS
         (B) LOCATION: 190..1728

(ix) FEATURE:
         (A) NAME/KEY: misc_feature
         (B) LOCATION: 190..192
         (D) OTHER INFORMATION: /product= "Met at position 1
             represents fMet"

(xi) SEQUENCE DESCRIPTION: SEQ ID NO:5:

GGTACCGGCG GCCAAGACCG TGTGCTCCTG ACCGCGGACG CCACCACAGG TCGGCAGAAG        60

CAGCAGATCG ACAGAAGTAG CAGGTCAGAG CGTTATCCAC AGGCGTCGGC GGGTGCTGCC       120

CCCGCCACCT ACCATGGCAG GAACGCCATC CGCCGCACGG CGCGGACGGC TTGCCAGGGG       180

GGAGAGGAC ATG GCG CGT CTC GTC CGG TGG ACG GCT CTG ACG GCC GCC          228
          Met Ala Arg Leu Val Arg Trp Thr Ala Leu Thr Ala Ala
           1               5                  10

GCC GCA CTG CTG ACG GCG GGC TGC AGC GGC GGC TCG TCC GAC GAG GAC        276
Ala Ala Leu Leu Thr Ala Gly Cys Ser Gly Gly Ser Ser Asp Glu Asp
         15                  20                  25

AAG GAC GAC GGG GGC AGG AGC AGC GCG GGA CCT TCG GCG GCG GCA CCC        324
Lys Asp Asp Gly Gly Arg Ser Ser Ala Gly Pro Ser Ala Ala Ala Pro
 30                  35                  40                  45

TCC GGG GTG CCG GAG GCA CTG GCG TCC CAG ACG CTG GAC TGG GCC CGA        372
Ser Gly Val Pro Glu Ala Leu Ala Ser Gln Thr Leu Asp Trp Ala Arg
                 50                  55                  60

TGC GAG GGC AGC GAC GAT GCC CCG GCG CCG GAC GGC GAC TGG CGG TGC        420
Cys Glu Gly Ser Asp Asp Ala Pro Ala Pro Asp Gly Asp Trp Arg Cys
             65                  70                  75

GCC ACG CTG AAG GCA CCG CTG GAC TGG TCC GAC CCC GAC GGC GAG ACG        468
Ala Thr Leu Lys Ala Pro Leu Asp Trp Ser Asp Pro Asp Gly Glu Thr
         80                  85                  90

ATC GAT CTC GCG CTG ATC CGG TCC CGG GCG AGC GGG GAC GAC CGC ATC        516
Ile Asp Leu Ala Leu Ile Arg Ser Arg Ala Ser Gly Asp Asp Arg Ile
     95                 100                 105

GGC TCC CTG CTG TTC AAC TTC GGC GGC CCG GGC GCC TCC GGC GTC TCC        564
Gly Ser Leu Leu Phe Asn Phe Gly Gly Pro Gly Ala Ser Gly Val Ser
110                 115                 120                 125

ACG ATG CCG TCC TAC GCC GAC ACC GTC TCC TCC CTG CAC GAG CGG TAC        612
Thr Met Pro Ser Tyr Ala Asp Thr Val Ser Ser Leu His Glu Arg Tyr
                130                 135                 140

GAC CTG GTG AGC TGG GAC CCG CGC GGG GTG GCC GCC AGC GAG GGC GTC        660
Asp Leu Val Ser Trp Asp Pro Arg Gly Val Ala Ala Ser Glu Gly Val
            145                 150                 155

CGC TGC CGC ACC GAC GAG GCG ATC GAG GCC GCC GAG TCG GTG GAC TCC        708
```

```
            Arg Cys Arg Thr Asp Glu Ala Ile Glu Ala Ala Glu Ser Val Asp Ser
                160                 165                 170

ACG CCG GAC TCC CCG GCC GAG GAG CAG GCC TAC CTG AAG GAC GCC GCC            756
Thr Pro Asp Ser Pro Ala Glu Glu Gln Ala Tyr Leu Lys Asp Ala Ala
    175                 180                 185

GAC TTC GGC AGG GGC TGC GAG AAG GCC GCC GGC AAG CTC ATG GAA CAC            804
Asp Phe Gly Arg Gly Cys Glu Lys Ala Ala Gly Lys Leu Met Glu His
190                 195                 200                 205

GTC TCG ACC ACG GAC ACG GCC CGC GAC ATG GAC CTG ATG CGG CAC GTC            852
Val Ser Thr Thr Asp Thr Ala Arg Asp Met Asp Leu Met Arg His Val
                210                 215                 220

CTG GGC GAC GAG AGG ATG CAC TAC TTC GGC ATC TCC TAC GGC ACC GAA            900
Leu Gly Asp Glu Arg Met His Tyr Phe Gly Ile Ser Tyr Gly Thr Glu
            225                 230                 235

CTC GGC GGC GTC TAC GCC CAT CTG TTC CCC GAG CAC GTG GGC CGC GTG            948
Leu Gly Gly Val Tyr Ala His Leu Phe Pro Glu His Val Gly Arg Val
        240                 245                 250

ATC CTC GAC GCG GTG GTG GAC CCG GGC GCC GAC ACG ATG GGC CAC GCC            996
Ile Leu Asp Ala Val Val Asp Pro Gly Ala Asp Thr Met Gly His Ala
    255                 260                 265

GAG AAC CAG GCC AGG GGT TTC CAG CGC GCG CTG GAC GAC TAC CTG GAG           1044
Glu Asn Gln Ala Arg Gly Phe Gln Arg Ala Leu Asp Asp Tyr Leu Glu
270                 275                 280                 285

TCG ACC GGC CAG GAA CCC GAA CAG GGG TCG CGG AAG ATC GCC GGC CTG           1092
Ser Thr Gly Gln Glu Pro Glu Gln Gly Ser Arg Lys Ile Ala Gly Leu
                290                 295                 300

CTG GAG CGG CTG GAC GCC GAG CCA CTG CCC ACG TCC TCG CCG GGG CGG           1140
Leu Glu Arg Leu Asp Ala Glu Pro Leu Pro Thr Ser Ser Pro Gly Arg
            305                 310                 315

GAG CTG ACG CAG ACC CTC GCG TTC ACC GGC ATC GTG CTG CCG CTG TAC           1188
Glu Leu Thr Gln Thr Leu Ala Phe Thr Gly Ile Val Leu Pro Leu Tyr
        320                 325                 330

AGC GAG AGC GGC TGG CCG GCC CTG ACC AGT GCG CTG AAG GCG GCC GAG           1236
Ser Glu Ser Gly Trp Pro Ala Leu Thr Ser Ala Leu Lys Ala Ala Glu
    335                 340                 345

GAG GGC GAC GGC TCG GAG TTG CTG GCC CTC GCC GAC GGC TAC AAC GAG           1284
Glu Gly Asp Gly Ser Glu Leu Leu Ala Leu Ala Asp Gly Tyr Asn Glu
350                 355                 360                 365

CGT GAT CCC TCG GGG CGC TAC GGC ACG ACG ACC CAC TCG CAA AGG GTC           1332
Arg Asp Pro Ser Gly Arg Tyr Gly Thr Thr Thr His Ser Gln Arg Val
                370                 375                 380

ATA TCG TGC CTG GAC GAC AAG CAG AGG CCG ACC GTG GAG GAG ACG AAG           1380
Ile Ser Cys Leu Asp Asp Lys Gln Arg Pro Thr Val Glu Glu Thr Lys
            385                 390                 395

AAG CTG CTG CCG AGG TTC GAG AAG GTC TCT CCC GTC TTC GGC GCC TTC           1428
Lys Leu Leu Pro Arg Phe Glu Lys Val Ser Pro Val Phe Gly Ala Phe
        400                 405                 410

CTC GGC TGG GAC ACG GCC GGG TGG TGC CAC GAC TGG CCG GTG GCC GGT           1476
Leu Gly Trp Asp Thr Ala Gly Trp Cys His Asp Trp Pro Val Ala Gly
    415                 420                 425

CAG CAC GAG ACC GCG GAG GTG AGC GCG CCC GAC GCG GCC CCG GTC CTG           1524
Gln His Glu Thr Ala Glu Val Ser Ala Pro Asp Ala Ala Pro Val Leu
430                 435                 440                 445

GTG GTC GGC AAC ACG GGC GAC CCG GCC ACG CCC TAC GAG GGC GCC CGC           1572
Val Val Gly Asn Thr Gly Asp Pro Ala Thr Pro Tyr Glu Gly Ala Arg
                450                 455                 460

AGG ATG GCG GAC GAG CTG GGC AAG GAC GTC GGC GTG GTG CTG ACC TGG           1620
Arg Met Ala Asp Glu Leu Gly Lys Asp Val Gly Val Val Leu Thr Trp
            465                 470                 475
```

```
CAG GGC GAG GGA CAC GGT GCC TAC GGG AAC GGA AGC GAC TGT GTC GAC         1668
Gln Gly Glu Gly His Gly Ala Tyr Gly Asn Gly Ser Asp Cys Val Asp
        480                 485                 490

TCC GCG GTG GAC GCC TAC CTG TTG AAG GGG ACG GTG CCG AAG GAC GGC         1716
Ser Ala Val Asp Ala Tyr Leu Leu Lys Gly Thr Val Pro Lys Asp Gly
    495                 500                 505

AAG GTC TGC TCA TGACGGCGGC GGGGGCTTCG GGCACCTGCG GTGCGCGAAA             1768
Lys Val Cys Ser
510

CCCCCGCCG                                                               1777

(2) INFORMATION FOR SEQ ID NO:6:

(i) SEQUENCE CHARACTERISTICS:
        (A) LENGTH: 513 amino acids
        (B) TYPE: amino acid
        (D) TOPOLOGY: linear (ii) MOLECULE TYPE: protein (xi) SEQUENCE DESCRIPTION: SEQ ID NO:6:

Met Ala Arg Leu Val Arg Trp Thr Ala Leu Thr Ala Ala Ala Leu
 1               5                  10                  15

Leu Thr Ala Gly Cys Ser Gly Gly Ser Ser Asp Glu Asp Lys Asp Asp
                20                  25                  30

Gly Gly Arg Ser Ser Ala Gly Pro Ser Ala Ala Pro Ser Gly Val
         35                  40                  45

Pro Glu Ala Leu Ala Ser Gln Thr Leu Asp Trp Ala Arg Cys Glu Gly
     50                  55                  60

Ser Asp Asp Ala Pro Ala Pro Asp Gly Asp Trp Arg Cys Ala Thr Leu
65                  70                  75                  80

Lys Ala Pro Leu Asp Trp Ser Asp Pro Asp Gly Glu Thr Ile Asp Leu
                85                  90                  95

Ala Leu Ile Arg Ser Arg Ala Ser Gly Asp Asp Arg Ile Gly Ser Leu
            100                 105                 110

Leu Phe Asn Phe Gly Gly Pro Gly Ala Ser Gly Val Ser Thr Met Pro
        115                 120                 125

Ser Tyr Ala Asp Thr Val Ser Ser Leu His Glu Arg Tyr Asp Leu Val
    130                 135                 140

Ser Trp Asp Pro Arg Gly Val Ala Ala Ser Glu Gly Val Arg Cys Arg
145                 150                 155                 160

Thr Asp Glu Ala Ile Glu Ala Ala Glu Ser Val Asp Ser Thr Pro Asp
                165                 170                 175

Ser Pro Ala Glu Glu Gln Ala Tyr Leu Lys Asp Ala Ala Asp Phe Gly
            180                 185                 190

Arg Gly Cys Glu Lys Ala Ala Gly Lys Leu Met Glu His Val Ser Thr
        195                 200                 205

Thr Asp Thr Ala Arg Asp Met Asp Leu Met Arg His Val Leu Gly Asp
    210                 215                 220

Glu Arg Met His Tyr Phe Gly Ile Ser Tyr Gly Thr Glu Leu Gly Gly
225                 230                 235                 240

Val Tyr Ala His Leu Phe Pro Glu His Val Gly Arg Val Ile Leu Asp
                245                 250                 255

Ala Val Val Asp Pro Gly Ala Asp Thr Met Gly His Ala Glu Asn Gln
            260                 265                 270

Ala Arg Gly Phe Gln Arg Ala Leu Asp Asp Tyr Leu Glu Ser Thr Gly
        275                 280                 285
```

```
Gln Glu Pro Glu Gln Gly Ser Arg Lys Ile Ala Gly Leu Leu Glu Arg
        290                 295                 300

Leu Asp Ala Glu Pro Leu Pro Thr Ser Ser Pro Gly Arg Glu Leu Thr
305                 310                 315                 320

Gln Thr Leu Ala Phe Thr Gly Ile Val Leu Pro Leu Tyr Ser Glu Ser
                325                 330                 335

Gly Trp Pro Ala Leu Thr Ser Ala Leu Lys Ala Ala Glu Glu Gly Asp
                340                 345                 350

Gly Ser Glu Leu Leu Ala Leu Ala Asp Gly Tyr Asn Glu Arg Asp Pro
            355                 360                 365

Ser Gly Arg Tyr Gly Thr Thr Thr His Ser Gln Arg Val Ile Ser Cys
    370                 375                 380

Leu Asp Asp Lys Gln Arg Pro Thr Val Glu Glu Thr Lys Lys Leu Leu
385                 390                 395                 400

Pro Arg Phe Glu Lys Val Ser Pro Val Phe Gly Ala Phe Leu Gly Trp
                405                 410                 415

Asp Thr Ala Gly Trp Cys His Asp Trp Pro Val Ala Gly Gln His Glu
                420                 425                 430

Thr Ala Glu Val Ser Ala Pro Asp Ala Ala Pro Val Leu Val Val Gly
            435                 440                 445

Asn Thr Gly Asp Pro Ala Thr Pro Tyr Glu Gly Ala Arg Arg Met Ala
    450                 455                 460

Asp Glu Leu Gly Lys Asp Val Gly Val Val Leu Thr Trp Gln Gly Glu
465                 470                 475                 480

Gly His Gly Ala Tyr Gly Asn Gly Ser Asp Cys Val Asp Ser Ala Val
                485                 490                 495

Asp Ala Tyr Leu Leu Lys Gly Thr Val Pro Lys Asp Gly Lys Val Cys
                500                 505                 510

Ser (2) INFORMATION FOR SEQ ID NO:7:

(i) SEQUENCE CHARACTERISTICS:
        (A) LENGTH: 1821 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 104..1720

(ix) FEATURE:
        (A) NAME/KEY: sig_peptide
        (B) LOCATION: 104..244

(ix) FEATURE:
        (A) NAME/KEY: mat_peptide
        (B) LOCATION: 245..1720

(xi) SEQUENCE DESCRIPTION: SEQ ID NO:7:

CCCGGGCCCG CGTCGGAGTC ATGACCGGTT GACGCCGTAA CACGTACGGG GCACGCGCAC      60

CACGCACCGC AACTGCTTCG TCGCGGAGAG TTACGCTCGC TGA ATG GAC ACA AGG     115
                                              Met Asp Thr Arg
                                              -47         -45

CGC ACT CAC CGC AGG ACC CGC ACC GGC GGC ACC CGT TTC CGG GCC ACG     163
Arg Thr His Arg Arg Thr Arg Thr Gly Gly Thr Arg Phe Arg Ala Thr
        -40                 -35                 -30
```

-continued

```
CTG CTC ACC GCC GCG CTG CTC GCC ACC GCC TGC TCG GCC GGG GGC GCG      211
Leu Leu Thr Ala Ala Leu Leu Ala Thr Ala Cys Ser Ala Gly Gly Ala
        -25             -20             -15

TCG ACG TCC GCC GGA TCC CCC GCG GCC AAG GCG GCC GGC GCG ACG GAG      259
Ser Thr Ser Ala Gly Ser Pro Ala Ala Lys Ala Ala Gly Ala Thr Glu
        -10              -5               1               5

GCG GCC ACG GCG ACC CTG ACC CCC CTG CCG AAG GCC ACG CCC GCC GAG      307
Ala Ala Thr Ala Thr Leu Thr Pro Leu Pro Lys Ala Thr Pro Ala Glu
                 10              15              20

CTG TCC CCG TAC TAC GAG CAG AAG CTC GGC TGG CGC GAC TGC GGC GTC      355
Leu Ser Pro Tyr Tyr Glu Gln Lys Leu Gly Trp Arg Asp Cys Gly Val
                 25              30              35

CCG GGC TTC CAG TGC GCC ACC ATG AAG GCC CCG CTC GAC TAC GCC AAG      403
Pro Gly Phe Gln Cys Ala Thr Met Lys Ala Pro Leu Asp Tyr Ala Lys
         40              45              50

CCC GCC GAC GGC GAC GTC CGG CTC GCG GTG GCC CGC AAG AAG GCC ACG      451
Pro Ala Asp Gly Asp Val Arg Leu Ala Val Ala Arg Lys Lys Ala Thr
     55              60              65

GGG CCG GGC AAG CGC CTC GGC TCG CTG CTG GTC AAC CCG GGC GGA CCG      499
Gly Pro Gly Lys Arg Leu Gly Ser Leu Leu Val Asn Pro Gly Gly Pro
 70              75              80              85

GGC GGC TCG GCG ATC GGC TAC CTC CAG CAG TAC GCG GGC ATC GGC TAC      547
Gly Gly Ser Ala Ile Gly Tyr Leu Gln Gln Tyr Ala Gly Ile Gly Tyr
             90              95             100

CCG GCG AAG GTC CGC GCC CAG TAC GAC ATG GTG GCG GTC GAC CCC CGG      595
Pro Ala Lys Val Arg Ala Gln Tyr Asp Met Val Ala Val Asp Pro Arg
            105             110             115

GGC GTG GCC CGC AGT GAA CCC GTC GAG TGC CTG GAC GGG CGC GAG ATG      643
Gly Val Ala Arg Ser Glu Pro Val Glu Cys Leu Asp Gly Arg Glu Met
        120             125             130

GAC GCG TAC ACG CGC ACC GAC GTC ACC CCG GAC GAC GCG GGC GAG ACG      691
Asp Ala Tyr Thr Arg Thr Asp Val Thr Pro Asp Asp Ala Gly Glu Thr
        135             140             145

GAC GAG CTG GTC GAC GCC TAC AAG GAG TTC GCC GAG GGC TGC GGG GCG      739
Asp Glu Leu Val Asp Ala Tyr Lys Glu Phe Ala Glu Gly Cys Gly Ala
150             155             160             165

GAC GCG CCG AAG CTG CTG CGC CAC GTC TCC ACG GTC GAG GCG GCA CGC      787
Asp Ala Pro Lys Leu Leu Arg His Val Ser Thr Val Glu Ala Ala Arg
            170             175             180

GAC ATG GAC GTC CTG CGC GCG GTG CTG GGC GAC GAG AAG CTG ACC TAC      835
Asp Met Asp Val Leu Arg Ala Val Leu Gly Asp Glu Lys Leu Thr Tyr
            185             190             195

GTG GGA GCG TCG TAC GGC ACC TTC CTG GGC GCG ACC TAC GCC GGT CTG      883
Val Gly Ala Ser Tyr Gly Thr Phe Leu Gly Ala Thr Tyr Ala Gly Leu
            200             205             210

TTC CCC GAC CGG ACG GGC CGC CTG GTC CTG GAC GGC GCG ATG GAC CCC      931
Phe Pro Asp Arg Thr Gly Arg Leu Val Leu Asp Gly Ala Met Asp Pro
        215             220             225

TCG CTG CCC GCC CGC CGC CTG AAC CTG GAG CAG ACG GAG GGC TTC GAG      979
Ser Leu Pro Ala Arg Arg Leu Asn Leu Glu Gln Thr Glu Gly Phe Glu
230             235             240             245

ACG GCG TTC CAG TCC TTC GCG AAG GAC TGC GTG AAG CAG CCG GAC TGC     1027
Thr Ala Phe Gln Ser Phe Ala Lys Asp Cys Val Lys Gln Pro Asp Cys
            250             255             260

CCC CTC GGC GAC AAG GAC ACC ACC CCC GAC CAG GTC GGC AAG AAC CTC     1075
Pro Leu Gly Asp Lys Asp Thr Thr Pro Asp Gln Val Gly Lys Asn Leu
            265             270             275

AAG TCC TTC TTC GAC GAC CTG GAC GCG AAG CCC CTG CCC GCC GGC GAC     1123
Lys Ser Phe Phe Asp Asp Leu Asp Ala Lys Pro Leu Pro Ala Gly Asp
```

```
          280                 285                 290
GCC GAC GGC CGC AAG CTC ACC GAA TCC CTC GCC ACC ACC GGC GTG ATC    1171
Ala Asp Gly Arg Lys Leu Thr Glu Ser Leu Ala Thr Thr Gly Val Ile
    295                 300                 305

GCC GCG ATG TAC GAC GAG GGC GCC TGG CAG CAG CTG CGC GAG TCC CTC    1219
Ala Ala Met Tyr Asp Glu Gly Ala Trp Gln Gln Leu Arg Glu Ser Leu
310                 315                 320                 325

ACC TCG GCG ATC AAG GAG AAG GAC GGT GCG GGC CTG CTG ATC CTC TCC    1267
Thr Ser Ala Ile Lys Glu Lys Asp Gly Ala Gly Leu Leu Ile Leu Ser
                330                 335                 340

GAC AGC TAC TAC GAG CGC GAG GCC GAC GGC GGC TAC AGC AAC CTG ATG    1315
Asp Ser Tyr Tyr Glu Arg Glu Ala Asp Gly Gly Tyr Ser Asn Leu Met
            345                 350                 355

TTC GCC AAC GCC GCC GTG AAC TGC CTC GAC CTC CCC GCC GCC TTC TCC    1363
Phe Ala Asn Ala Ala Val Asn Cys Leu Asp Leu Pro Ala Ala Phe Ser
        360                 365                 370

TCC CCG GAC GAG GTG CGC GAC GCC CTC CCC GAC TTC GAG AAG GCG TCC    1411
Ser Pro Asp Glu Val Arg Asp Ala Leu Pro Asp Phe Glu Lys Ala Ser
    375                 380                 385

CCG GTC TTC GGC GAG GGC CTC GCC TGG TCC TCC CTG AAC TGC GCG TAC    1459
Pro Val Phe Gly Glu Gly Leu Ala Trp Ser Ser Leu Asn Cys Ala Tyr
390                 395                 400                 405

TGG CCG GTG AAG CCC ACG GGG GAG CCG CAC CGC ATC GAG GCG GCC GGC    1507
Trp Pro Val Lys Pro Thr Gly Glu Pro His Arg Ile Glu Ala Ala Gly
                410                 415                 420

GCC ACC CCG ATC GTC GTG GTC GGC ACC ACC CGC GAC CCG GCC ACC CCC    1555
Ala Thr Pro Ile Val Val Val Gly Thr Thr Arg Asp Pro Ala Thr Pro
            425                 430                 435

TAC CGC TGG GCC GAG GCC CTC TCC GAC CAG CTC ACC TCC GGC CAC CTC    1603
Tyr Arg Trp Ala Glu Ala Leu Ser Asp Gln Leu Thr Ser Gly His Leu
        440                 445                 450

CTC ACC TAC GAG GGA GAC GGC CAC ACC GCG TAC GGC CGC GGC AGC TCC    1651
Leu Thr Tyr Glu Gly Asp Gly His Thr Ala Tyr Gly Arg Gly Ser Ser
    455                 460                 465

TGC ATC GAC TCC GCG ATC AAC ACG TAC CTG CTG ACC GGC ACC GCC CCG    1699
Cys Ile Asp Ser Ala Ile Asn Thr Tyr Leu Leu Thr Gly Thr Ala Pro
470                 475                 480                 485

GAG GAC GGC AAG CGC TGC TCG TAACCCCCGC CTGCCCGCCC CGGGACCCAC        1750
Glu Asp Gly Lys Arg Cys Ser
                490

GCCTCCGGGG GCGGGTTCGG AGCACCCCGG GAAACTGTGT AGACTTGCCG ACGTTGCTGA   1810

TCGCACCATG G                                                        1821

(2) INFORMATION FOR SEQ ID NO:8:

(i) SEQUENCE CHARACTERISTICS:
        (A) LENGTH: 539 amino acids
        (B) TYPE: amino acid
        (D) TOPOLOGY: linear (ii) MOLECULE TYPE: protein (xi) SEQUENCE DESCRIPTION: SEQ ID NO:8:

Met Asp Thr Arg Arg Thr His Arg Arg Thr Arg Thr Gly Gly Thr Arg
-47                 -45                 -40                 -35

Phe Arg Ala Thr Leu Leu Thr Ala Ala Leu Leu Ala Thr Ala Cys Ser
        -30                 -25                 -20

Ala Gly Gly Ala Ser Thr Ser Ala Gly Ser Pro Ala Ala Lys Ala Ala
    -15                 -10                  -5                  1
```

-continued

```
Gly Ala Thr Glu Ala Ala Thr Ala Thr Leu Thr Pro Leu Pro Lys Ala
                5                  10                  15
Thr Pro Ala Glu Leu Ser Pro Tyr Tyr Glu Gln Lys Leu Gly Trp Arg
            20                  25                  30
Asp Cys Gly Val Pro Gly Phe Gln Cys Ala Thr Met Lys Ala Pro Leu
        35                  40                  45
Asp Tyr Ala Lys Pro Ala Asp Gly Asp Val Arg Leu Ala Val Ala Arg
50                  55                  60                  65
Lys Lys Ala Thr Gly Pro Gly Lys Arg Leu Gly Ser Leu Leu Val Asn
                70                  75                  80
Pro Gly Gly Pro Gly Gly Ser Ala Ile Gly Tyr Leu Gln Gln Tyr Ala
            85                  90                  95
Gly Ile Gly Tyr Pro Ala Lys Val Arg Ala Gln Tyr Asp Met Val Ala
        100                 105                 110
Val Asp Pro Arg Gly Val Ala Arg Ser Glu Pro Val Glu Cys Leu Asp
    115                 120                 125
Gly Arg Glu Met Asp Ala Tyr Thr Arg Thr Asp Val Thr Pro Asp Asp
130                 135                 140                 145
Ala Gly Glu Thr Asp Glu Leu Val Asp Ala Tyr Lys Glu Phe Ala Glu
                150                 155                 160
Gly Cys Gly Ala Asp Ala Pro Lys Leu Leu Arg His Val Ser Thr Val
            165                 170                 175
Glu Ala Ala Arg Asp Met Asp Val Leu Arg Ala Val Leu Gly Asp Glu
        180                 185                 190
Lys Leu Thr Tyr Val Gly Ala Ser Tyr Gly Thr Phe Leu Gly Ala Thr
    195                 200                 205
Tyr Ala Gly Leu Phe Pro Asp Arg Thr Gly Arg Leu Val Leu Asp Gly
210                 215                 220                 225
Ala Met Asp Pro Ser Leu Pro Ala Arg Arg Leu Asn Leu Glu Gln Thr
                230                 235                 240
Glu Gly Phe Glu Thr Ala Phe Gln Ser Phe Ala Lys Asp Cys Val Lys
            245                 250                 255
Gln Pro Asp Cys Pro Leu Gly Asp Lys Asp Thr Thr Pro Asp Gln Val
        260                 265                 270
Gly Lys Asn Leu Lys Ser Phe Phe Asp Asp Leu Asp Ala Lys Pro Leu
    275                 280                 285
Pro Ala Gly Asp Ala Asp Gly Arg Lys Leu Thr Glu Ser Leu Ala Thr
290                 295                 300                 305
Thr Gly Val Ile Ala Ala Met Tyr Asp Glu Gly Ala Trp Gln Gln Leu
                310                 315                 320
Arg Glu Ser Leu Thr Ser Ala Ile Lys Glu Lys Asp Gly Ala Gly Leu
            325                 330                 335
Leu Ile Leu Ser Asp Ser Tyr Tyr Glu Arg Glu Ala Asp Gly Gly Tyr
        340                 345                 350
Ser Asn Leu Met Phe Ala Asn Ala Ala Val Asn Cys Leu Asp Leu Pro
    355                 360                 365
Ala Ala Phe Ser Ser Pro Asp Glu Val Arg Asp Ala Leu Pro Asp Phe
370                 375                 380                 385
Glu Lys Ala Ser Pro Val Phe Gly Glu Gly Leu Ala Trp Ser Ser Leu
                390                 395                 400
Asn Cys Ala Tyr Trp Pro Val Lys Pro Thr Gly Glu Pro His Arg Ile
            405                 410                 415
Glu Ala Ala Gly Ala Thr Pro Ile Val Val Gly Thr Thr Arg Asp
```

```
                  420                 425                 430
Pro Ala Thr Pro Tyr Arg Trp Ala Glu Ala Leu Ser Asp Gln Leu Thr
                435                 440                 445
Ser Gly His Leu Leu Thr Tyr Glu Gly Asp Gly His Thr Ala Tyr Gly
450                 455                 460                 465
Arg Gly Ser Ser Cys Ile Asp Ser Ala Ile Asn Thr Tyr Leu Leu Thr
                470                 475                 480
Gly Thr Ala Pro Glu Asp Gly Lys Arg Cys Ser
                485                 490
```

(2) INFORMATION FOR SEQ ID NO:9:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:9:

```
Gly Xaa Ser Xaa Gly
1               5
```

(2) INFORMATION FOR SEQ ID NO:10:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:10:

```
Gly Val Ser Tyr Gly
1               5
```

(2) INFORMATION FOR SEQ ID NO:11:

(i) SEQUENCE CHARACTERISTICS:
        (A) LENGTH: 30 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:11:

```
Arg Val Asp Leu Val Gly Asn Ser Phe Gly Gly Ala Leu Ser Leu Ala
1               5                   10                  15
Phe Ala Ile Arg Phe Pro His Arg Val Arg Arg Leu Val Leu
                20                  25                  30
```

(2) INFORMATION FOR SEQ ID NO:12:

(i) SEQUENCE CHARACTERISTICS:
        (A) LENGTH: 381 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:12:

```
Met Arg Gly Lys Lys Val Trp Ile Ser Leu Leu Phe Ala Leu Ala Leu
```

```
              1               5                   10                  15
          Ile Phe Thr Met Ala Phe Gly Ser Thr Ser Ser Ala Gln Ala Gly
                           20                  25              30
          Lys Ser Asn Gly Glu Lys Lys Tyr Ile Val Gly Phe Lys Gln Thr Met
                       35                  40                  45
          Ser Thr Met Ser Ala Ala Lys Lys Asp Val Ile Ser Glu Lys Gly
                   50                  55                  60
          Gly Lys Val Gln Lys Gln Phe Lys Tyr Val Asp Ala Ala Ser Ala Thr
          65                  70                  75                  80
          Leu Asn Glu Lys Ala Val Lys Glu Leu Lys Lys Asp Pro Ser Val Ala
                           85                  90                  95
          Tyr Val Glu Glu Asp His Val Ala His Ala Tyr Ala Gln Ser Val Pro
                           100                 105                 110
          Tyr Gly Val Ser Gln Ile Lys Ala Pro Ala Leu His Ser Gln Gly Tyr
                       115                 120                 125
          Thr Gly Ser Asn Val Lys Val Ala Val Ile Asp Ser Gly Ile Asp Ser
                   130                 135                 140
          Ser His Pro Asp Leu Lys Val Ala Gly Gly Ala Ser Met Val Pro Ser
          145                 150                 155                 160
          Glu Thr Asn Pro Phe Gln Asp Asn Asn Ser His Gly Thr His Val Ala
                           165                 170                 175
          Gly Thr Val Ala Ala Leu Asn Asn Ser Ile Gly Val Leu Gly Val Ala
                           180                 185                 190
          Pro Ser Ala Ser Leu Tyr Ala Val Lys Val Leu Gly Ala Asp Gly Ser
                       195                 200                 205
          Gly Gln Tyr Ser Trp Ile Ile Asn Gly Ile Glu Trp Ala Ile Ala Asn
                   210                 215                 220
          Asn Met Asp Val Ile Asn Met Ser Leu Gly Gly Pro Ser Gly Ser Ala
          225                 230                 235                 240
          Ala Leu Lys Ala Ala Val Asp Lys Ala Val Ala Ser Gly Val Val Val
                           245                 250                 255
          Val Ala Ala Ala Gly Asn Glu Gly Thr Ser Gly Ser Ser Ser Thr Val
                           260                 265                 270
          Gly Tyr Pro Gly Lys Tyr Pro Ser Val Ile Ala Val Gly Ala Val Asp
                       275                 280                 285
          Ser Ser Asn Arg Ala Ser Phe Ser Ser Val Gly Pro Glu Leu Asp Val
                   290                 295                 300
          Met Ala Pro Gly Val Ser Ile Gln Ser Thr Leu Pro Gly Asn Lys Tyr
          305                 310                 315                 320
          Gly Ala Tyr Asn Gly Thr Ser Met Ala Ser Pro His Val Ala Gly Ala
                           325                 330                 335
          Ala Ala Leu Ile Leu Ser Lys His Pro Asn Trp Thr Asn Thr Gln Val
                           340                 345                 350
          Arg Ser Ser Leu Glu Asn Thr Thr Thr Lys Leu Gly Asp Ser Phe Tyr
                       355                 360                 365
          Tyr Gly Lys Gly Leu Ile Asn Val Gln Ala Ala Ala Gln
                   370                 375                 380

(2) INFORMATION FOR SEQ ID NO:13:

(i) SEQUENCE CHARACTERISTICS:
            (A) LENGTH: 11 amino acids
            (B) TYPE: amino acid
            (C) STRANDEDNESS:
            (D) TOPOLOGY: linear
```

(ii) MOLECULE TYPE: peptide (xi) SEQUENCE DESCRIPTION: SEQ ID NO:13:

Ala Glu Pro Xaa Ala Val Asp Ile Asp Arg Leu
1               5                   10

(2) INFORMATION FOR SEQ ID NO:14:

(i) SEQUENCE CHARACTERISTICS:
            (A) LENGTH: 6 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:14:

Ala Pro Ala Ala Pro Ala
1               5

(2) INFORMATION FOR SEQ ID NO:15:

(i) SEQUENCE CHARACTERISTICS:
            (A) LENGTH: 7 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:15:

Ala Pro Ala Arg Ser Pro Ala
1               5

(2) INFORMATION FOR SEQ ID NO:16:

(i) SEQUENCE CHARACTERISTICS:
            (A) LENGTH: 10 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:16:

Ser Ala Gly Gly Ala Ser Thr Xaa Ala Gly
1               5                   10

(2) INFORMATION FOR SEQ ID NO:17:

(i) SEQUENCE CHARACTERISTICS:
            (A) LENGTH: 15 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:17:

Ala Pro Ala Ala Pro Ala Ser Gly Gly Ser Ser Asp Glu Asp Lys
1               5                   10                  15

(2) INFORMATION FOR SEQ ID NO:18:

(i) SEQUENCE CHARACTERISTICS:
            (A) LENGTH: 14 base pairs
            (B) TYPE: nucleic acid
            (C) STRANDEDNESS: single (D) TOPOLOGY: linear (ii) MOLECULE TYPE: DNA (xi) SEQUENCE DESCRIPTION: SEQ ID NO:18:

GCGCCTGCAG CCTA                                                           14

(2) INFORMATION FOR SEQ ID NO:19:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:19:

AGCTTAGGCT GCAGGCGCTG CA                                                  22

(2) INFORMATION FOR SEQ ID NO:20:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:20:

GCGCCGGCGG CGCCTGCAGC CTA                                                 23

(2) INFORMATION FOR SEQ ID NO:21:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:21:

AGCTTAGGCT GCAGGCGCCG CCGGCGCTGC A                                        31

(2) INFORMATION FOR SEQ ID NO:22:

(i) SEQUENCE CHARACTERISTICS:
        (A) LENGTH: 30 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:22:

Asp Thr Gly Ala Pro Gln Val Leu Gly Gly Glu Asp Leu Ala Ala Ala
1               5                  10                  15

Lys Ala Ala Ser Ala Lys Ala Glu Gly Gln Asp Pro Leu Glu
            20                  25                  30

(2) INFORMATION FOR SEQ ID NO:23:

(i) SEQUENCE CHARACTERISTICS:
        (A) LENGTH: 22 amino acids
        (B) TYPE: amino acid
        (C) STRANDEDNESS:

-continued

```
            (D) TOPOLOGY: linear (ii) MOLECULE TYPE: protein (xi) SEQUENCE DESCRIPTION: SEQ ID NO:23:

Gly Val Ser Tyr Gly Thr Tyr Leu Gly Ala Val Tyr Gly Thr Leu Phe
1               5                   10                  15

Pro Asp His Val Arg Arg
            20

(2) INFORMATION FOR SEQ ID NO:24:

(i) SEQUENCE CHARACTERISTICS:
          (A) LENGTH: 22 amino acids
          (B) TYPE: amino acid
          (C) STRANDEDNESS:
          (D) TOPOLOGY: linear (ii) MOLECULE TYPE: protein (xi) SEQUENCE DESCRIPTION: SEQ ID NO:24:

Gly Ala Ser Tyr Gly Thr Phe Leu Gly Ala Thr Tyr Ala Gly Leu Phe
1               5                   10                  15

Pro Asp Arg Thr Gly Arg
            20

(2) INFORMATION FOR SEQ ID NO:25:

(i) SEQUENCE CHARACTERISTICS:
          (A) LENGTH: 22 amino acids
          (B) TYPE: amino acid
          (C) STRANDEDNESS:
          (D) TOPOLOGY: linear (ii) MOLECULE TYPE: protein (xi) SEQUENCE DESCRIPTION: SEQ ID NO:25:

Gly Ile Ser Tyr Gly Thr Glu Leu Gly Gly Val Tyr Ala His Leu Phe
1               5                   10                  15

Pro Glu His Val Gly Arg
            20
```